United States Patent [19]

Patton et al.

[11] Patent Number: 4,989,610
[45] Date of Patent: Feb. 5, 1991

[54] METHOD AND SYSTEM OF ECG DATA REVIEW AND ANALYSIS

[75] Inventors: Craig A. Patton, Renton; Craig S. Siegman, Redmond; Roy E. Sundahl, Woodinville; Steven W. Webert, Redmond, all of Wash. Harold G. Dow; Hillsboro; Ore.,

[73] Assignee: SpaceLabs, Inc., Redmond, Wash.

[21] Appl. No.: 121,817

[22] Filed: Nov. 16, 1987

[51] Int. Cl.$^5$ .............................. A61B 5/04
[52] U.S. Cl. ...................... 128/695; 128/696; 128/700; 128/702; 128/711; 128/712; 364/413.06
[58] Field of Search .................. 128/695–700, 128/702–705, 708–712; 364/413.01, 413.02, 413.03, 413.05, 413.06

[56] References Cited

U.S. PATENT DOCUMENTS

| | | | |
|---|---|---|---|
| 3,978,470 | 8/1976 | McGuire | 128/710 |
| 4,156,920 | 5/1979 | Winograd | 364/726 |
| 4,316,249 | 2/1982 | Gallant et al. | 128/708 |
| 4,537,202 | 8/1985 | Mancini et al. | 128/712 |
| 4,779,199 | 10/1988 | Yoneda et al. | 128/710 |

OTHER PUBLICATIONS

"Automated Family Classification . . . " by Spitz et al.; Med. Instr., vol. 12, No. 6, Nov.–Dec. 1978, pp. 322–323.
"A Minicomputer Based System . . . " by Higgins et al.; Computers in Cartiology; Sep. 12–14, 1978, pp. 355–358.
"Argus/2H" by Clark et al.; Computers in Cartiology; Sep. 12–14, 1978, pp. 397–398.

Primary Examiner—William E. Kamm
Assistant Examiner—David Shay
Attorney, Agent, or Firm—Seed and Berry

[57] ABSTRACT

A method and computerized system for ECG data review and analysis are provided. In preferred embodiments, a transformation is performed on beat data and the transformed data are categorized into beat "bins." The clinician/user may select sensitivity to vary the number of bins created by the system. Once beats are preliminarily assigned to bins by the system, the clinician/user may review beats by bin and reassigned beats as desired. In preferred embodiments, recategorization is accomplished by "dragging" a beat to a new bin with the aid of a pointing device or "mouse." In preferred embodiments, a superimposition mode allows dynamic review of beat graphs with automatic detection, color coding, and optional pause at abnormal beats. Audio information is also preferably provided to aid the clinician/user in detecting abnormal beats. A P-wave marker capability is also provided to give a constant reference point during beat review in the superimposition mode. Preferred embodiments also provide the clinician/user immediate access to surrounding real-time data when reviewing individual beats.

13 Claims, 54 Drawing Sheets

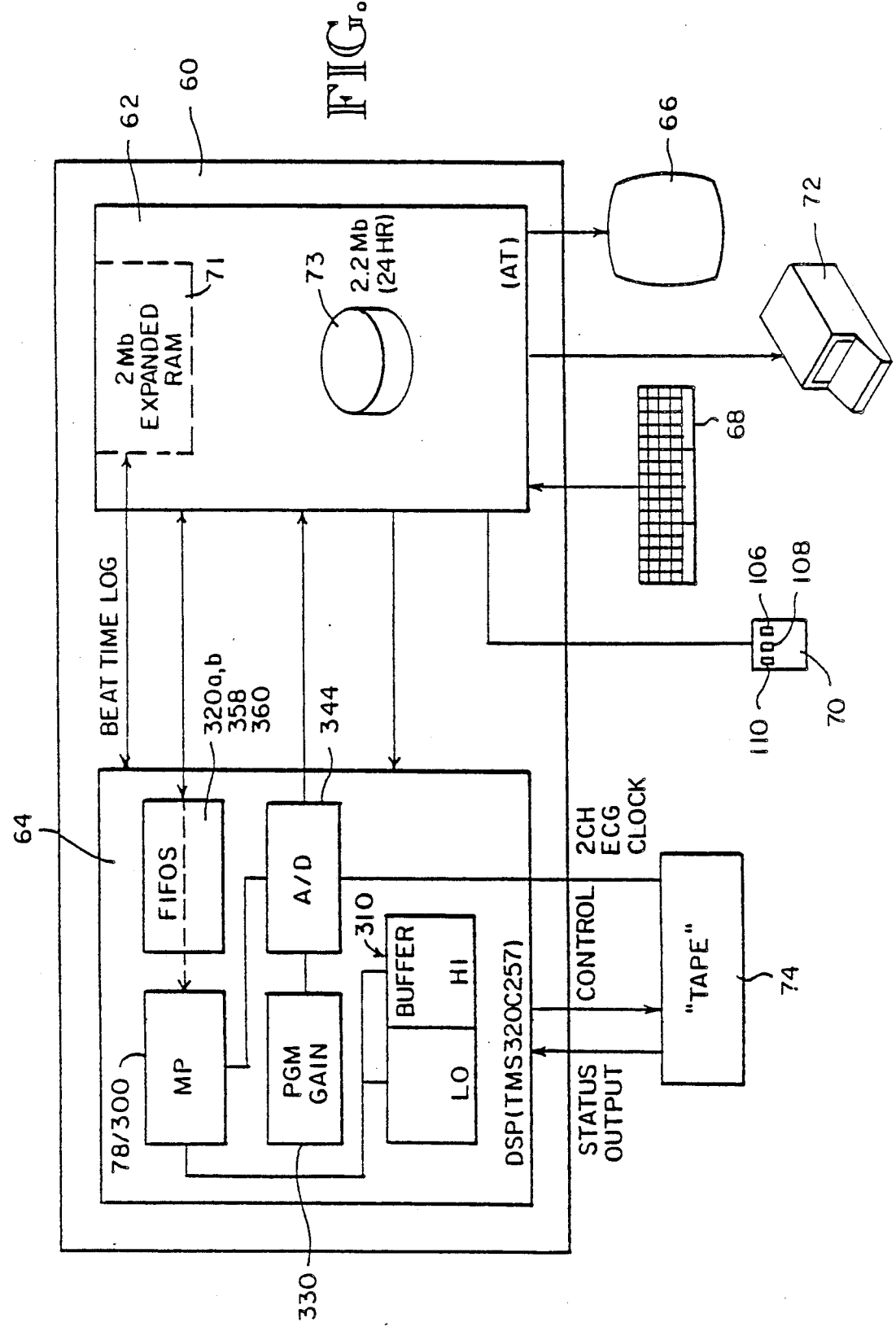

FIG. 2

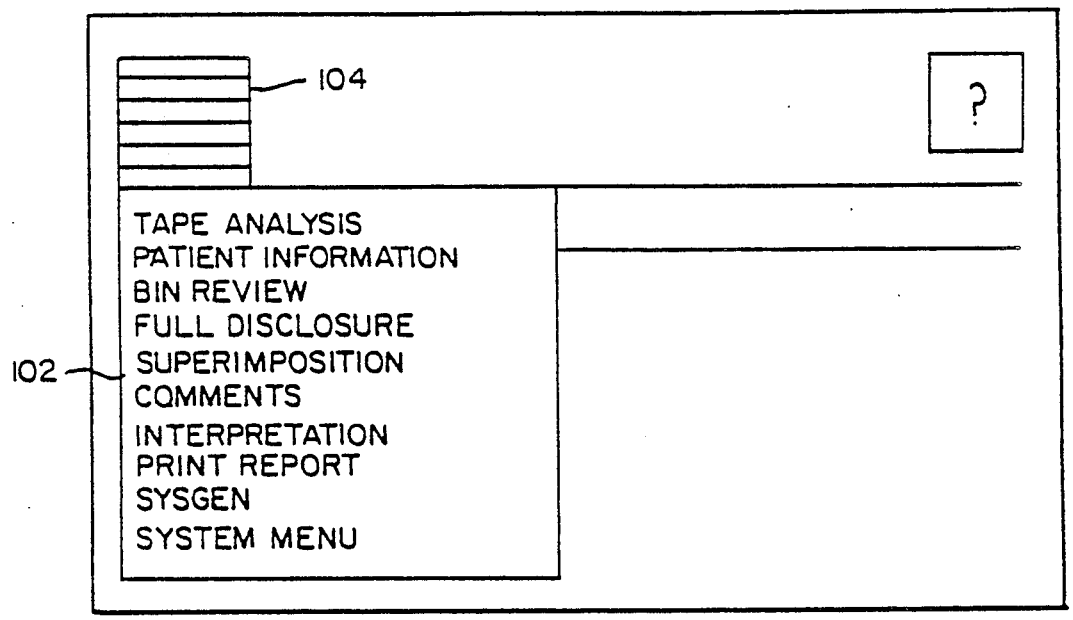

```
          ┌──104
         ┌─────┐                                    ┌───┐
         │═════│                                    │ ? │
         │═════│                                    └───┘
         │═════│
         └──┬──┴──────────────────────
            │ TAPE ANALYSIS
            │ PATIENT INFORMATION
            │ BIN REVIEW
            │ FULL DISCLOSURE
     102 ──│ SUPERIMPOSITION
            │ COMMENTS
            │ INTERPRETATION
            │ PRINT REPORT
            │ SYSGEN
            │ SYSTEM MENU
```

FIG. 3

|  TAPE ANALYSIS OPTIONS |  |  |  |
|---|---|---|---|
| ERASE PATIENT INFORMATION: | YES | NO | |
| ERASE REPORT COMMENTARY: | YES | NO | |
| MEASURE ST ON CHANNEL: | 1 | 2 | |
| ANALYZE BEATS ON CHANNEL: | 1 | 2 | BOTH |
| TAPE MACHINE: CASS | R-R | | |
| BINNING SENSITIVITY: | 1 2 3 4 5 | | |
|  | LO  NOM  HI | | |

ACCEPT

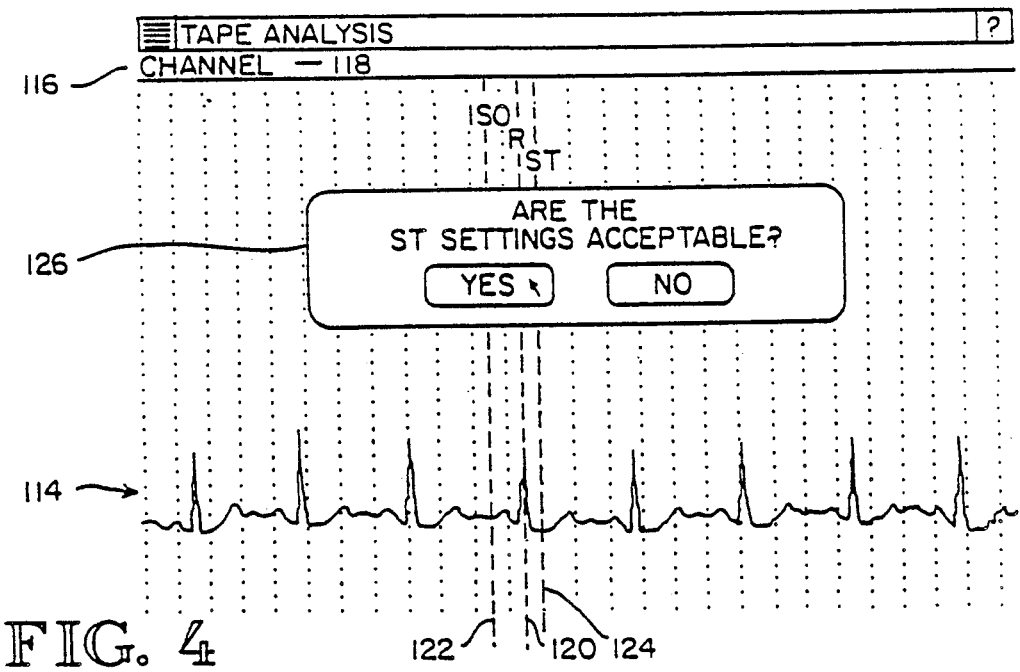
FIG. 4
FIG. 5
FIG. 6

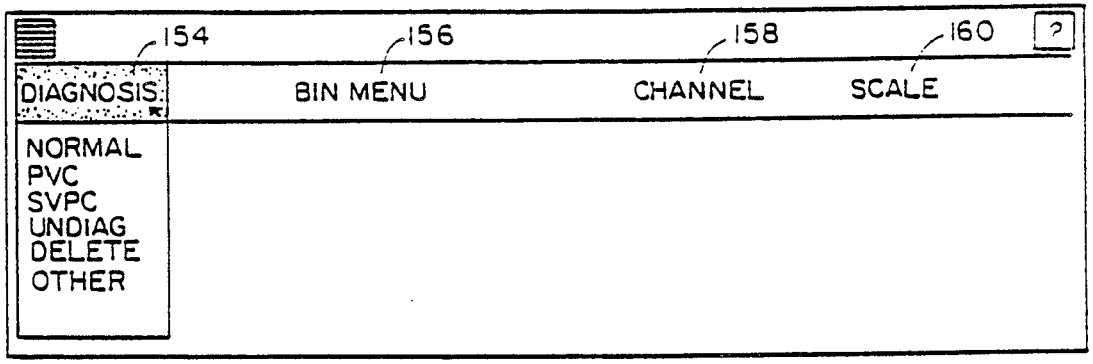
FIG. 7
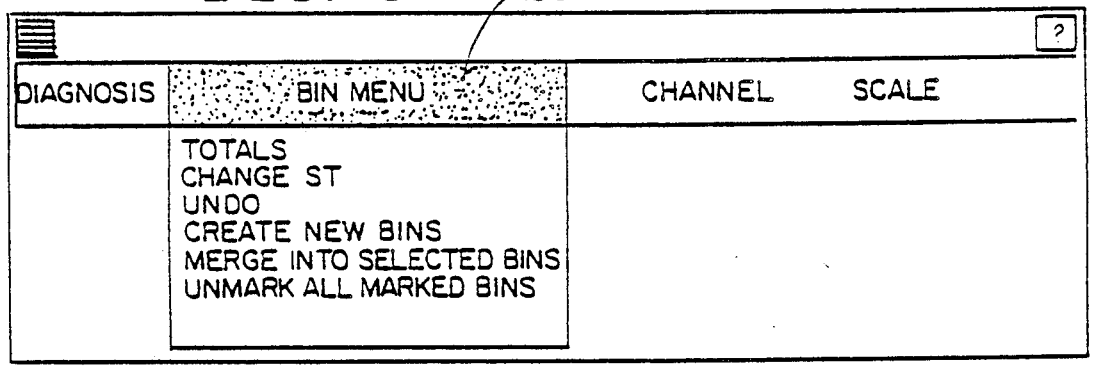
FIG. 9
FIG. 10
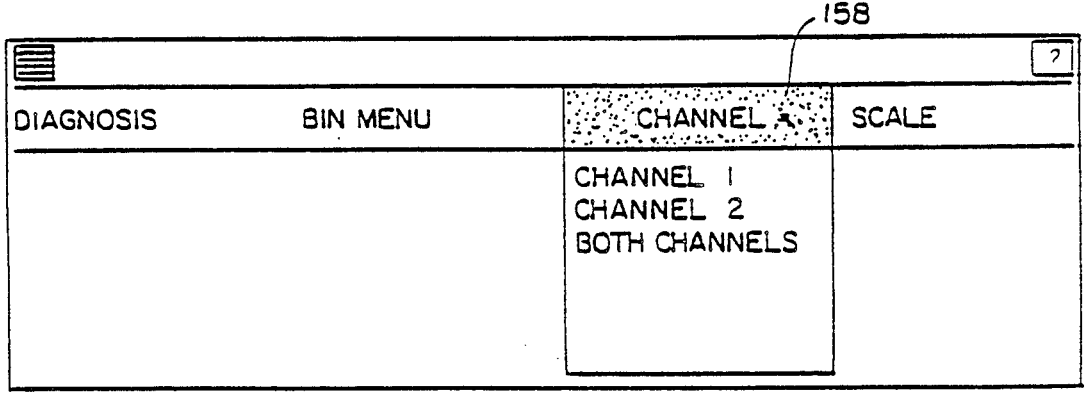
FIG. 11

| SCALE | CHANNEL | CALIPERS | OUTPUT | STATUS |
|---|---|---|---|---|
| | 184 | | | |
| | CHANNEL 1 | | | |
| | CHANNEL 2 | | | |
| | BOTH CHANNELS | | | |

FIG. 15

| SCALE | CHANNEL | CALIPERS | OUTPUT | STATUS |
|---|---|---|---|---|
| | | 200 | | |
| | 198 — LOCK CALIPERS | | | |
| | 202 — UNLOCK CALIPERS | | | |
| | 204 — REMOVE CALIPERS | | | |

FIG. 17

| SCALE | CHANNEL | CALIPERS | OUTPUT | STATUS |
|---|---|---|---|---|
| | | | 206  212 | |
| | | 208 — SAVE STRIP FOR REPORT | | |
| | | 210 — PRINT STRIP NOW | | |

HIGHLIGHTED BEAT STATUS

| | |
|---|---|
| BIN | XXX |
| DIAGNOSIS | XXX |
| PICKED ON CHANNEL | XXX |
| ST MEASURED ON CHANNEL | XXX |
| ST DEPRESSION (mm) | XXX |
| ST SLOPE (mm) | XXX |
| TIME OF OCCURRENCE | X-XX:XX:XX |

HIT ANY KEY TO RETURN

FIG. 20

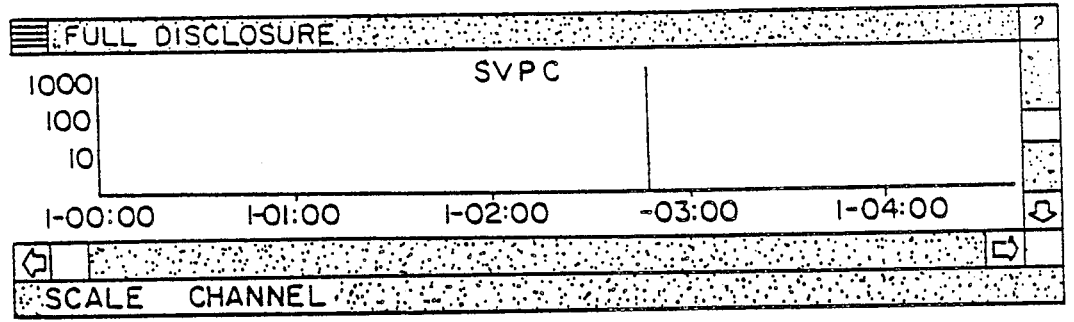
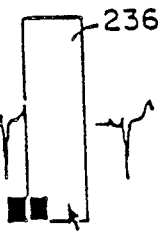
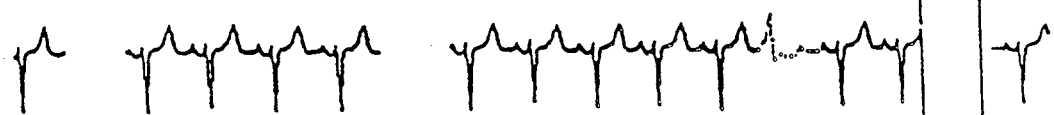
FIG. 23

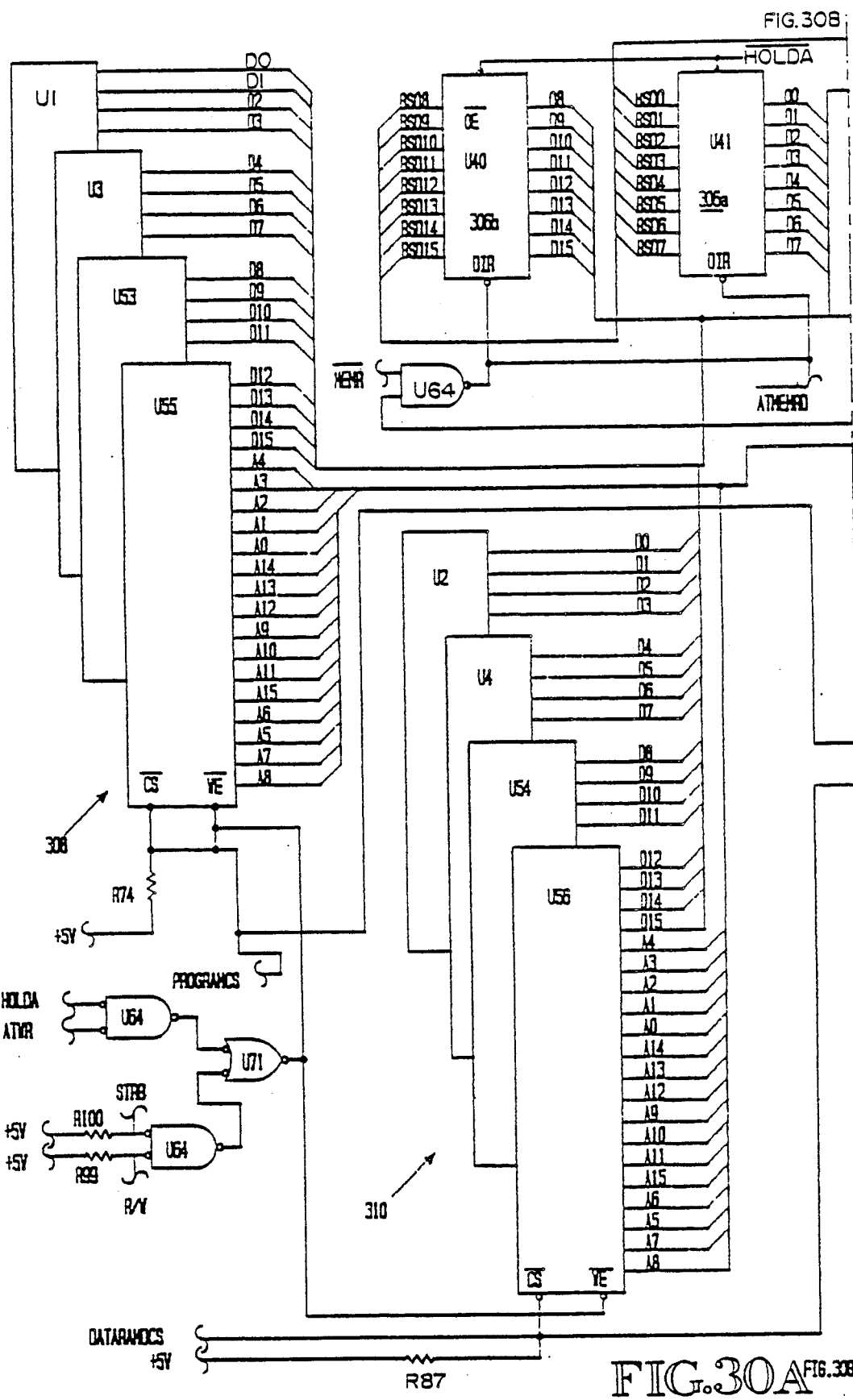

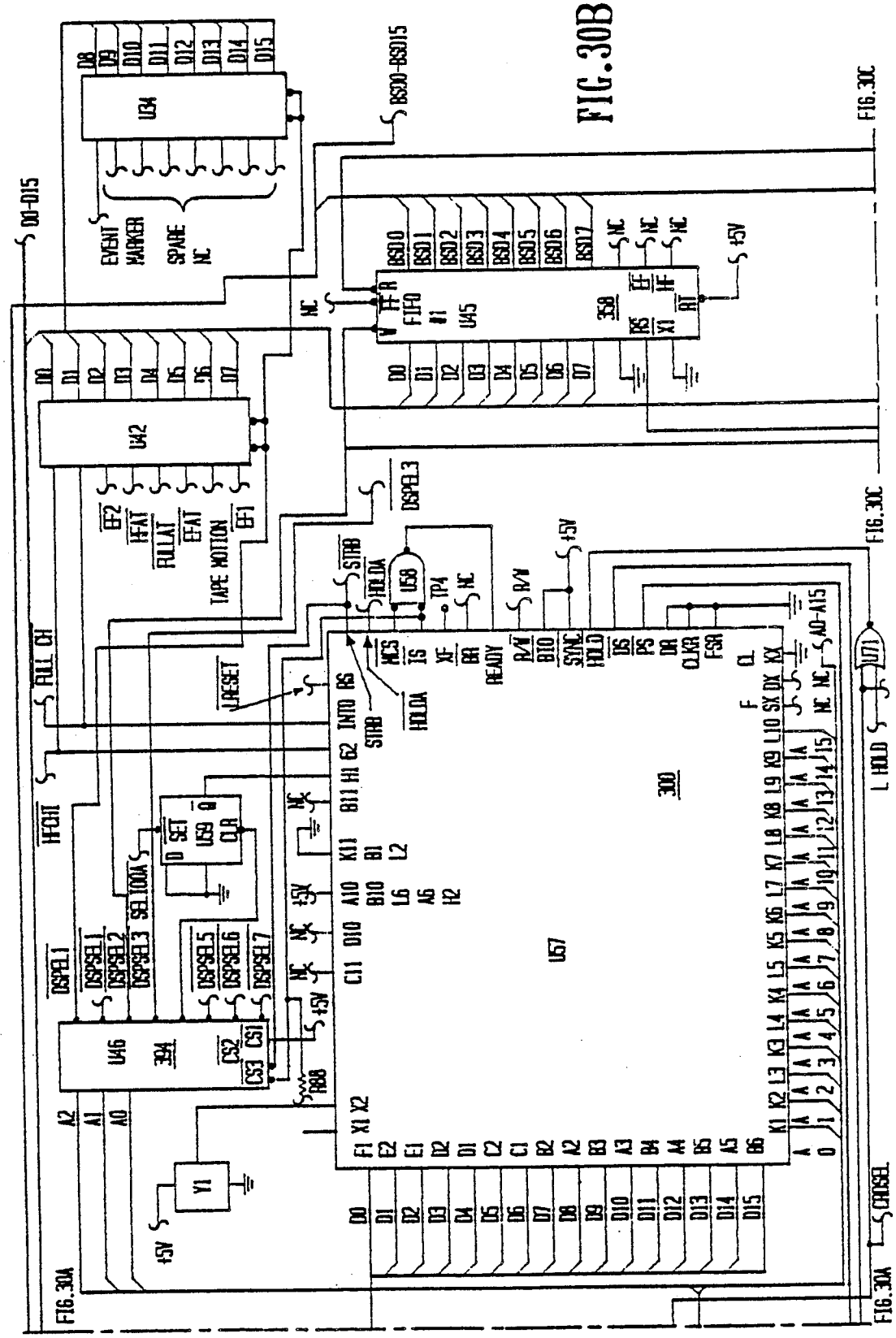

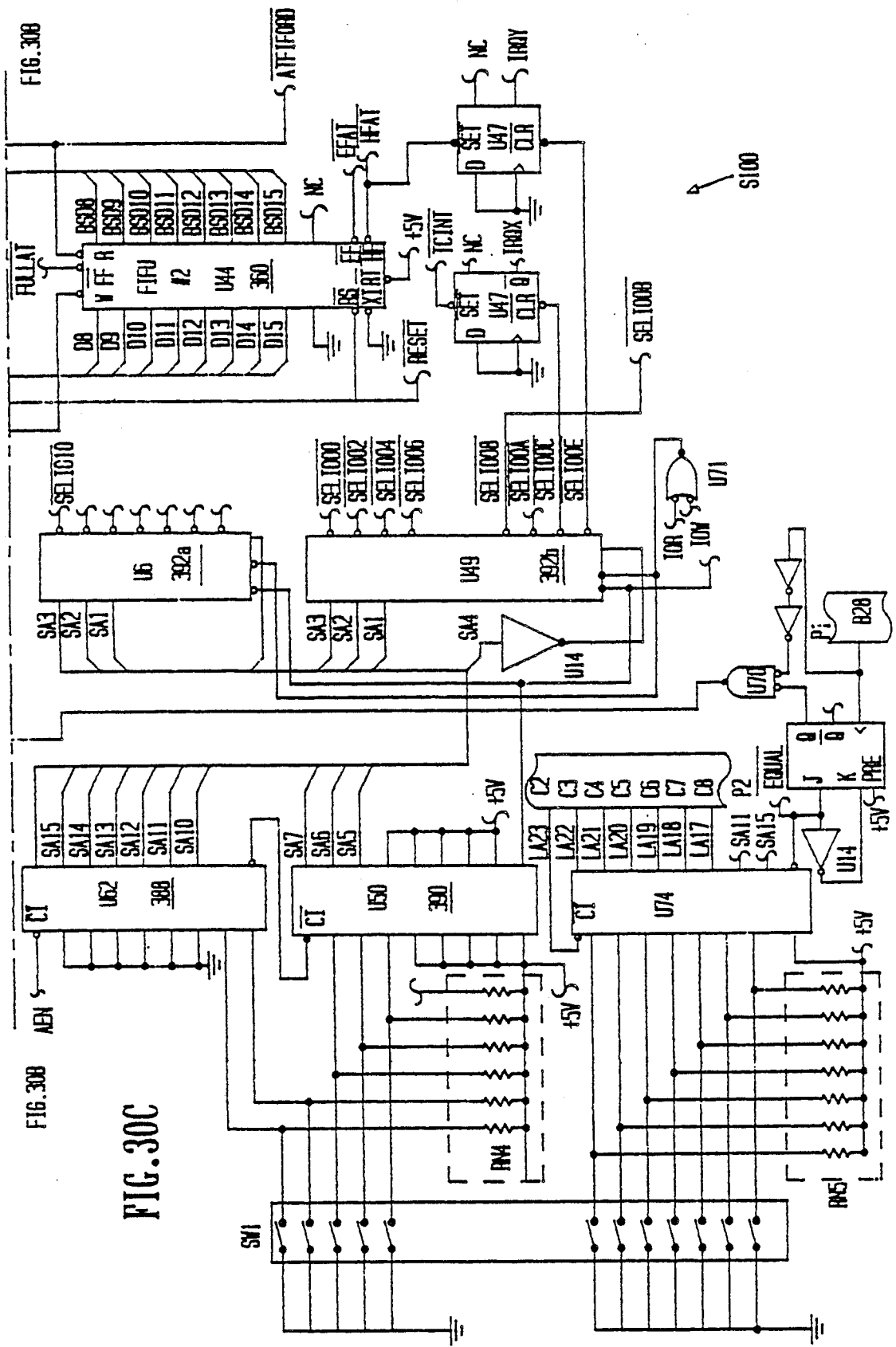

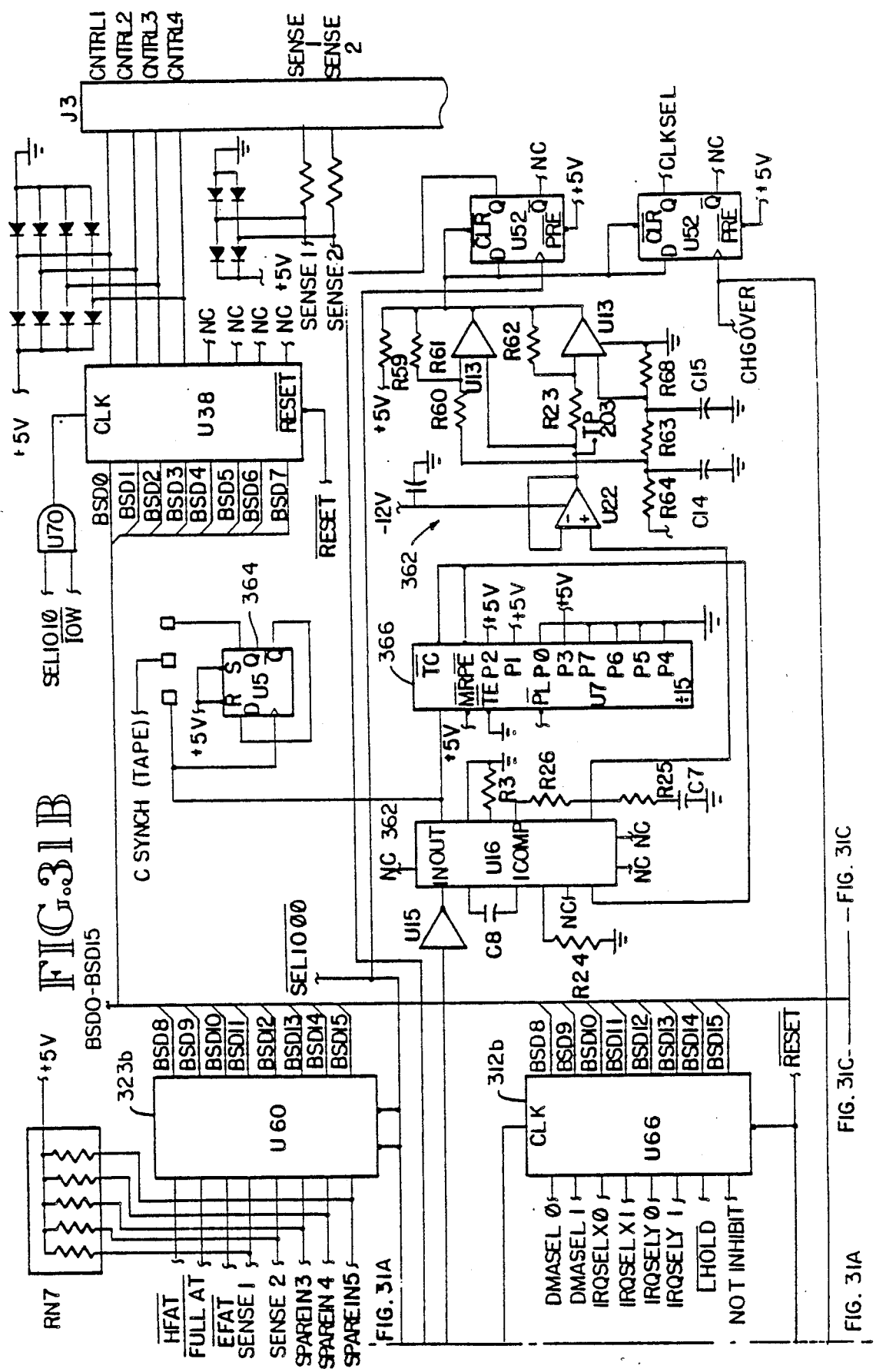

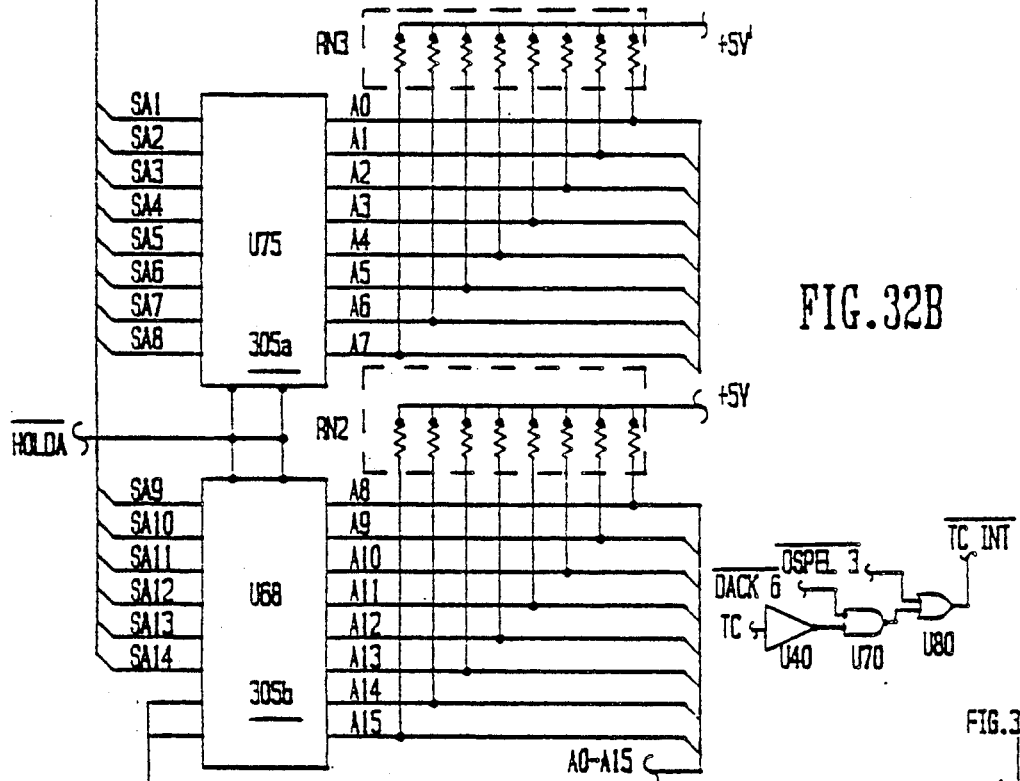
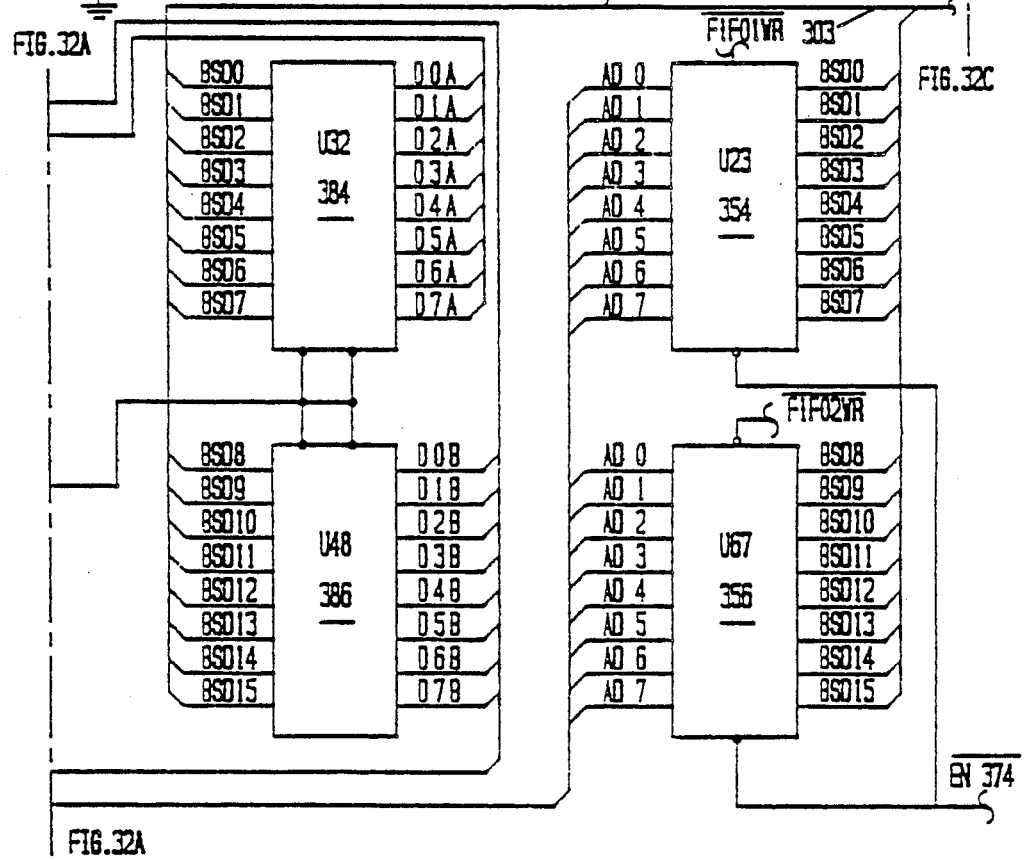
FIG. 32B

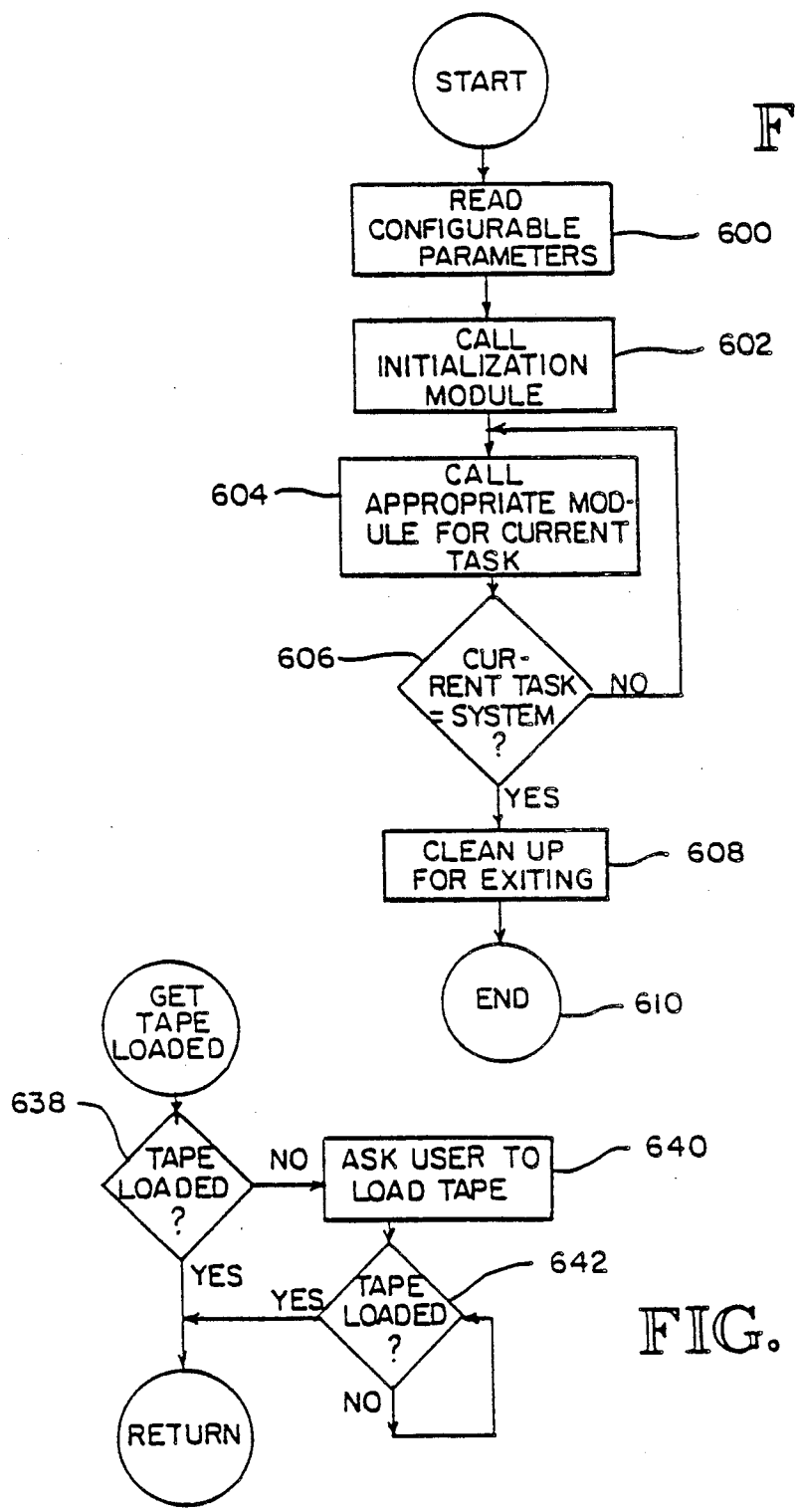

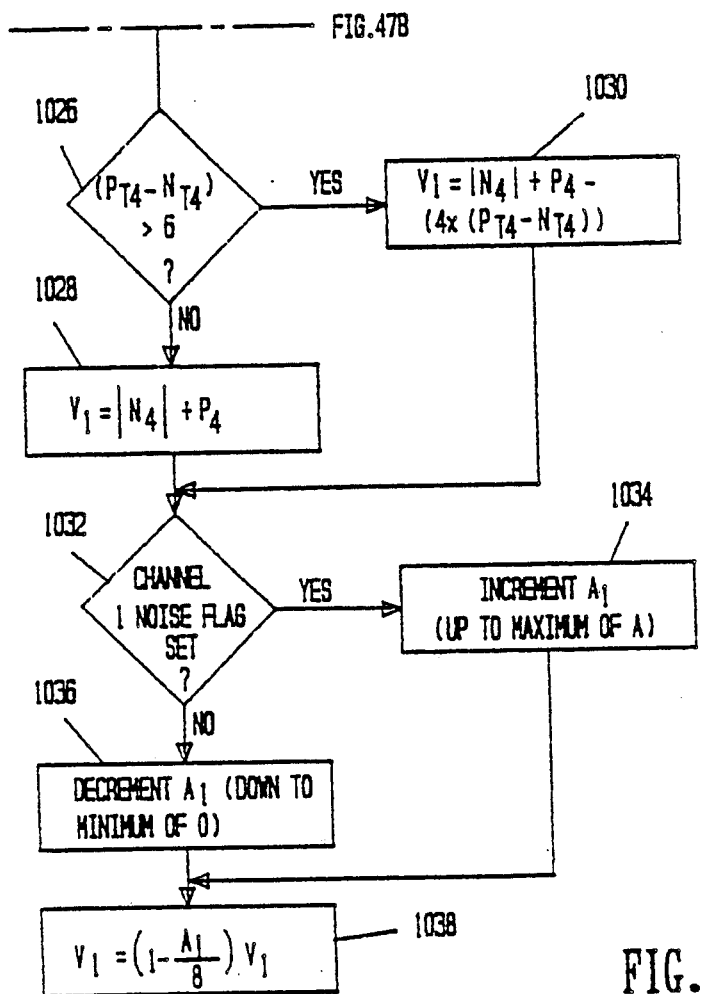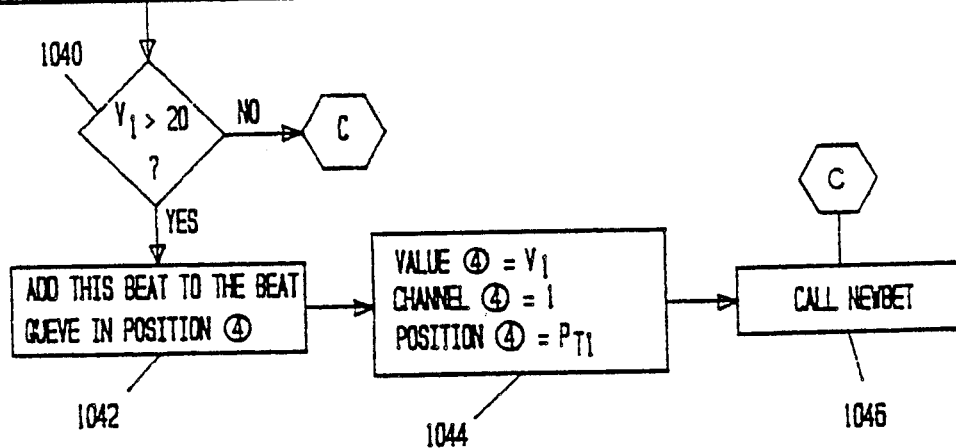
FIG.47C

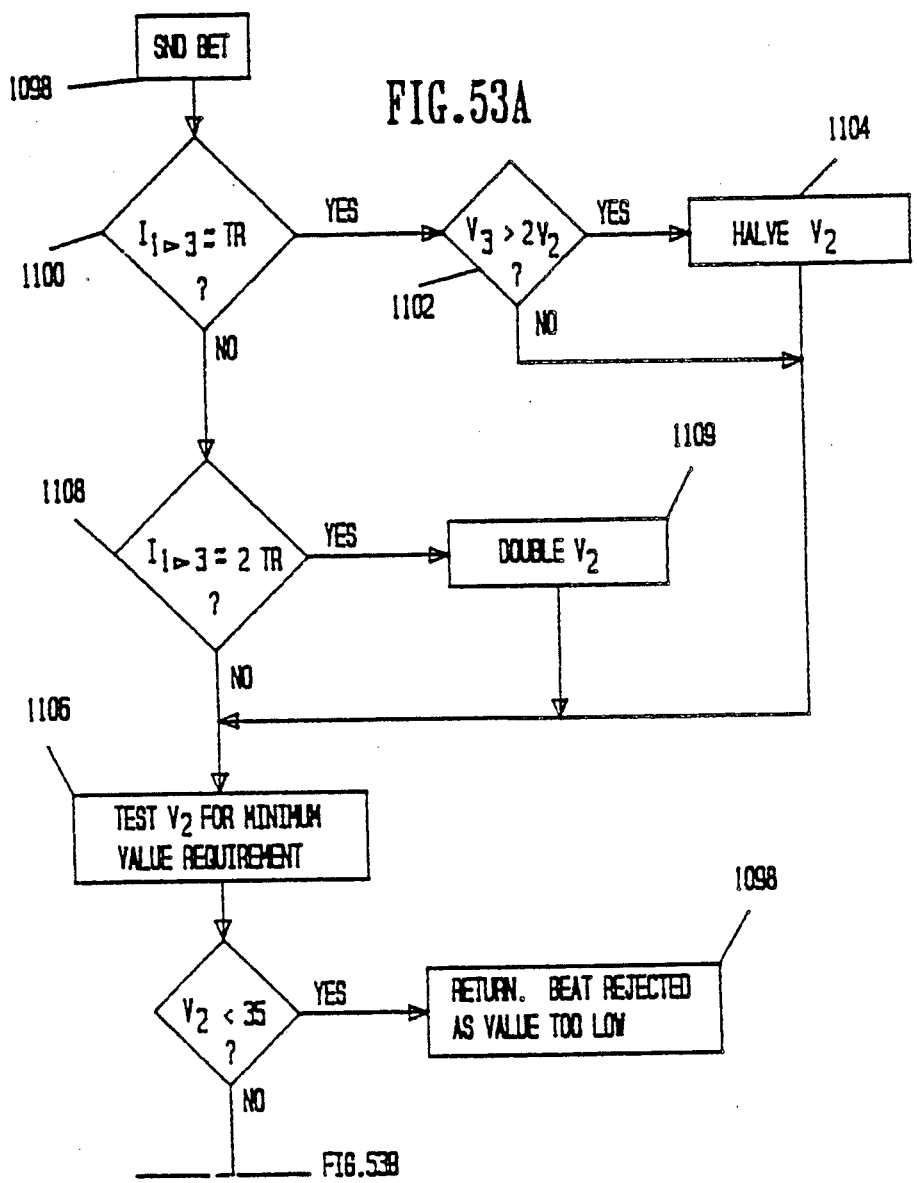

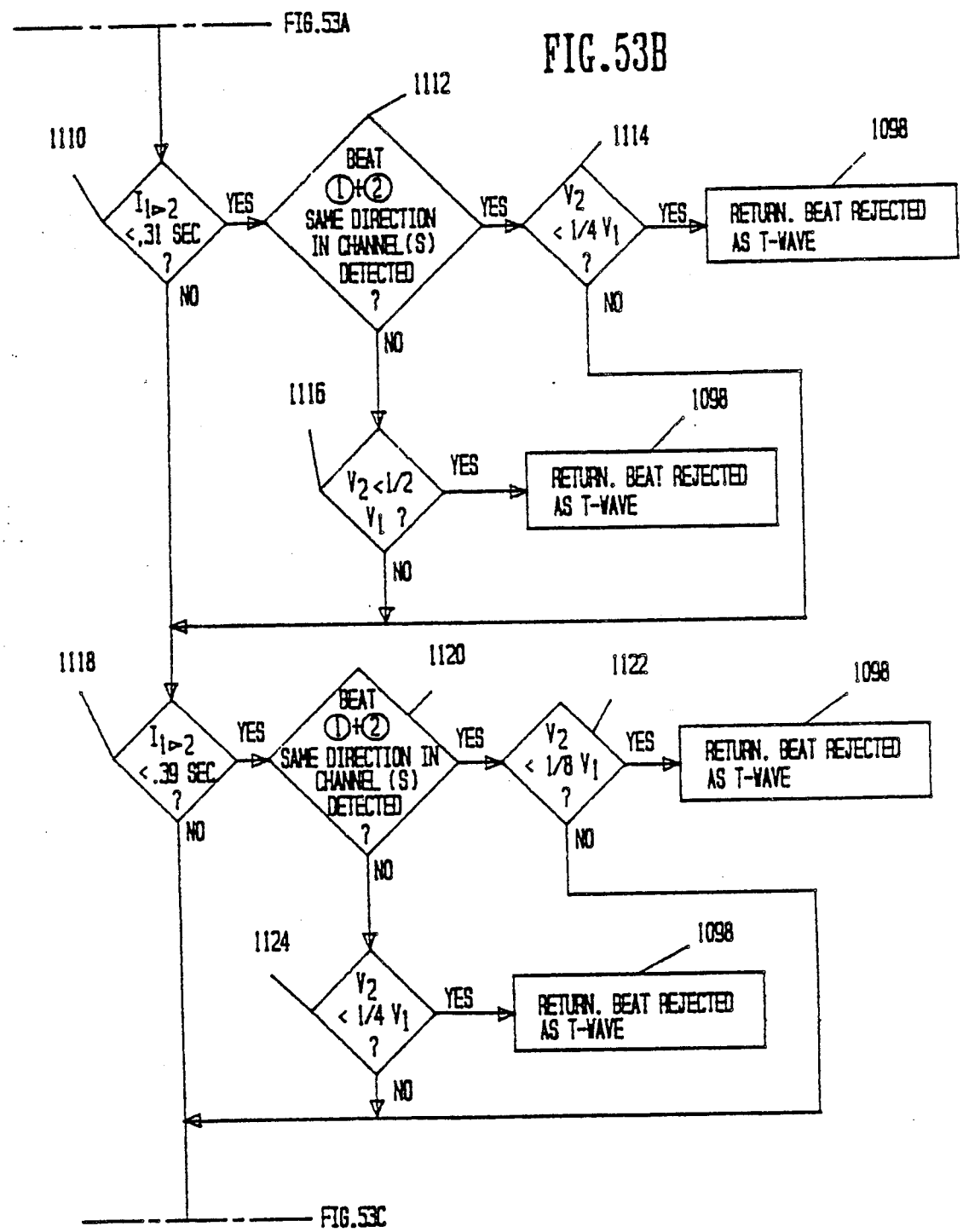

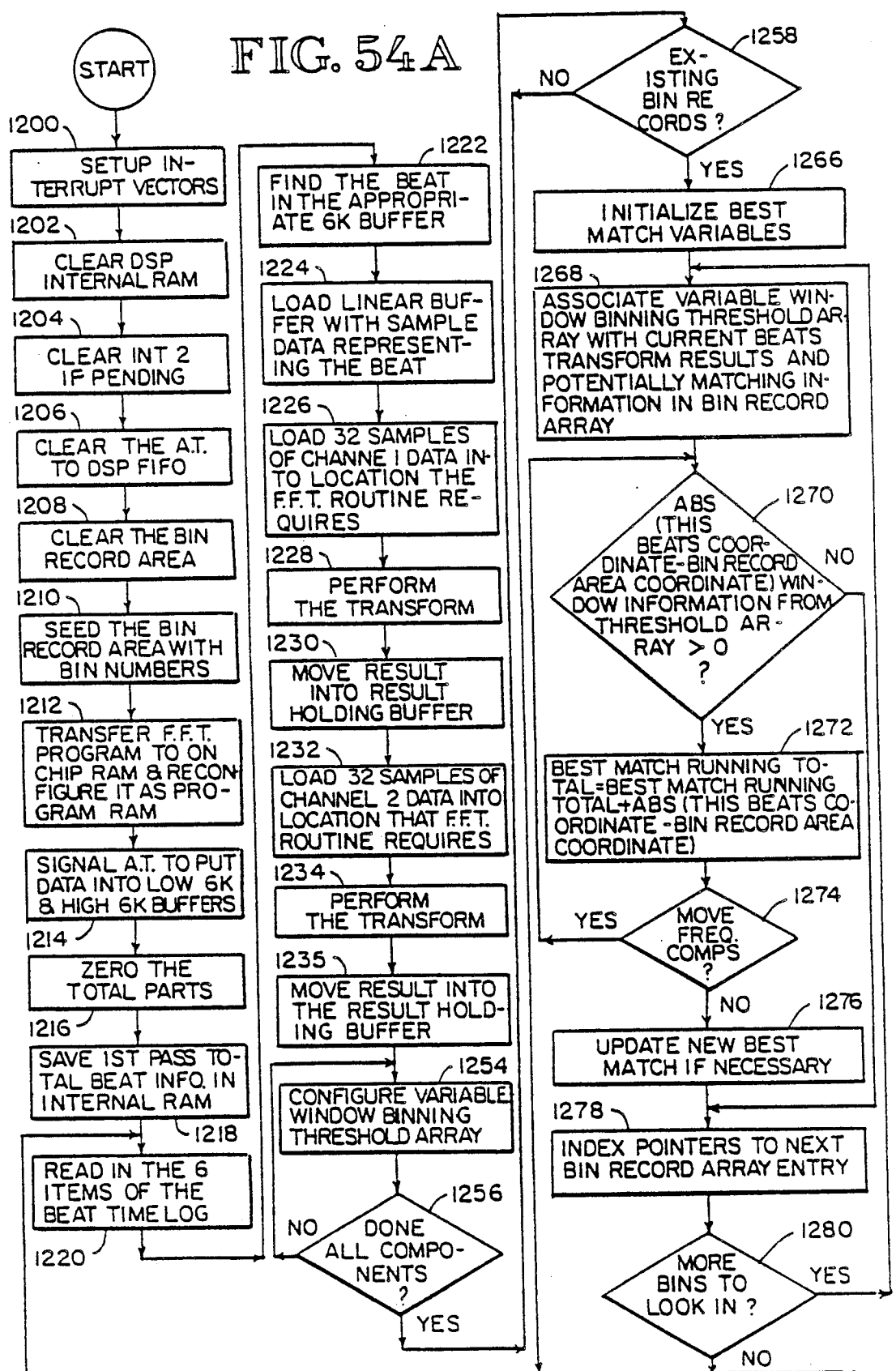

METHOD AND SYSTEM OF ECG DATA REVIEW AND ANALYSIS

TECHNICAL FIELD

This invention relates to ECG or Holter data review and analysis, and more particularly, to a method and system for improved review and analysis of such data.

BACKGROUND OF THE INVENTION

Electrocardiograms (ECG) are commonly used to generate data on the health and operation of a patient's heart. A number of electrodes are attached to a patient for an extended period, typically 12 to 48 hours, to measure the cardiac impulses of the patient. The resultant data can be graphed over time to create complex curves representing individual heartbeats. These beats can be reviewed, analyzed and categorized into normal and abnormal beats. This monitoring procedure, often referred to as Holter monitoring, is described in detail in a text entitled "Ambulatory Electrocardiography-Applications and Techniques" by Susan L. Horner, published by J. B. Lippincott Company, ISBN 0-397-50586-8, and references cited therein which are hereby incorporated by reference.

The Holter monitoring process generates too much data to be efficiently or effectively analyzed in real time. There simply is not time for clinicians or physicians to review 24 hours of data. As a result, computerized systems have been developed to aid clinicians n reviewing and analyzing Holter data. Existing systems, however, have not provided clinicians with flexible, efficient and accurate means to review and analyze Holter data.

DISCLOSURE OF THE INVENTION

It is an object of the present invention to provide an improved method and system for ECG data review and analysis.

It is another object of this invention to provide such a method and system allowing improved categorization of heartbeats.

It is another object of this invention to provide such a method and system allowing flexible and efficient operation.

It is another object of this invention to provide such a method and system allowing a clinician/user to quickly and easily recategorize beats.

It is another object of this invention to provide such a method and system allowing improved superimposition review, including P-wave indicia, color coding, and audio information.

It is another object of this invention to provide such a method and system providing the clinician/user with j access to real-time information when reviewing individual beats.

It is another object of this invention to provide such a method and system which allow a clinician/user to obtain quantitative information regarding individual beats using improved calipers.

These and other objects of the invention, which will be apparent as the invention is more fully described below, are obtained by providing, in preferred embodiments, a computerized system for ECG data review and analysis. A transformation analysis is performed on beat data and the transformed data are categorized into beat "bins." The clinician/user may select sensitivity to vary the number of bins created by the system. Once beats are preliminarily assigned to bins by the system, the clinician/user may review beats by bin and reassign beats as desired. In preferred embodiments, recategorization is accomplished by "dragging" a beat to a new bin with the aid of a pointing device or "mouse." In preferred embodiments, a Superimposition mode allows dynamic review of beat graphs with automatic detection, color coding, and optional pause at abnormal beats. Audio information is also preferably provided to aid the clinician/user in detecting abnormal beats. A P-wave marker capability is also provided to give a constant reference point during beat review in the Superimposition mode.

In another aspect, the invention provides a method for categorizing ECG data which contains a plurality of heartbeat waveforms, each waveform having a predetermined feature. The method comprises the steps of (a) sampling the data, (b) detecting the occurrence of the predetermined feature in the sampled data and identifying each of the waveforms containing the predetermined feature, (c) selecting each portion of the ECG data having a predetermined relationship to the predetermined feature of each of the waveforms, and (d) performing a transformation of each of the data portions and producing a sequence of samples of the transformed portions. The method further comprises the steps of (e) categorizing each sequence of samples of the transformed portions into one of a plurality of bins, and (f) identifying each of the sampled portions of ECG data with the bin into which the corresponding transformed portion is categorized.

Preferred embodiments also provide the clinician/user immediate access to surrounding real-time data when reviewing individual beats.

BRIEF DESCRIPTION OF THE DRAWINGS

FIG. 1 is a schematic diagram of the hardware components of a preferred embodiment of the present invention.

FIG. 2 is a screen display of the Main Menu of the software system comprising a portion of the preferred embodiment of FIG. 1.

FIG. 3 is an illustration of the Tape Analysis Options screen which appears when the Tape Analysis command of FIG. 1 is actuated.

FIG. 4 is an illustration of a screen display for the system during initialization of the R, ISO, and ST reference measurements for the system.

FIG. 5 is a patient information screen.

FIG. 6 is a Patient Diary Entry Form screen issued by the system of FIG. 1.

FIG. 7 is an illustration of the Bin Review Menus with the Diagnosis Menu actuated.

FIG. 9 is an illustration of a screen display for the Bin Review Menus with the Bin Menu actuated.

FIG. 10 is an illustration of the Totals box from the Totals Command within the Bin Menu of FIG. 9.

FIG. 11 is an illustration of the Bin Review Menus with the Channel Menu actuated.

FIG. 15 is an illustration of the Bin Review Menus from the lower portion of the Bin Review Screen of FIG. 8 with the Channel Menu actuated.

FIG. 17 is an illustration of the Bin Review Menus of the lower portion of the Bin Review Screen with the Calipers Menu actuated.

FIG. 18 is an illustration of the Bin Review Menus of the lower portion of the Bin Review Screen with the Output Menus actuated.

FIG. 20 is an illustration of the screen display generated by the Highlighted Beats Status command of the Status Menu from the lower portion of the Bin Review screen.

FIG. 23 is an illustration of a Full Disclosure screen illustrating the box enclosing beats as the cursors move over the ECG waveforms in the lower portion of the screen display.

FIG. 30A is a detailed schematic diagram of a first part of a first portion of the digital signal processing board of the present invention.

FIG. 30B is a detailed schematic diagram of a second part of a first portion of the digital signal processing board of the present invention.

FIG. 30C is a detailed schematic diagram of a third pat of a first portion of the digital signal processing board of the present invention.

FIG. 31B is a detailed schematic diagram of a second part of a second portion of the digital signal processing board of the present invention.

FIG. 32B is a detailed schematic diagram of a second part of a third portion of the digital signal processing board of the present invention.

FIG. 34 is a flow chart illustrating the operation of the Main Module in a preferred embodiment of the invention.

FIG. 35 is a flow chart illustrating the operation of the Get Tape Loaded Routine of the preferred embodiment of the invention.

FIG. 47C is a third portion of a flow diagram of the DETECT module of the digital signal processing chip software.

FIG. 53A is a first portion of a flow diagram of the SNDBET subroutine of the digital signal processing chip software.

FIG. 53B is a second portion of a flow diagram of the SNDBET subroutine of the digital signal processing chip software.

FIG. 54A is a first portion of a flow diagram of the binning module of the digital signal processing chip software.

DETAILED DESCRIPTION OF THE PREFERRED EMBODIMENTS

I. System Overview

Figure 8:
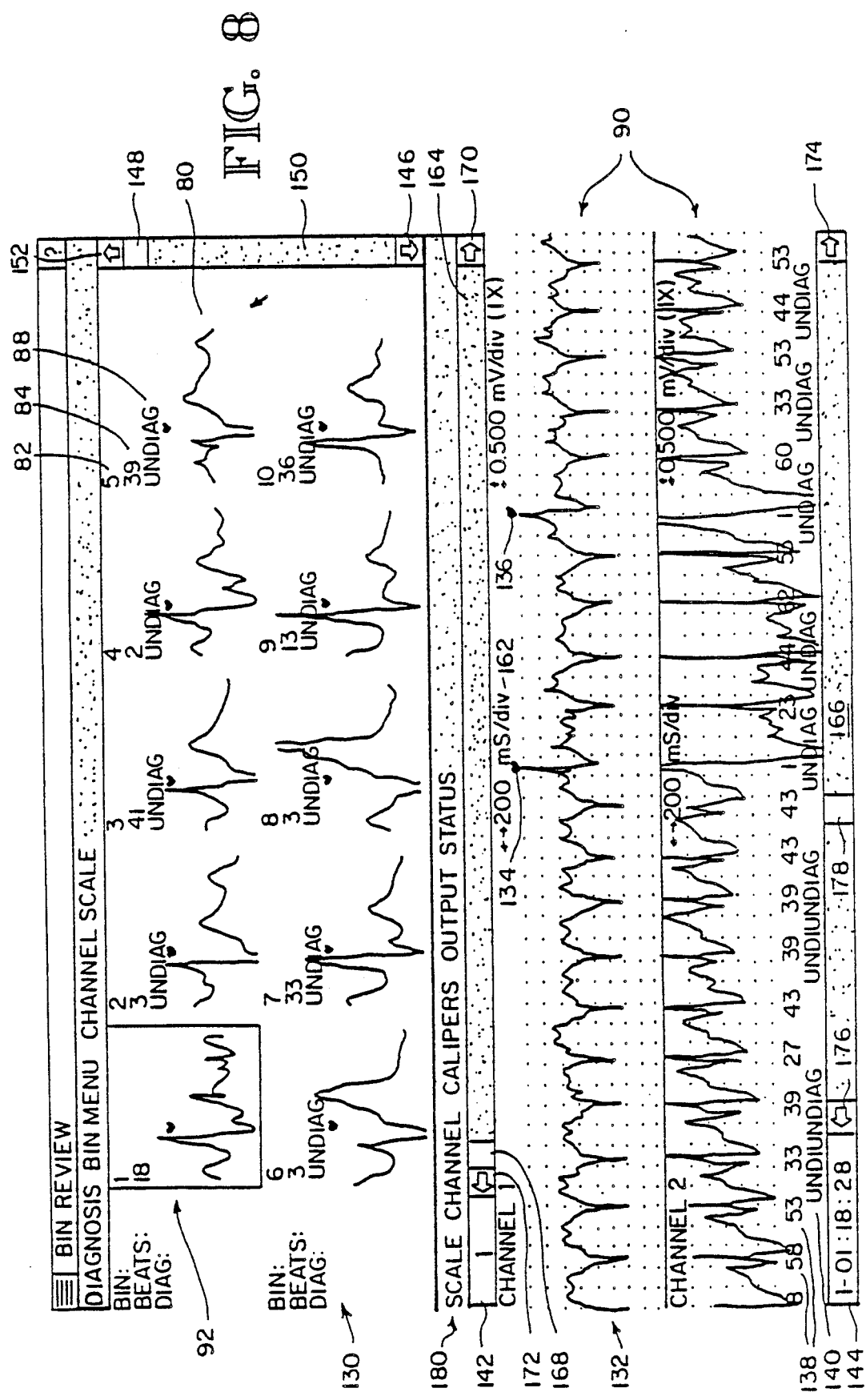
FIG. 8 is an illustrative screen display in the Bin Review mode of the system of FIG. 1.

The present invention is preferably implemented on a microcomputer-based system, although it is appreciated that alternate implementations of the invention are possible and would work equally well. For convenience and understanding, the methods and systems of the present invention will be described in this section with respect to a preferred embodiment on an IBM AT or IBM AT-compatible personal computer. Holter or ECG data stored on tape using known machines is transferred to a microcomputer system where the data is automatically analyzed and categorized in accordance with the invention and presented to the system user for further review, analysis and recategorization as necessary. Improved methods of automatic categorization, review and analysis of Holter data provide flexibility, efficiency and speed not found in prior systems.

A schematic diagram of the hardware components of a preferred embodiment is contained in FIG. 1. An IBM AT-compatible microcomputer 60 includes a main processor subsystem 62 and a coprocessor subsystem in the form of a custom Digital Signal Processing (DSP) board 64 installed in one of the expansion slots of the microcomputer. The microcomputer is operably connected to a standard display screen 66, a standard AT-compatible keyboard 68, a three-button mouse 70, such as the Model C7 3F-9F Mouse, manufactured by Logitec Corporation of Fremont, Calif., and a laser printer 72, such as the LBP II, manufactured by Canon U.S.A., Inc., of Lake Success, N.Y. The main processor subsystem runs under the MS-DOS Version 3.1 operating system from Microsoft Corporation of Redmond, Wash., and includes 2 Mb of expanded RAM 71 (manufactured by Boca, Inc., of Boca Raton, Fla.) and a 22 Mb hard disk storage device 73 installed therein. The main processor subsystem of the preferred embodiment also includes printer cards and drivers therein. Included among these is a standard parallel and serial communication card, manufactured by Wyse Technology of San Jose, Calif.; a J Laser SA laser printer driver card (installed in the laser printer), made by Tall Tree Systems of Palo Alto, Calif.; and a Vega 7 expanded graphics adapter, manufactured by Video Seven of Fremont, Calif.

The preferred embodiment described herein is designed to accept Holter data from an ECG tape source 74, such as the SpaceLabs 90201 Holter Recorder from SpaceLabs, Inc., of Redmond, Wash., or an ICR 7200 Holter Recorder from the Instruments for Cardiac Research, Inc., of Liverpool, N.Y. An open reel tape drive can also be added to the system to accept input from tapes produced by Del Mar Avionics of Irvine, Calif., or similarly produced tapes. Two channels of ECG data and corresponding clock data are transferred from the tape to an analog-to-digital converter (A/D) 76 on the DSP board. Digitized data is sent to the main processor hard disk as well as to a microprocessor 76 on the DSP board. On the DSP micro-processor, the digitized data undergoes a raw data filtering in the form of a beat detection and noise detection procedure. After filtering, the data undergoes a binning analysis on the DSP processor using the improved Fast Fourier Transform (FFT) methods of the present invention to categorize the beats into different bins. Once categorized, the beats may be reviewed by the system user as described in the User Interface section below.

To print reports on the laser printer, the selected report data undergoes rasterization using a rasterization procedure that operates on the DSP processor.

II. User Interface

A. Overview

In the preferred embodiment, analysis software uses menus and prompts to guide a clinician/user through ECG data processing, analysis, review, and report generation. The software analyzes the Holter recording, while the clinician enters patient identification information and other data recorded by the patient in a diary. Two-channel ECG data from the tape is digitized and then analyzed by the DSP processor and transferred simultaneously to the main processor subsystem's hard disk. As the data is digitized, the software diagnoses each heartbeat by morphology and groups together beats with similar morphologies into classes, called "bins." The clinician can vary the binning sensitivity, change the diagnoses assigned to any bin by the system, and move individual beats from bin to bin.

After information from a tape is analyzed, the three main software functions are accessible. These are: Bin Review, Full Disclosure and Superimposition.

1. ECG Bin Review

When tape analysis is complete and the patient information has been entered, the ECG Bin Review phase begins. As illustrated in FIG. 8, representative beat 80 from each bin, or category of beats, is displayed on the computer screen with the following information: a chronological number 82 identifying each bin, the total number of beats 84 in each bin, and the bin diagnosis 88. From on-screen menus, the user can:

change the diagnosis of any bin;

merge bins;
create new bins; and
display the representative beat in one or two channels.

Waveform displays 90 appear simultaneously on the lower half of the screen. They are six-second real-time strips displaying the first beat of the highlighted bin 92 in the center of the strip. With this function, the user can:
- scan each beat in the bin;
- make measurements on beats with on-screen calipers;
- move beats from bin to bin;
- save a six-second strip for inclusion in the printed ECG report, or print the strip immediately; and
- determine the time, and any other parameter, of any given event or beat.

2. Full Disclosure

Figure 19:
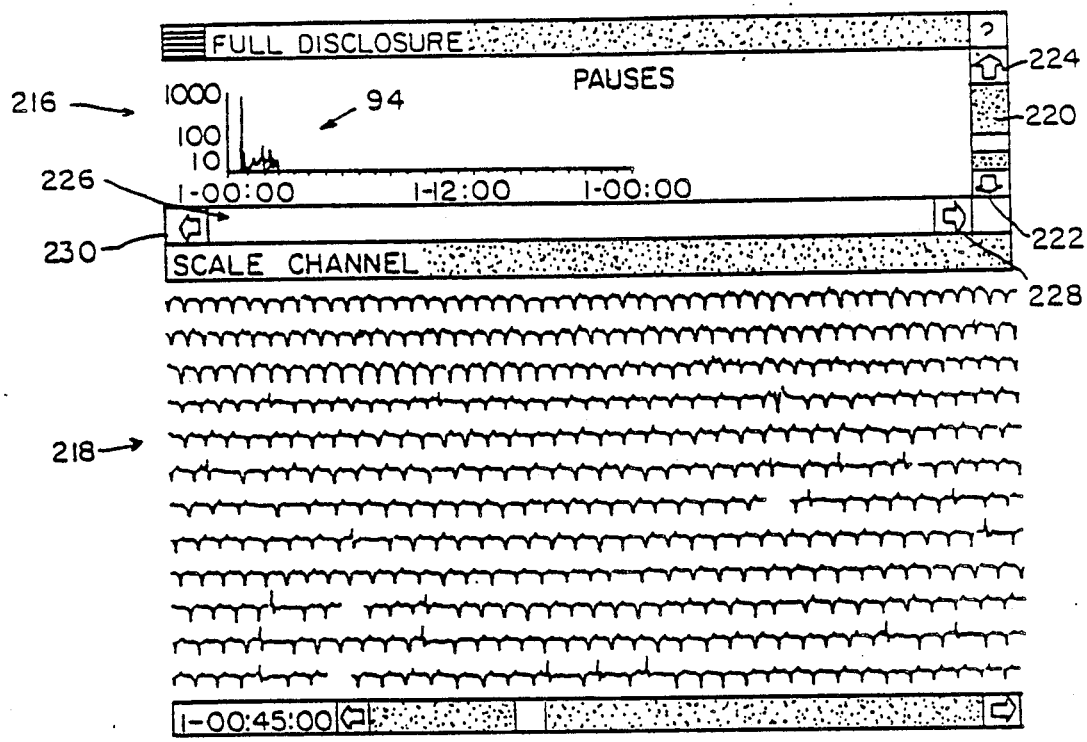
FIG. 19 is an illustration of a Full Disclosure screen.

When the Bin Review process is complete, the Full Disclosure function provides a recap of the information, as illustrated in FIG. 19. Bar graphs, called "histograms," illustrate the following information for the entire 24-hour period:
- frequency and time of each type of abnormal heartbeat;
- ST deviation from isoelectric line, and ST slope;
- distance between R-waves;
- heart rate; and
- patient-initiated event markers.

Furthermore, any point on the histogram can be selected, and the ECG waveform for that segment of tape can be viewed in its entirety.

3. Superimposition

Figure 27:
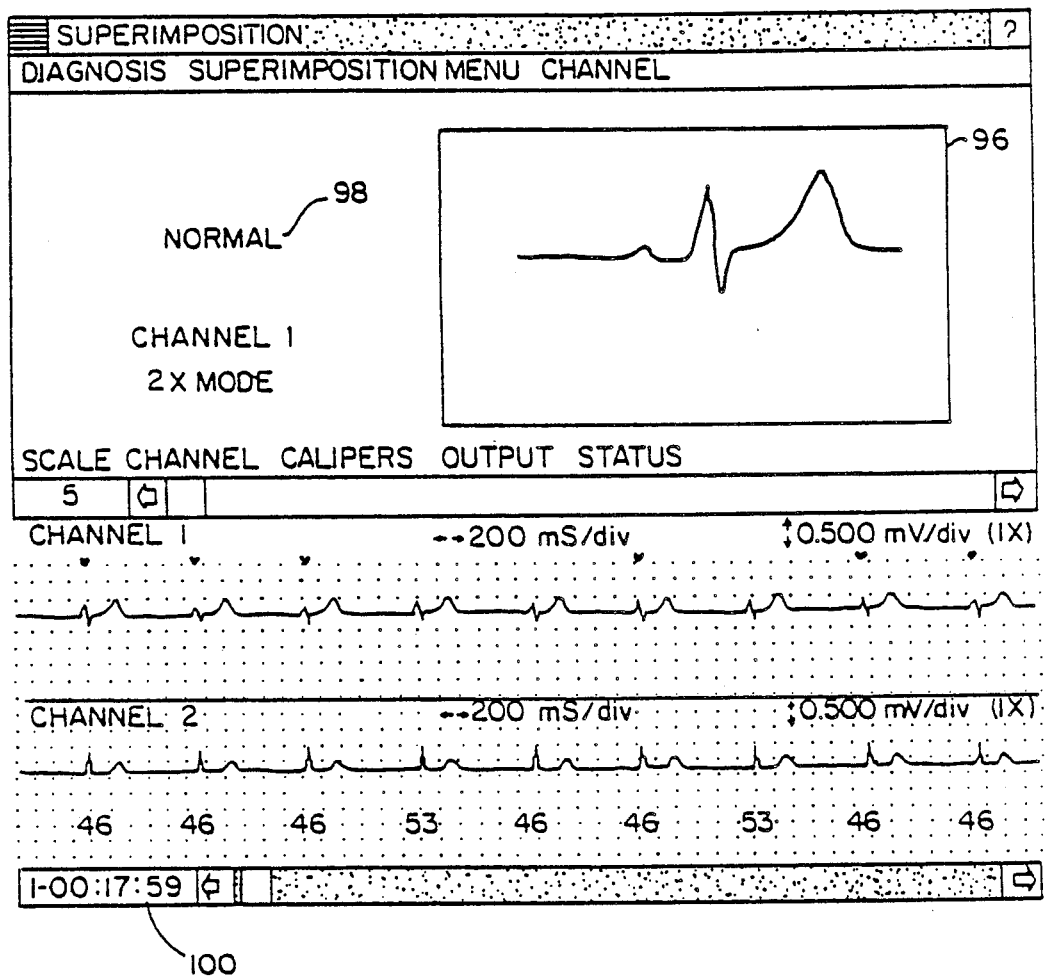
FIG. 27 is an illustration of the screen display in the Superimposition Mode, with real-time data displayed at the bottom of the screen.

Every beat on the tape is flashed on the screen in rapid succession in the Superimposition mode. A sample display screen from the Superimposition mode is illustrated in FIG. 27, including a beat display area 96. A slight pause accompanies abnormal beats to allow the clinician to freeze the screen in order to view and analyze the beat. Once the screen is frozen, the beat's diagnosis 98 and time of occurrence 100 are displayed.

A preferred embodiment uses audio-visual superimposition with color coding of abnormals. This feature allows the user to use both auditory and color-enhanced visual cues in identifying arrythmias.

4. Comments, Interpretation and Print ECG Report

Screens are provided for clinician comments and physician interpretation to be typed in for inclusion in the printed ECG report.

The Print Report function allows the user to print all, or selected portions, of the data. A full report includes:
- patient identification information;
- patient diary information;
- ECG summary
- hour-by-hour tabulations
- all six-second strips saved for report;
- all histograms;
- full disclosure ECG waveforms;
- comments; and
- interpretation.

When the operator exits the Holter Analysis program, the file of ECG data and the report file are stored on the main processor subsystem's hard disk.

B. Using the System

All software functions are initially accessed through the Main Menu 102, illustrated in FIG. 2. The user may return to the main menu at any time by selecting the main menu icon 104—which appears in the upper left-hand corner of the program screen at all times. Function control is provided through the mouse 70, and data is entered by keyboard 68.

In the preferred embodiment, a mouse controls the cursor in a known manner. A three-button mouse (eft, center and right) is used in the preferred embodiment. The right button 106 is used for beat editing and bin merging. The center button 108 is used for making measurements. The left button 110 is used for all other functions.

The keyboard is used to enter and edit information on the patient information forms, and commentary and interpretation pages. It is also used to enter identifying information where requested by the system.

A Help icon 112 appears in the upper right-hand corner of the program screen during operation. The Help icon calls a Table of Contents (not shown) which lists, in chronological order, the topics available within the Help file. A scroll bar (not shown) appears to the right of the Help screen to enable the user to move through the test to find the needed information.

C. Holter Analysis

1. Prepare for Holter Analysis

Before starting the Holter Analysis program, the users should have a twenty-four-hour, two-channel Holter recording and a corresponding patient diary or information sheet. The various components of the system are turned on as necessary and the patient's Holter recording tape is fed into the tape drive. The Main Menu is displayed on the program screen, allowing the user to select the various options described below.

2. Tape Analysis Options

The user selects "Tape Analysis" from the Main Menu to process a tape, causing the screen of FIG. 3 to be displayed. From this screen, the user must select the following options:

Erase Patient Information: When data is read from a tape, it is stored on the main processor subsystem's hard disk. To analyze data from a new patient tape, the user must select select YES, which erases data from a previous tape. NO is selected to review data from the previous tape.

Erase Report Commentary: To enter commentary from a new patient tape, the user must select YES, which erases the commentary from a previous tape. NO is selected to review or revise the commentary from a previous tape.

Measure ST on Channel: The user selects the channel from which the ST measurement is taken.

Analyze Beats on Channel: The user selects one or both channels for beat analysis.

Tape Machine: Select cassette or reel-to-reel.

Binning Sensitivity: A high binning sensitivity will detect very minor differences in beat morphology and create separate bins for each morphology. A low binning sensitivity will detect gross differences in beat morphology and create fewer bins. In the preferred embodiment, the user selects one of five preselected sensitivity levels. Using a low binning sensitivity can result in missed diagnoses of beat morphologies. A nominal setting of 4 is recommended.

When the user is satisfied with the selected Tape Analysis Options, "Accept" is selected.

If the user selects YES for Erase Patient Information, the system prompts the user to insert a tape in the tape drive, if the user has not yet inserted a tape. The system automatically rewinds the tape and determines tape gain settings (amplitudes of waveforms). This message is displayed: "Gathering data for adjusting gain settings." As the system scans the waveforms for representative beats, sections of waveforms appear on the screen at periodic intervals.

3. Set R, ISO, and ST Reference Measurements

After the gain setting is adjusted, representative beats 114 are displayed on the screen, as illustrated in FIG. 4. If the user is not satisfied with the channel selected to measure ST, the user can change it at this point.

a. Change ST Channel

A menu line 116 is displayed directly above the waveform display. The Channel Menu 118 (shown in deactivated position) allows the user to change the channel on which the ST measurement is made. To change the channel, the user moves the cursor (which now appears as a cross hair) to the Channel Menu and holds down the left mouse button. The channel not currently displayed on the screen appears on the menu in bold face. The user can select it by moving the cursor over it and releasing the left mouse button.

b. Select Representative Beat

To enable the user to select a representative beat, a dialog box (not shown) appears on the screen of FIG. 4 with the message, "Is this data acceptable for setting ST measurement points?" with YES and NO boxes for response.

If the beats are not acceptable, the user selects NO. The tape rewinds and new beats for reference measurements are displayed. The user selects YES if the beats are acceptable, and a dialog box (not shown) with the message "Pick R wave of representative beat" is displayed. In addition to this message, a cross hair appears on the screen in place of the cursor. The mouse controls movement of the cross hair.

c. Set Reference Points

The user must select which beat will be used for all of the reference measurements: R, ISO, and ST. The user moves the cross hair on the screen so that it is positioned on the R-wave of choice. The user then clicks the left mouse button once, and a vertical line 120 appears in place of the cross hair. The R-wave measurement is now established.

This message is displayed in a dialog box (not shown): "Pick point to measure isoelectric point for this beat." Again, a cross hair appears on the screen. The user moves the cross hair to the position to be used for the reference isoelectric (ISO) point and clicks the left mouse button once. A vertical line 122 appears in place of the cross hair. The isoelectric measurement is established.

To set the ST point, a dialog box (not shown) with the message "Pick point to measure ST for this beat" is displayed on the screen. The user must move the cross hair which appears on the screen to the point desired for measuring the ST segment. The user clicks the left mouse button once and the ST measurement is established by a third vertical line 124. FIG. 4 illustrates an example of established reference measurements for R, ISO, and ST.

After the user has established all reference measurements, a dialog box 126 appears on the screen asking the user, "Are the ST settings acceptable?" with YES and NO boxes for response. If the user selects YES, the message "Tape Rewind in Progress" is displayed. When the tape is rewound, the following message appears on the screen: "Tape Playback in Progress XXXX beats Tape Time: X-XX:XX:XX." If the ST settings are not acceptable, the user selects NO to repeat the entire "Setting R, ISO, and ST Reference Measurements" sequence described above.

After the R, ISO, and ST reference measurements are set, the system reviews the data with the established reference measurements. The message "Tape Analysis in Progress" appears in the upper right corner of the screen. A Patient Information Screen, as illustrated in FIG. 5 and described below, automatically appears. A series of beeps indicates the tape has completed analysis, and the message "Tape Analysis Complete" appears in the upper right corner.

D. Enter and Edit Patient Information

Patient information is entered into the system via the keyboard on the Patient Information Entry Form, illustrated in FIG. 5, and the Patient Diary Entry Form, illustrated in FIG. 6. The two forms appear on the screen automatically during tape analysis. They can also be displayed at any other time by selecting Patient Information from the Main Menu. The patient information is included as part of the printed ECG report.

The Patient Name field is highlighted when the Patient Information Form appears. The user enters information by using the keyboard. No more information can be entered than will fit in the provided fields. After entering information in a field, the user presses the Enter or Return key to move to the next field, which now appears highlighted. To enter or edit information in a field out of sequence, the user selects that field with the left mouse button. The backspace key is used to erase information.

The user must press the End key to move to the Patient Diary Entry Form, or press Enter or Return when the last field on the Patient Information Entry Form is complete.

E. Patient Diary Entry Form

Data from the patient's diary is used for data to enter in the Patient Diary Entry Form, which appears below the Patient Information Entry Form on the screen.

The user enters the time the Holter tape recording was started. If no time is entered on the first line, the system automatically assigns midnight (00:00) as the start time. When the screen appears, only the first line of the form is visible. Once data is entered on the line, the user presses the Enter or Return key to display a new line. Five lines can appear on the screen at one time; when the bottom line is filled and the Enter or Return button is pressed, the form scrolls up to reveal another blank line, up to seventy-five total lines. The top line of data scrolls out of view.

The scroll bar 128 to the right of the form is used to scroll through the data once you have entered it. The user presses the Home key on the keyboard to return to the top of the Patient Information Entry Form, or positions the cursor anywhere on the two forms and clicks the left mouse button to move to that point. The user should not attempt to exit the Patient Information screen as long as the message "Tape Analysis in Progress" appears in the upper right corner of the screen. Doing so may "crash" the system, in which case, the entire tape analysis process must be restarted.

F. ECG Bin Review

1. Overview

During tape analysis, the system processes data from the Holter tape and groups waveforms with similar morphologies into groups called "ECG Bins." This processing is described in detail elsewhere in the DSP Software Section of the specification.

To display the Bin Review function, the user selects Bin Review with the left mouse button from the Main Menu at the upper left corner of the screen. FIG. 8 illustrates a typical display screen during ECG Bin Review. When the ECG Bin Review is displayed, the user has the opportunity to view and analyze ECG data in several different ways.

- The Bin Review displays a representative beat 80 from each morphological category or bin.
- Each bin is numbered 82 consecutively, and labeled 83 with a diagnosis and the number of beats in the bin.
- The diagnosis of a bin can be changed.
- Bins can be merged with our bins.
- New bins can be created.
- Individual beats within each bin can be viewed, measured with on-screen calipers, and moved between bins.

The upper half 130 of the Bin Review screen, called the "bin display," shows a representative waveform from each bin identified by the system. Ten bins are displayed at a time. Additional bins can be viewed by using the scroll bar on the right side of the screen.

Each bin is labeled with the following information: a consecutive number that identifies the bin, the number of beats in the bin, and a diagnosis. For example:

Bin: 2
Beats: 114
Diagnosis: Normal

This example is the second group of waveforms identified by the system. There are 114 beats of this type, and the beats were diagnosed by the system as normal.

The lower half 132 of the Bin Review screen, called the "waveform display," shows the ECG waveform(s) in six-second real-time strips. The user can view the waveform from either channel 1 or 2, or both channels at once, change the scale of the waveforms, measure the beats, and print the waveform immediately or store it for later printing. The beat directly in the center, below the red heart 134, is the first beat in the highlighted bin 92 in the upper half of the screen. Subsequent beats in the same bin are identified with black hearts 136, and beats in other bins have grey hearts (not shown) above them.

When the scale is on the default setting, the grid on which the waveform is graphed measures 200 ms between each dot, horizontally, and 0.5000 mV between each dot, vertically. Below each beat is the number 139 of the bin to which that beat belongs, as well as the diagnosis 140. The numeral 142 to the left of the scroll bar directly above the waveform indicates the center beat's placement within the bin. For example, if the numeral 3 appears, the center beat is the third of that morphology identified by the system.

The time 144 displayed to the left of the scroll bar at the bottom of the screen indicates the time on the tape at which the first beat on the left side of the screen occurred.

2. View and Analyze ECG Bins

As best seen in FIG. 8, the upper portion of the screen is the bin display. In the preferred embodiment, ten bins are displayed at one time, five in each horizontal row. To view additional bins, the user selects the down arrow 146 on the vertical scroll bar to the right of the bin display. The next line of five bins appears at the bottom of the bin display, and the top line scrolls out of view. Now bins six through fifteen appear in the bin display. To return to the previous display, the user selects the up arrow 152. To scroll ten bins at once, the user moves the cursor to the grey area 150 on the scroll bar below the thumb 148 and clicks the left mouse button once. To scroll back ten bins, the user clicks the left mouse button above the thumb.

To view bins out of sequence, the user moves the thumb along the scroll bar. (See discussion of Totals later in this section for a description of how to determine the number of bins existing for each tape.) For example, if the system has created eighty bins and the user desires to view the fortieth bin, move the thumb one half of the way down the scroll bar.

In addition to the Main Menu, which is available throughout the Holter Analysis, several menus are available to provide a variety of options for ECG Bin Review. Menus for the bin display, which, as illustrated in FIG. 7, are listed on the horizontal bar directly above the bin display, are:

Diagnosis Menu 154
Bin Menu 156
Channel Menu 158
Scale Menu 160

Activating any of these menus with a mouse will cause a pull-down menu of options to appear on the screen.

a. Change a Diagnosis

The Diagnosis Menu allows a user to change the diagnosis of any bin. Once the user has selected the bin to be changed (it now appears highlighted), the user selects the word "Diagnosis" from the menu line directly above the bin display and holds the left mouse button down to display the Diagnosis Menu.

The user selects the desired diagnosis by releasing the left mouse button on the proper command with the Diagnosis Menu, best illustrated in FIG. 7.

The following diagnoses are available:

- Normal. Determined by the system to be the patient's normal heartbeat.
- PVC. Premature ventricular.
- SVPC. Supraventricular premature.
- UnDiag. Not diagnosed by the system.
- Delete. Deleted from the analysis and from the ECG report.

b. Bin Menu

The Bin Menu 156 is illustrated in FIG. 9 and provides the user with totals (total beats, bins, and totals in each diagnosis category) and allows the user to create new bins, merge and unmerge bins, and unmark bins that are marked. Selecting "Totals" from the Bin Menu displays a list of totals, as illustrated in FIG. 10, which overlays the bin display. To remove the Totals list from the screen, the cursor is moved to any position outside the list and the left mouse button is clicked once.

To create a new bin, the user selects "Create New Bin" from the Bin Menu, and an empty bin appears on the last page of the bin display and is labeled with the next consecutive number. To give the bin a diagnosis, follow the steps described above in the section titled "Change a Diagnosis." To move beats into the new bin, the user follows the steps described below in the section entitled "Move Beats."

If the user finds that two or more bins have very similar morphologies and, in the users judgment, should be combined into one bin, bins may be merged. The system provides three ways to merge; the first method is as follows:

The user selects a target bin (bin into which the others will be merged) with the left mouse button. It now appears highlighted. With the right mouse button, the user selects the bins to be merged into the target bin, using the scroll bar to the right of the display to move through the bins with the left mouse button, if necessary. Each selected bin appears bright green. To deselect a bin, the user clicks the right mouse button over the bin again. When the last bin to be merged has been selected, the user holds the right mouse button down By moving the mouse on the desktop, the last bin can be moved to the target bin. The bin flashes as it is moved. When the last selected bin is positioned over the target bin, the target bin appears bright red. The user releases the right mouse button and the message "Merging bins" appears on the screen. When the message disappears, all the selected bins are now included in the target bin. The number and the selected bins are now included in the target bin. The number and diagnosis of the target bin remain the same, but the number of beats within the target bin is increased by the total number of beats in the added bins.

The second method for merging bins is as follows:

The user selects a target bin with the left mouse button. It now appears highlighted. Next, the user selects the same target bin with the right mouse button. It now appears highlighted in blue. With the right mouse button, the user then selects the bins to be merged into the target bin, using the scroll bar to the right of the display to move through the bins with the left mouse button, if necessary. Each selected bin appears bright green. It is not necessary to hold the right mouse button down after selecting the last bin. When all bins to be merged are highlighted, the user selects the Bin Menu and selects the "Merge into Selected Bin" command, which now appears in boldface and is available for selection. The second method for merging may be preferable when many bins are to be merged.

The third method to merge bins is as follows:

The right mouse button is clicked over a bin, and the bin is highlighted in green. The right button is then released. The user may then move the mouse over any other bin and select that bin as the target bin by clicking the middle mouse button. When the middle button is clicked, the system will merge all marked bins with the target bin.

If the user creates a new bin or merges bins, the process can be undone by selecting "Undo" from the Bin Menu, provided this is done before performing another function.

If the user has marked or highlighted many bins and then decides not to complete the function, the user can unmark them all at once (instead of individually) by selecting this menu item from the Bin Menu. This feature is especially useful if the marked bins occur in widely separate places.

c. View a Different Channel

When the bin display appears, the representative beat in each bin is from channel 1. To view the beats from channel 2, or from both channels at once, the user must select the Channel Menu and hold down the left mouse key. A pull-down menu of channel commands will then appear, as illustrated in FIG. 11. When the cursor is positioned over the desired selection, the user releases the key. (Note that channel 1 appears lighter and cannot be selected, since the beat is currently viewed from channel 1.)

d. Change the Scale

Figure 12:
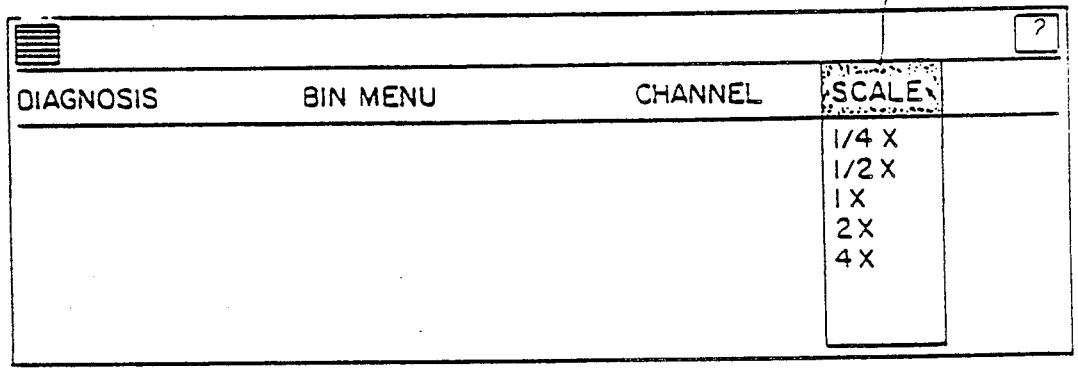
FIG. 12 is an illustration of the Bin Review Menus with the Scale Menu actuated.

To change the scale of the representative beats in the bins, the user must select the Scale Menu 160, hold down the left mouse button to select the size wanted, and then release the button The pull-down menu of Scale Commands is illustrated in FIG. 12. (The default setting is 1X and appears lighter on the menu.)

3. View and Analyze ECG Waveforms a. Waveform Display

The bin review waveform display on the lower half of the screen (see FIG. 8) allows the user to review each beat within its context in the ECG waveform The beat directly in the center of the screen, below the red heart, is the first beat in the bin highlighted in the upper half of the screen. Subsequent beats in the same bin are identified with black hearts, and beats in other bins have grey hearts above them.

Below each beat is the number of the bin to which that beat belongs, as well as the diagnosis. The numeral to the left of the scroll bar directly above the waveform indicates the center beat's placement within the bin. For example, if the numeral 3 appears, the center beat is the third of that morphology identified by the system.

The time 144 displayed to the left of the scroll bar at the bottom of the screen indicates the time on the tape at which the first beat on the left side of the screen occurred. Above the waveform appears the current scale setting 162 for waveform size. The default setting is:

200 ms/div, 0.5000 mV/div (1X).

Each is bounded by dots. The time scale remains at 200 milliseconds per division, or 200 milliseconds from one dot to the next. The amplitude scale can be changed to as small as 2.000 millivolts per division and as large as 0.125 millivolts per division. (See the description below entitled "Change the Scale.")

b. Scroll-Through Waveform

There are two scroll bars on the waveform display to enable the user to move through the waveform and view any six-second strip.

1. View Beats by Bins

Figure 13:
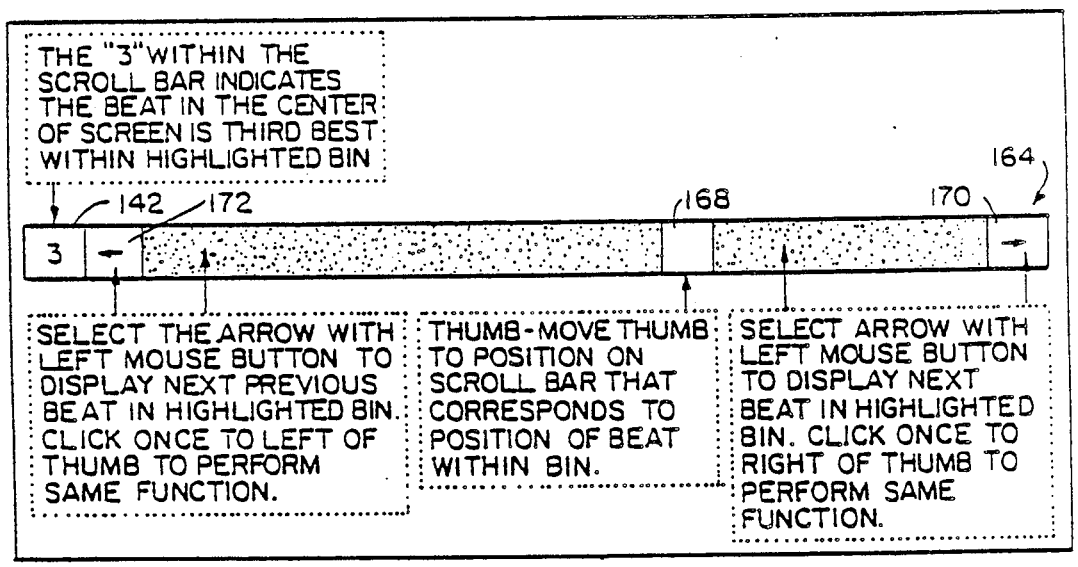
FIG. 13 is an enlarged view of the upper scroll bar for the bottom half of the screen display of FIG. 8.

The scroll bar 164 directly above the waveform display allows the user to scroll through the beats in the highlighted bin. This scroll bar is illustrated separately in FIG. 13. When the screen is first displayed, the number "1" appears in the box 142 on the left side of the scroll bar. A red heart 134 appears above the beat in the center of the screen. These features indicate that the beat in the center of the screen is the first beat in the highlighted bin. Furthermore, the thumb 168 (the white box on the scroll bar), is positioned to the far left end of the scroll bar. This indicates that the displayed waveform is at the very beginning of the data within the highlighted bin.

Subsequent beats within the highlighted bin appear with a black heart 136 above them. Beats from other bins have grey hearts above them. To scroll through the beats in the highlighted bin sequentially, the user moves the cursor to the arrow 170 on the right side of the scroll bar. To position the second beat within the highlighted bin in the center of the screen, the left mouse button is clicked once. (The same function can be accomplished by positioning the cursor anywhere on the scroll bar to he right of the thumb and clicking the left mouse button once.) The number "2" now appears in the box on the left end of the scroll bar, and the beat in the center of the screen has a black heart above it. The thumb has moved slightly to the right, although the movement may not be visible if there are many beats in the bin.

To scroll quickly through the bin, the user holds the left mouse button down over the right arrow, instead of clicking it. To move back through the bin, the user moves the cursor to the arrow 172 on the left end of the scroll bar and perform the same functions.

To jump to a beat out of sequence, the user moves the thumb along the scroll bar by positioning the cursor on the thumb, holding down the left mouse button and moving the cursor to the position on the scroll bar that corresponds to the position of the beat within the bin. For example, if the bin contains one hundred beats and the user wishes to view the fortieth beat, the thumb is moved four-tenths of the distance along the scroll bar. (Naturally, this is an inexact procedure. Once the left mouse button is released, the number in the box on the left of the bar indicates the number of the beat in the center of the screen. The arrows are used to move the exact beat that the user desires to view.)

2. View Beats by Time

The scroll bar 166 at the bottom of the screen allows the user to view the entire waveform in sequential six-second strips. The time of occurrence of the first beat on the left of the screen is displayed on the left end 144 of the scroll bar. Each click of the right arrow 174 moves the waveform ahead by five seconds. The left arrow 176 moves the waveform back by five seconds.

The thumb 178 is used to scroll through, using time as the reference. For example, if the user is viewing a twenty-four-hour tape and desires to view the waveform three hours into the tape, the user moves the thumb one-eighth of the distance along the scroll bar. The arrows on each end of the scroll bar are used to move to the exact time the user desires to view.

c. Menus

Figure 14:
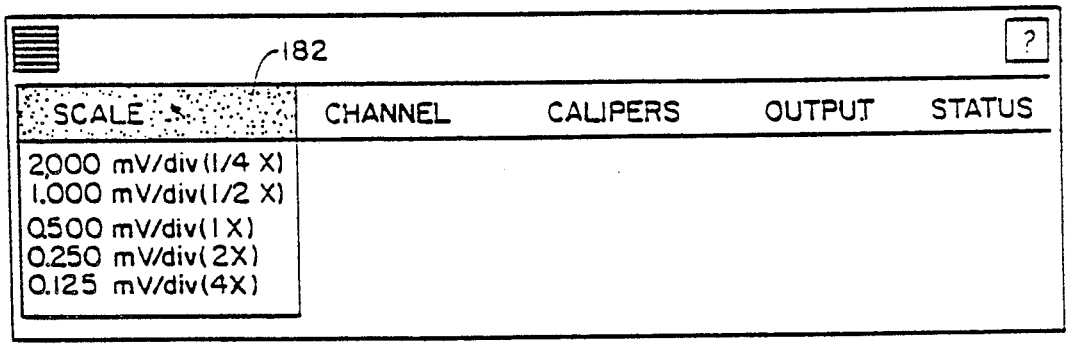
FIG. 14 is an illustration of the Bin Review Menus from the lower portion of the Bin Review Screen with the Scale Menu actuated.

The menus available for the waveform display appear on the menu line 180 directly above the waveform display. They are:
Scale Menu
Channel Menu
Calipers Menu
Output Menu
Status Menu 1. Change the Scale The size or scale of the waveform(s) can be enlarged or reduced. After displaying the Scale Menu 182, illustrated in FIG. 14, the user holds down the left mouse button and selects the desired scale by releasing the button over the desired selection. The default ssetting is 0.500 mV/div (1X).

2. View a Different Channel

When the ECG Beat Review is initially displayed, both channels 1 and 2 appear in the waveform display. The user can change the display to view only channel 1 or only channel 2 by making a selection from the Channel Menu 184, illustrated in FIG. 15.

3. Measure Beats with Calipers

The user can measure beats, or portions of beats, on the waveform display by using the calipers, which appear on the screen when the center mouse button is depressed. The calipers are produced by two sets of cross hairs. The vertical lines measure the duration of the beat; the horizontal lines measure the amplitude. Both measurments occur simultaneously.

Figure 16:
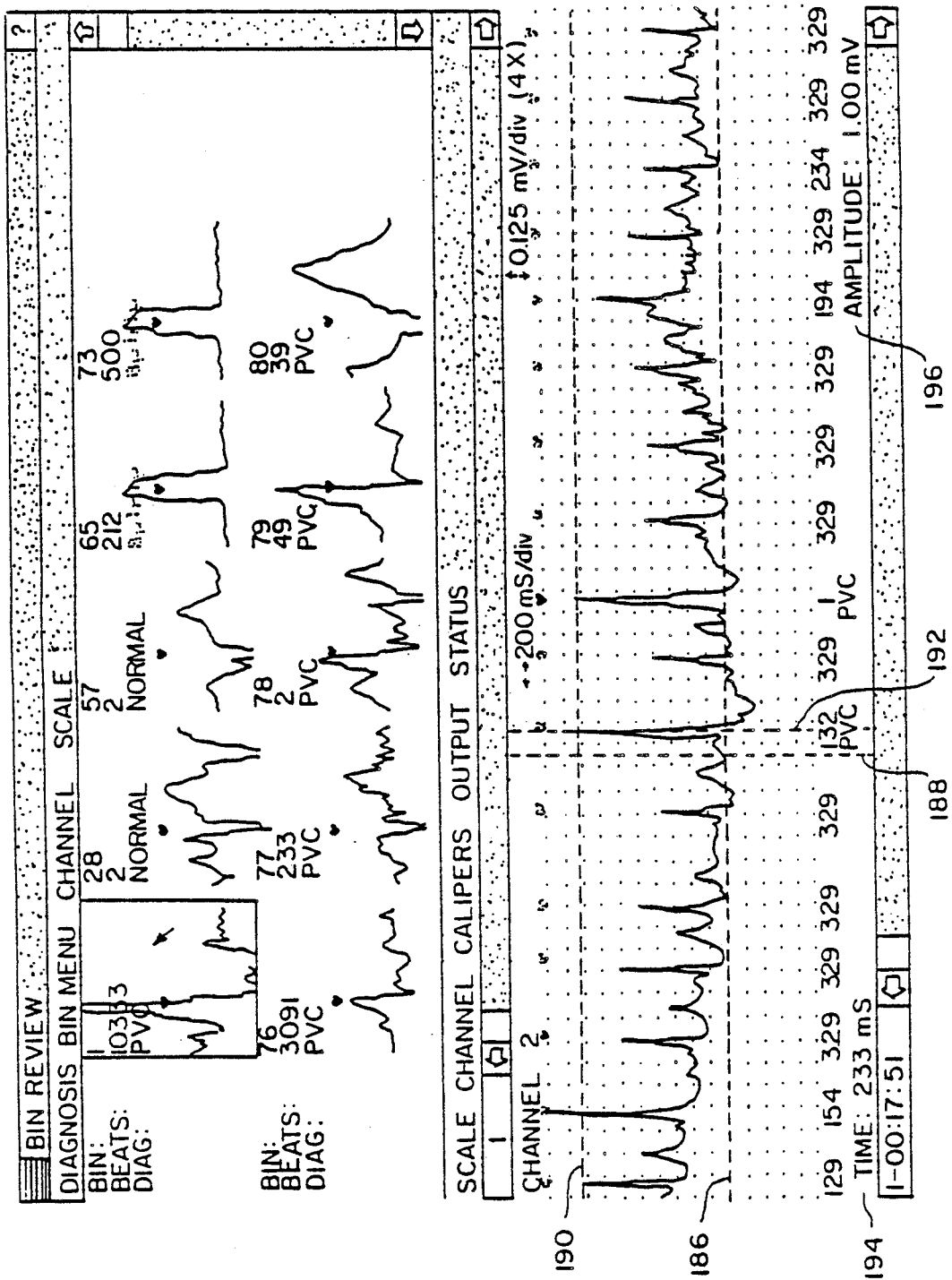
FIG. 16 is an illustration of a screen display from the Bin Review mode illustrating the Calipers as they are displayed on the screen.

A beat is measured using the following sequence:
First, the cursor is positioned at a first point of measurement on the waveform and the center mouse button is clicked A blue set of cross hairs 186, 188 appears, intersecting at the cursor point, as illustrated in FIG. 16. Next, the cursor is positioned at another point of measurement on the waveform and the user clicks the center mouse button A red set of cross hairs 190, 192 appears, intersecting at the cursor point The distance between the vertical lines is the duration of the measured segment and is displayed in millimeters per second in the lower left corner 194 of the waveform display. For example:
Time: 233 ms The distance between the horizontal lines is the amplitude of the measured segment and is displayed in millivolts in the lower right corner 196 of the waveform display. For example:
Amplitude: 1.00 mV
To make subsequent measurements, the cursor is moved to a new location, and the center mouse button is clicked again The intersection of the red cross hair moves to that point. The blue cross hair moves to the position the other cross hair just vacated.

The position of the calipers relative to one another can be locked by selecting Lock Calipers 198 from the Calipers Menu 200 with the left mouse button. The Calipers Menu is illustrated in FIG. 17. To move the locked calipers, the mouse is positioned on the point at which the user wants the intersection of the blue cross hairs. The user must click the middle mouse button, and the entire caliper apparatus moves.

To unlock the calipers, the user selects Unlock Calipers 202 from the menu with the left mouse button. To remove the calipers from the screen, the user selects Remove Calipers 204 from the menu with the left mouse button.

4. Output Menu

Ordinarily, the waveform display from the Bin Review function is not printed as part of the ECG report.

However, if the user desires to include the strip currently displayed, or print it immediately, the Output Menu 206, illustrated in FIG. 18, is selected.

To save the currently displayed strip for the ECG report, the user selects Save Strip for Report 208 from the Output Menu with the left mouse button. The user can also print the currently displayed waveform immediately by selecting Print Strip Now from the Output Menu. When the user selects either item from the Output Menu, a message indicating "Enter Title of Measurement" appears with an ACCEPT and CANCEL box. This allows the user to give the printed waveform strip a title, if desired. To insert a title, the user types in the title, moves the cursor to ACCEPT, and clicks the left mouse button. CANCEL is selected if the user decides not to print the waveform.

5. Review Beat Status

The user can obtain the status for the beat at the center of the waveform display. By selecting the Status Menu 212 and the Highlighted Beat Status command (the only command in the Status Menu), the user obtains a status chart 214 providing data on the beat in question, as illustrated in FIG. 20. Pressing any keyboard key will remove the display.

d. Move Beats

When the ECG Bin Review is displayed on the screen, the user can move individual beats between bins. Once a beat is moved to a different bin, the total number of beats in the bin is increased by one.

The user employs the following procedure to move a beat between bins:

1. The user positions the cursor over the beat to be moved, pressing the right mouse button and continuing to hold it down. The beat is high-lighted with a black bar and appears in the upper half of the screen, highlighted in black and flashing. The beat can now be moved to the target bin by moving the mouse.
2. When the beat is in position over the target mouse, the underlying bin is highlighted with red. When the user releases the right mouse button, the beat becomes part of the red highlighted bin. If the user releases the right mouse button and no bin is highlighted with red, the beat does not move to any other bin but remains in its original bin.
3. If the bin into which the user wants to move the highlighted beat is not displayed on the screen, the user must scroll through the bins by moving the flashing heartbeat off the bin display in the direction the users desire to scroll (i.e., up, to scroll back; down, to scroll forward).
4. Text appears on the top line of the screen documenting the move. For example, "Beat 1/Bin 8 Bin 9" indicates the first beat in bin 8 was moved to bin 9.

G. Full Disclosure

1. Overview

The Full Disclosure feature of the system organizes ECG data in several formats. It includes bar graphs, called "histograms," along with the ECG waveforms. The user accesses the Full Disclosure feature via the Main Menu.

In the Full Disclosure Format, as illustrated in FIG. 19, the top portion 216 of the screen displays the histograms 94, which illustrate the frequency of abnormal events, ST deviation and slope, and other diagnostic features over the course of the tape. The bottom portion 218 of the screen displays the ECG waveform for any point on the histogram selected by the user.

2. Histograms

A separate histogram is produced by each of the following events: PVC, Isolated PVC, Couplets, Runs, Beats in Runs, SVPC, Undiagnosed Beats, Deleted beats, Heart Rate (bpm), R-R Distances (ms), Pauses, patient-Initiated Event Markers, ST Deviation, and ST Slope.

Each vertical bar on a histogram represents occurrences of the captioned event. The vertical scroll bar 220 is used to view all the histograms. To scroll forward sequentially, the user selects the "down" arrow 222 or clicks the left mouse button below the thumb. The user scrolls back to previous histograms by selecting the "up" arrow 224. The thumb is used to view histograms out of sequence.

If the histogram is too long to be displayed on the screen at one time, the scroll bar 226 below the histogram must be used to view the remainder of the graph. The right arrow 228 is selected to view additional data, the left 230 arrow to return to previous data.

3. ECG Waveforms

When the Full Disclosure screen is first displayed, the waveform for the beginning of the tape appears on the screen. The user can then move the cursor to the point on the histogram to be viewed. That point is selected with the left mouse button. A vertical cursor locks onto the segment. (The vertical cursor is the same width as the histogram bar.) The ECG waveform for that point on the tape appears on the bottom portion of the screen. The default setting is a five-minute segment.

4. Pauses and Premature Beats

Pauses are marked on the ECG waveform by grey bars spanning the distance between the R waves. Premature beats are marked by solid black bars spanning the distance between the R-waves.

5. Menus

Figure 21:
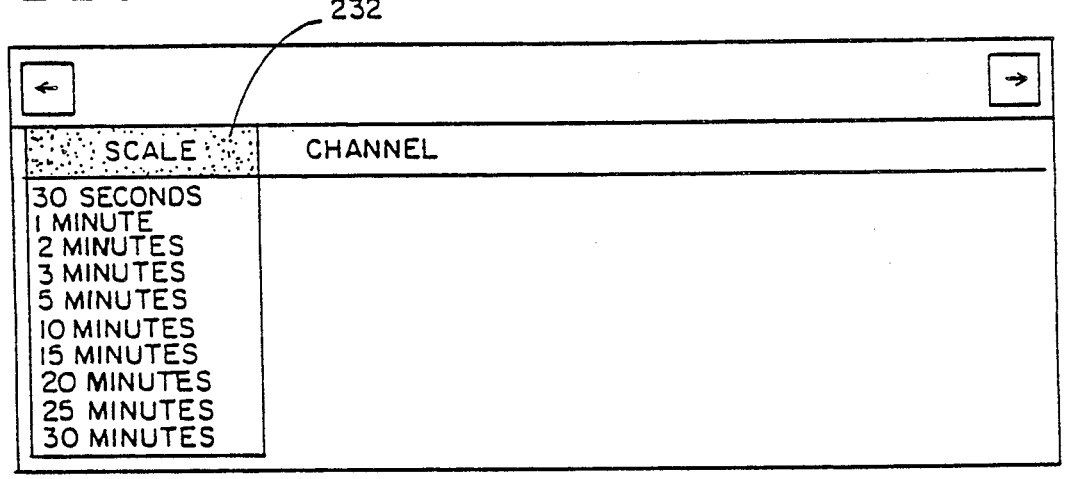
FIG. 21 is an illustration of the screen display when the scale menu within the Full Disclosure Mode is actuated.
Figure 22:
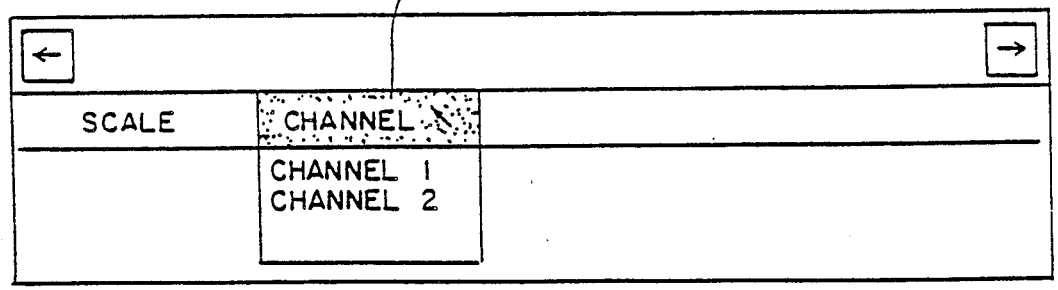
FIG. 22 is an illustration of the Channel Menu as it is displayed within the Full Disclosure Mode when actuated.

The menus available for the histogram display are the Scale Menu 232, illustrated in FIG. 21, and the Channel Menu 234, illustrated in FIG. 22. If the user desires to view a segment of ECG waveform that is longer or shorter than five minutes, a different scale is selected from the Scale Menu. The channel is displayed in the lower portion of the screen and can be changed from the Channel Menu with the left mouse button.

6. Viewing a Six-Second Strip

Figure 24:
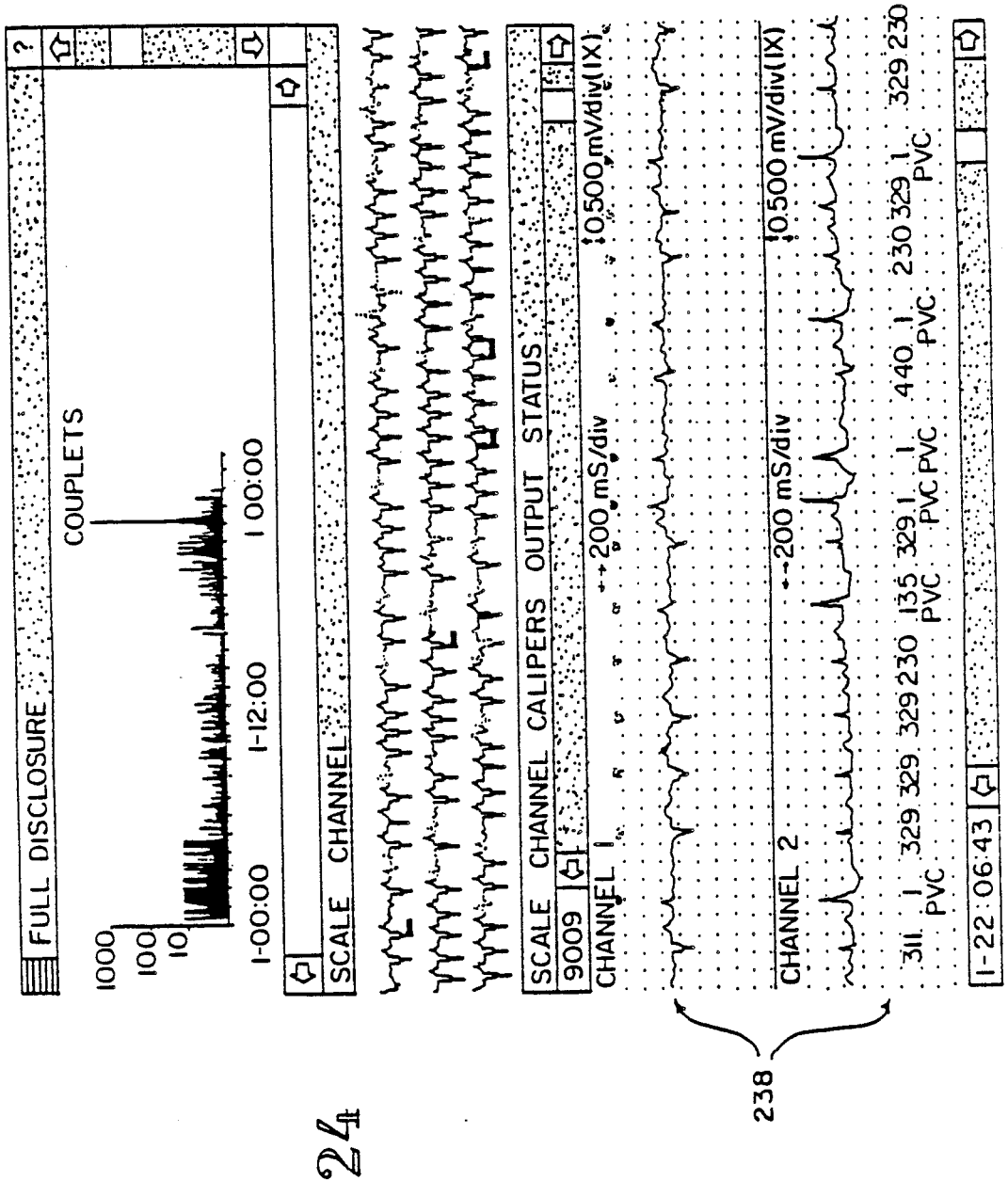
FIG. 24 is an illustration of the Full Disclosure screen display with two channels of Six-Second Strips displayed on the lower portion of the screen.

As the user moves the cursor over the ECG waveform on the bottom portion of the Full Format Screen, a box 236 encloses each beat as the cursor moves, as illustrated in FIG. 23. The user selects the beat to be analyzed by enclosing it in the box and clicking the left mouse button. This brings up a six-second real-time strip 238, with the selected beat located in the center, under a red heart (in this case, the red heart does not indicate that the beat is the first one in its bin), as illustrated in FIG. 24. This strip is precisely the same waveform display as s found in the Bin Review, and all the functions available in Bin Review are available in this mode.

To remove the six-second strip from the Full Disclosure screen, the user must move the cursor out of that display and click the left mouse button. Once a Bin Review function is initiated (merge bins, move beats, etc.) in this mode, the bin display appears on the upper portion of the screen, above the waveform display. However, the words "Full Disclosure" appear on the top horizontal bar to remind the user that the system is still in the Full Disclosure mode. To remove the Bin Review screen and return to the Full Disclosure Screen, "Full Disclosure" is selected from the horizontal bar.

H. Superimposition

1. Overview

Superimposition displays each heartbeat detected on the Holter tape individually in rapid succession. The system of the preferred embodiment uses audio-visual superimposition with color coding of abnormal (normal beats appear green; abnormal beats appear blue) This feature allows the user to use both auditory and color-enhanced visual cues in identifying arrythmias. From the Superimposition screen, the user can view heartbeats in rapid superimposition, print any beat within its real-time ECG waveform, or move it to a different bin. The Superimposition function is initiated by selecting Superimposition from the Main Menu.

The rapid succession of individual heartbeats, called "superimposition," begins immediately when the Superimposition screen comes up. Normal heartbeats appear green; abnormal beats appear blue. Superimposition pauses with each abnormal beat to allow the user time to freeze the screen. FIG. 24 illustrates a sample display screen in Superimposition mode. An abnormal beat labeled PVC appears in the display.

2. Freeze the Screen

To freeze the succession of beats and view a single beat, the user must click the left mouse button. The waveform on the beat display portion of the screen at that time continues to be displayed. The diagnosis 242 of the beat is shown to the left of the waveform display. The time of occurrence 244 of the beat is displayed in the scroll bar 246 at the bottom of the screen.

3. Restart Superimposition

To return to the rapid succession of heartbeats, the user moves the cursor to the small Motion Bar 248 below the superimposition display and selects the appropriate arrow 250, 252 to continue superimposition in the forward or reverse direction.

4. Scroll Bar

The scroll bar at the bottom of the screen can be used to view beats which occurred before or after the beat displayed on the screen. To see the beat which occurred immediately prior to the beat on the screen, the user must select the left arrow 252 or click the left mouse button to the left of the thumb. The right arrow 258 must be selected to view the beat which occurred after the beat on the screen. The thumb 256 in the scroll bar is moved to view beats relative to the position of the thumb in the scroll bar. For example, to view a beat twelve hours into the twenty-four-hour tape, the user moves the thumb to the middle of the scroll bar.

5. P-Wave Pointer

Figures 28, 29:
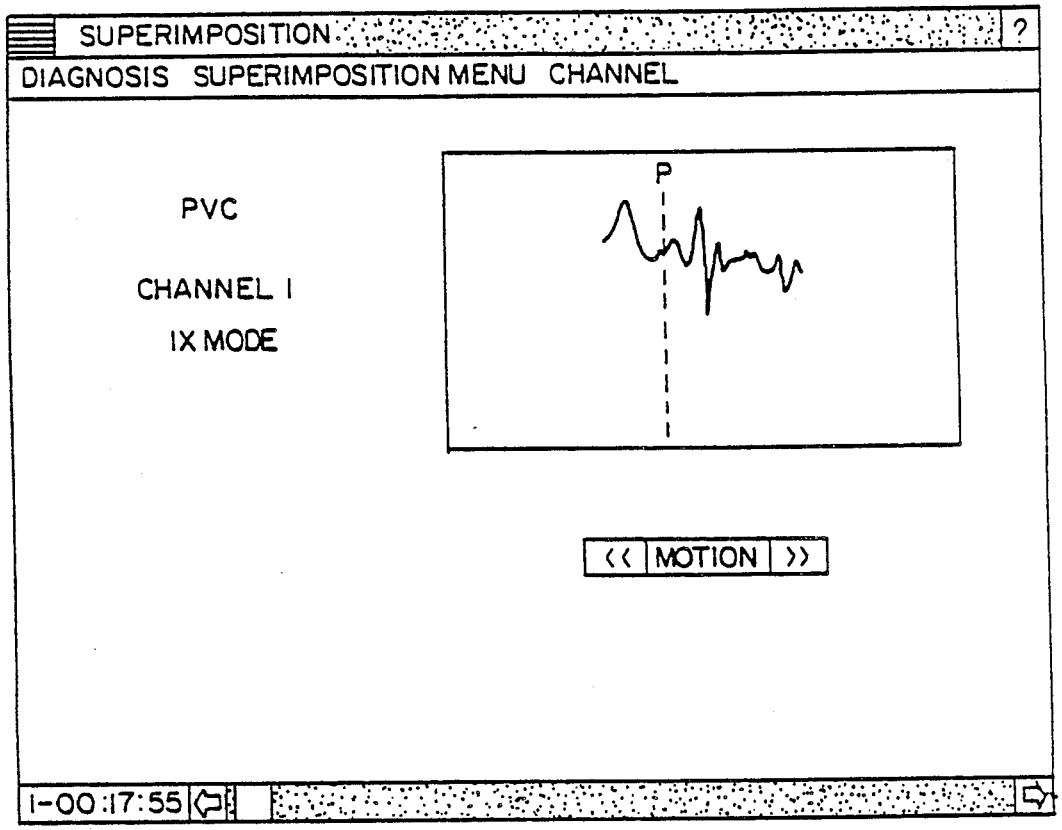
FIG. 28 is an illustration of the screen in the Superimposition Mode, with the wave pointer in pace in the beat display area.
FIG. 29 is an illustration of the Report Option screen generated by the system of FIG. 1 in the Report Mode.

The P-wave pointer 260 appears on the right of the superimposition waveform display. To position the pointer on the P-wave, move the cursor over the black superimposition display. The cursor now appears as a white cross 262. The cross is moved to the position on the waveform where the user wants the pointer, and the left mouse button is clicked once. The P-wave pointer will then appear at the desired location on the wave, as illustrated in FIG. 28.

6. Superimposition Menu a. View a Six-Second Strip

Figure 26:
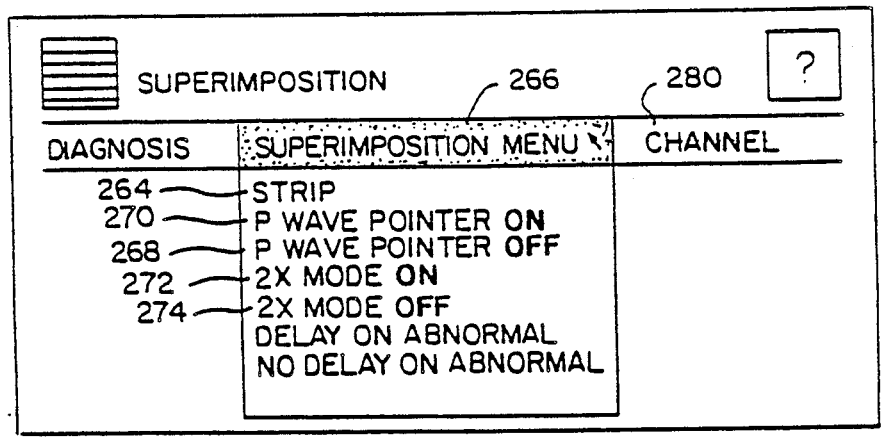
FIG. 26 is an illustration of the menu bar in the Superimposition Mode, with the Superimposition Menu actuated.

When a beat is frozen on the screen, the user can view a six-second real-time strip with the superimposition beat located in the center of the strip. A sample display of this type is illustrated in FIG. 27. Select Strip 264 from the Superimposition Menu (see FIG. 26) and the screen automatically displays the six-second time strip. In this mode, the user can perform all of the functions available in the Bin Review mode. To return to superimposition, the user moves the cursor to the right side of the horizontal bar at the top of the screen and selects the word "Superimposition."

b. Turn Pointer ON/OFF

The P-wave pointer automatically appears when the superimposition screen comes up. To remove it, the user must select Turn P Wave Pointer OFF 268 from the Superimposition Menu. Turn P Wave Pointer ON 270 is selected to redisplay it.

c. 2X Mode ON/OFF

The user selects 2X Mode ON 272 to display the heartbeat in a double-wide format. Select 2X Mode OFF 274 is selected to return the display to its default setting.

d. Delay On Abnormal ON/OFF

When the Delay On Abnormal 276 is selected, display of each abnormal beat during superimposition is slightly longer than the display of a normal beat. This allows the user time to stop the superimposition, if desired. When the No Delay On Abnormal 278 is selected, there is no delay in the display time for abnormal beats.

e. Change the Channel

The heartbeats displayed in superimposition will be from channel 1. To view superimposition in channel 2, the user must select it from the Channel Menu 280 (shown in deactivated position in FIG. 26).

I. REPORT COMMENTARY

Comments can be added to a report generated by the system by selecting Comments from the Main Menu. A blank page appears on the screen to allow the user to type in any comments to be included in the printed ECG report. Comments are typed on the keyboard by the user. The cursor indicates the position on the page. When a line is filled, the system will automatically move to the beginning of the next line. The Enter or Return key is used to enter carriage returns at the end of paragraphs. As the page becomes full, the screen automatically scrolls up to reveal one more blank line at a time.

If a mistake is made while entering information, the backspace key is used to delete. Text out of sequence is deleted by moving the cursor to the end of the text to delete, clicking the left mouse button and using the backspace key. To join two paragraphs, the user must place the cursor at the beginning of the second paragraph and press the backspace key to remove the carriage returns.

To add information out of sequence, the user must move the cursor to the place where information is to be added. The left mouse button is then clicked once and new information typed and inserted into the text.

1. Scrolling

Once the comments are entered, the vertical scroll bar is used to the right of the display to review the text. The user selects the "down" arrow to move forward through the text and selects the "up" arrow to move back through the text. The thumb is used to view text out of sequence.

2. Report Interpretation

This feature functions exactly the same way as does Report Comments.

3. Print ECG Report

The preferred embodiment provides options for printed ECG reports. To access the options, the user selects Print Report from the Main Menu. The screen illustrated in FIG. 29 appears to allow the user to select the information to be printed.

Patient Information/Patient Diary: Select YES to include the identification and diary information you entered.

ECG Summary Report: Select YES to include a summary of events in table form.

Report Commentary/Physician Interpretation: Select YES to include the comments and interpretation.

Tabulations: Select YES to include hour-by-hour totals.

Histograms: Select YES to include the histograms.

ECG Analysis Strips: Select YES to include any six-second waveform strips you saved.

Full Disclosure ECG Report: Select YES to include the entire twenty-four-hour ECG waveform. The printout includes either or both channels, and diagnoses for abnormal beats. A summary appears across the top of each page.

Select "Accept" to initiate printing.

Any time during the printing process, the user can interrupt printing by pressing any keyboard key.

III. DIGITAL SIGNAL PROCESSING HARDWARE

The digital signal processing hardware of the present invention is shown in the detailed schematic diagrams of FIGS. 30A-C, 31A-C, 32A-C and 33. This hardware resides on the digital signal processing (DSP) board 64 that is installed in an expansion slot of an IBM AT-compatible microcomputer 60 (see FIG. 1). A major component of the DSP board 64 is the DSP chip 300 (in FIG. 30B). DSP chip 300 is useful in computationintensive applications, such as ECG analysis and interpretation. The DSP chip 300 can be, for example, a Texas Instruments TMS320C25. The TMS320C25 provides a 100-nanosecond instruction cycle time; 4 k words of on-chip massed ROM; a fully static, double-buffered serial port; concurrent direct memory access (DMA) using an extended hold operation; and bit-reversed addressing modes for radix-2 Fast Fourier Transforms (FFTs). The DSP chip 300 and the main processor subsystem 62 communicate via data buses that are connected to first-in, first-out (FIFO) circuits and buffer circuits.

The DSP board 64 is used in the three passes through the data: the beat detection pass, the binning pass, and the rasterization pass. In addition, the DSP can be used to provide superimposition of the data images on the display screen 66 that is connected to the microcomputer 60.

For each pass through the data, the DSP chip 300 is provided with a program by the main processor subsystem 62. The main processor subsystem 62 sends commands to the DSP chip 300 through its SD data bus 302 (see FIG. 32C).

The unidirectional buffers 323a and 323b (FIGS. 31A and 31B, respectively) provide the main processor subsystem with information concerning the status of the tape player and the FIFOs 320a and b through the buffered SD data bus 303.

Figure 32A:
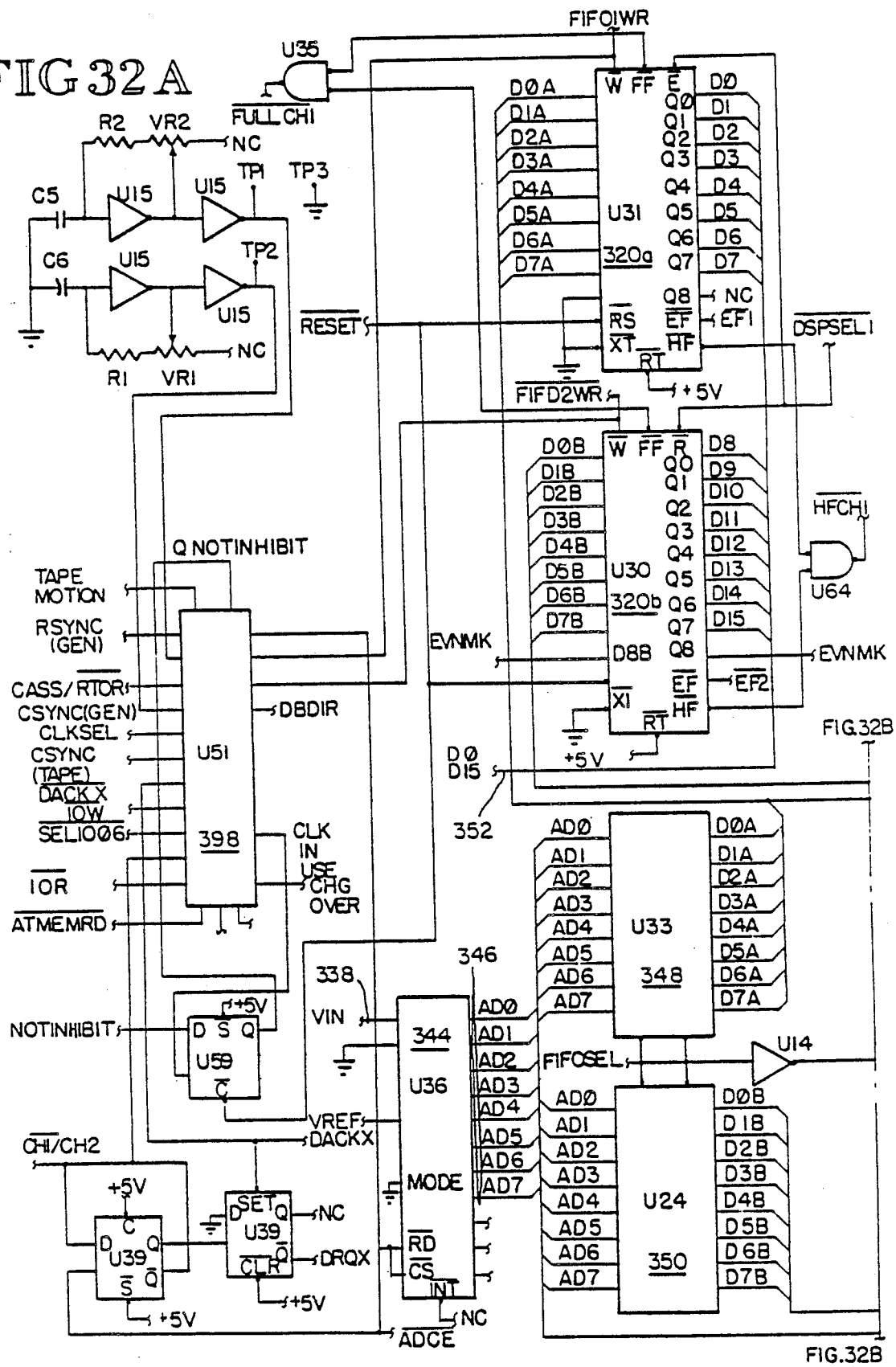
FIG. 32A is a detailed schematic diagram of a first part of a third portion of the digital signal processing board of the present invention.
Figure 32C:
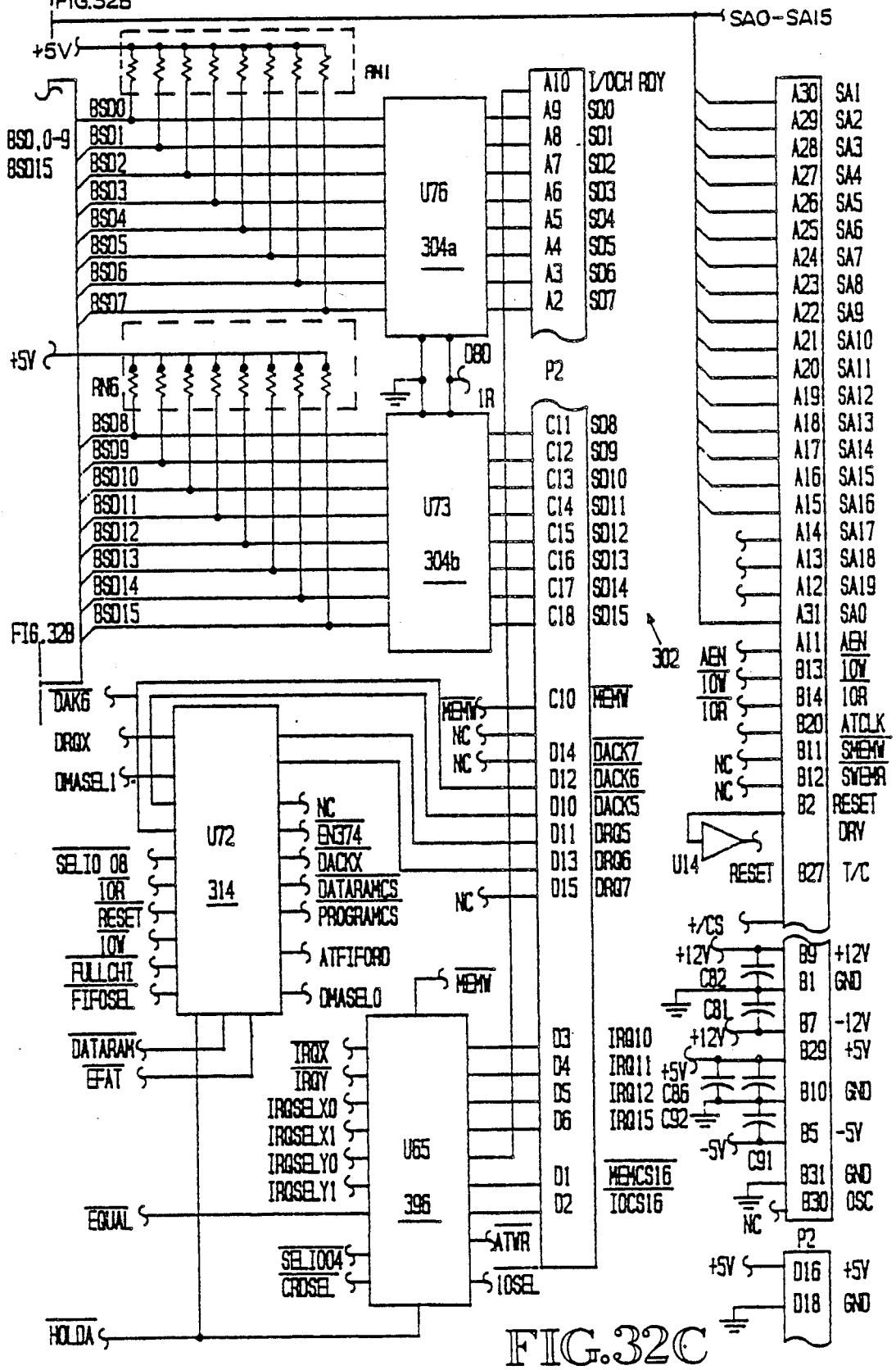
FIG. 32C is a detailed schematic diagram of a third part of a third portion of the digital signal processing board of the present invention.

The signals on the SD data bus 302 are passed through bidirectional drivers 304a and 304b (see FIG. 32C). The bidirectional drivers 304a and b are used to isolate the data bus of the main processor subsystem 62 from the circuitry on the DSP board 64. The resulting signals, labeled "BSD signals," carry information from the main processor subsystem to the DSP board 64 and from the DSP board 64 to the main processor subsystem 62. For example, the main processor subsystem 62 can be connected, through the bidirectional, tristatable buffers 306a and 306b (in FIG. 30A), to the program random access memory (RAM) 308 and the data RAM 310 (both shown in FIG. 30A), and to the DSP chip 300.

The address bus of the main processor subsystem 62 is isolated from the circuitry of the DSP board 64 by the unidirectional, tristatable buffers 305a and b. These buffers can be put into a hold state in which the main processor subsystem 62 can access the address bus of the DSP chip 300.

To enter a program into the program RAM 308, for use by the DSP chip 300, the main processor subsystem 62 sends commands over the DS data bus 302 to the octal latches 312a (see FIG. 31A) and 312b (see FIG. 318). The octal latches 312a and b produce signals that can control tape players, select FIFO chips, select RAM sets, and cause the DSP chip 300 to enter a suitable state when a program is being read from the main processor subsystem 62 to the program RAM 308. In particular, the SD data bus 302 can be caused to carry information that sets the LHOLD* (the logical complement of LHOLD) and LRESET* variables low. These signals cause the DSP chip 300 to hold operation and to set its program counter to zero. After the program has been entered in the program RAM 308, the DSP chip 300 will begin to execute its program at location 0.

The program RAM 308 and the data RAM 310 can be alternately selected by an appropriate setting of the DATARAM variable produced by the octal latch 312a. This signal is received by the logic chip 314 (see FIG. 32C) and combined with other signals to produce the DATARAMCS* and PROGRAMCS* signals. These signals are sent to the data RAM 310 and the program RAM 308 when they are respectively being written to or read from.

Before the DSP chip 300 is used in making a first pass through the ECG data, it is maintained in an inoperative state by appropriate signals from the main processor subsystem 62. When the main procesor subsystem 62 determines that it is time to make the first pass through the data, the program RAM 308 is loaded with a program module which detects heartbeats in the ECG data. Subsequently, after the first pass through the data has been completed, the program RAM 308 associated with the DSP chip 300 is loaded with a second program module for binning the heartbeats detected in the first pass. Later, when it is desired to produce hard copy of the results of the analysis on the laser printer 72, a rasterization program module is entered into the program RAM 308 from the main processor subsystem 62.

A detailed discussion of the operation of the heartbeat detection software is provided subsequently. The data operated on by the heartbeat detection program module is obtained from a tape source which was used to monitor the ECG signals of a patient for an extended period of time, such as twenty-four hours or forty-eight hours. The tape source can be either a cassette player or a reel-to-reel player. In either case, the tape player responds to signals sent by the main processor subsystem 62 through the octal latches 312a and b to the jack 316 (see FIG. 31A). In return, the main processor subsystem 62 receives signals concerning the status of the tape player and the status of FIFOs 320a and 320b (see FIG. 32A) through jack 318 (see FIG. 31A). Each of the FIFOs 320a and 320b is 512 words deep.

Figure 31A:
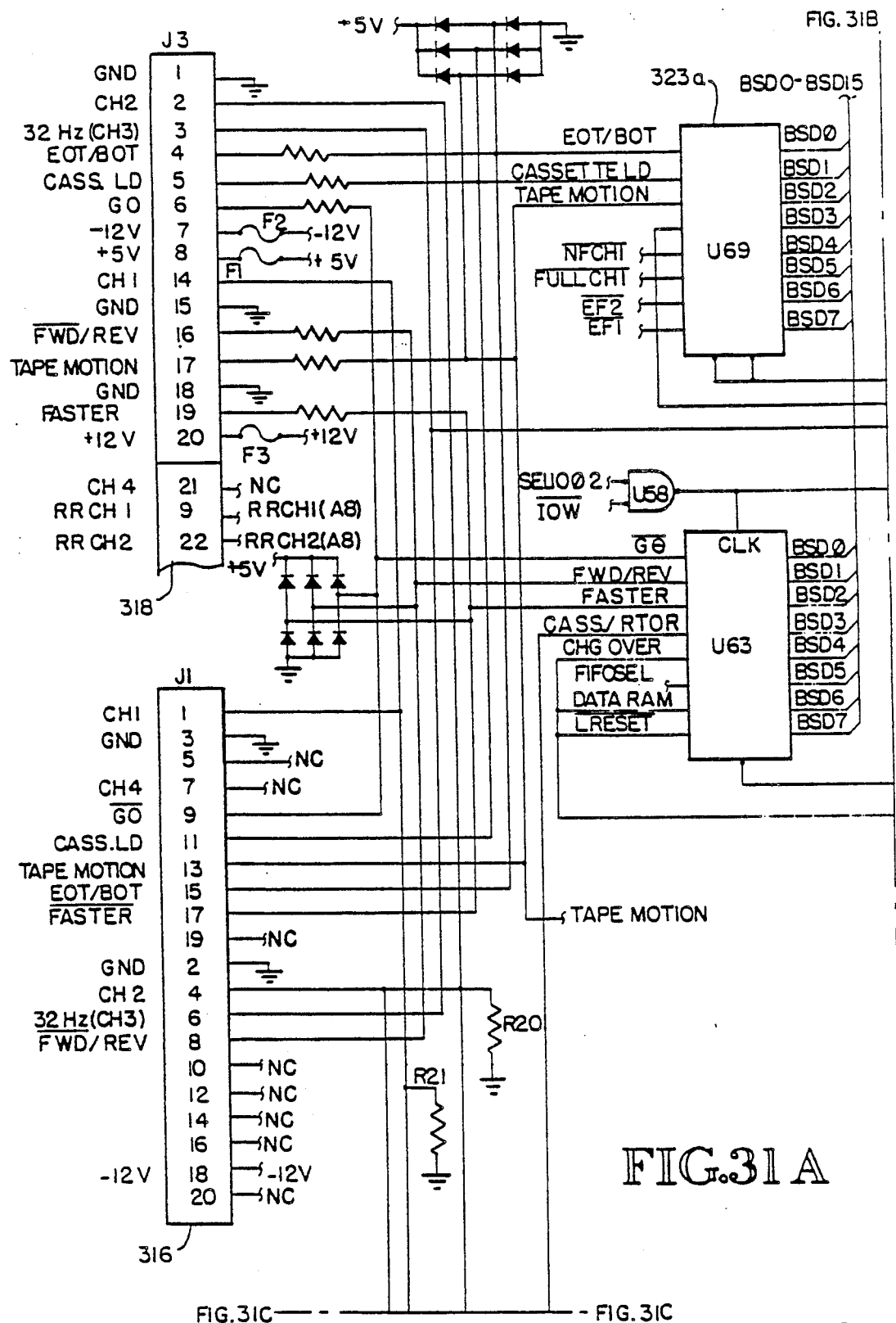
FIG. 31A is a detailed schematic diagram of a first part of a second portion of the digital signal processing board of the present invention.
Figure 31C:
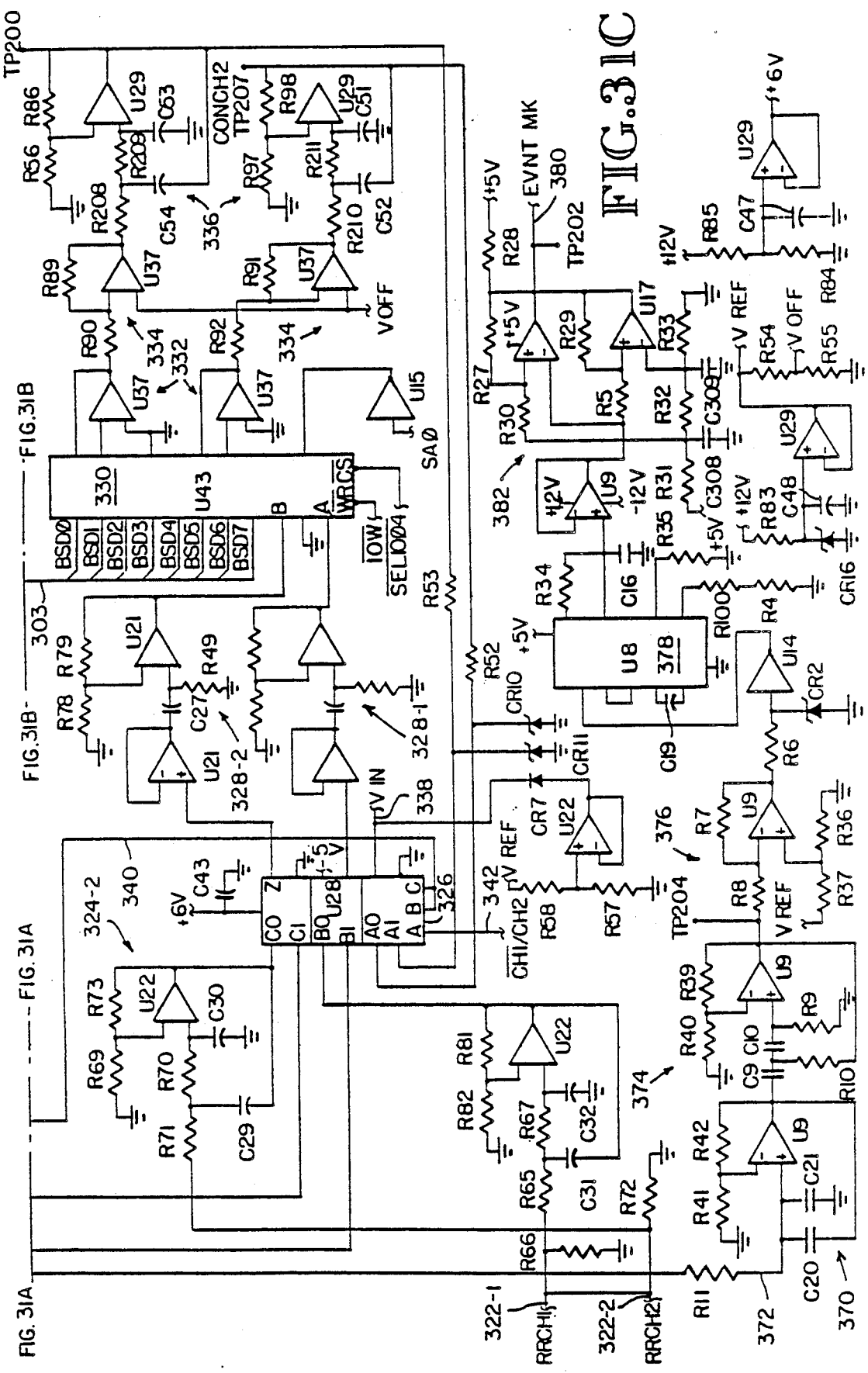
FIG. 31C is a detailed schematic diagram of a third part of a second portion of the digital signal processing board of the present invention.

The information contained on a reel-to-reel tape source is received by the DSP board 64 at the tape source inputs 322-1 and 322-2 (see FIG. 31C). Reel-to-reel tape source input 322-1 provides the tape source information concerning channel 1 of the ECG data, while input 322-2 provides the channel 2 inputs The channel 1 and channel 2 signals pass through the low-pass filters 324-1 and 324-2, respectively. The outputs of the reel-to-reel low-pass filters 324-1 and -2 are input to two channels of a multiplexer 326 that is being operated as a switch. The multiplexer is also connected to the channel 1 and channel 2 inputs that can be connected to a cassette player through the jack 316. An extra low-pass filter stage, such as reel-to-reel low-pass filters 324-1 and -2, is required because the reel-to-reel tape source must be played at a slower speed than the cassette tape source in order to provide proper samples at 120 Hz/channel.

The two channel signals output from the multiplexer 326 pass to stages 328-1 and 328-2. Stages 328-1 and -2 respectively provide buffering, high-pass filtering, and gain for the information on channels 1 and 2. These channels are then fed to the two-channel D-to-A converter 330. The D-to-A converter 330 can be operated, under control of data received from the buffered SD data bus 303, to independently control the gain on channels 1 and 2. After passing through the D-to-A converter 330, the two channel signals pass through the current-to-voltage conversion stages 332, the gain stages 334, and the anti-aliasing, low-pass filters 336. The outputs of the filters 336 are returned the multiplexer 326, which alternately produces samples of the data on channels 1 and 2 (signal line 338).

The signal received by the multiplexer 326 from the octal latch 312a over the signal line 340 specifies whether the signals produced on the signal 338 by the multiplexer 326 are produced by the cassette inputs or the reel-to-reel inputs. The signal provided to the multiplexer 326 on the signal line 342 determines the switching between the channel 1 and channel 2 data supplied to the multiplexer 326.

The analog signals on the signal line 338 are presented to the A-to-D converter 344 (see FIG. 32A). The eight-bit outputs produced on the AD bus 346 pass through the unidirectional, tristatable buffers 348 and 350 to the FIFOs 320a and 320b, respectively. The data produced by the FIFOs 320a and b is placed on the data bus 352 of the DSP chip 300. This data passes to the DSP chip 300 for further processing (see FIGS. 30B and 30A).

The data also passes to the main processor subsystem 62 through the octal D flip-flops 354 and 356 (see FIG. 32B). Octal D flip-flops 354 and 356 are used as data latches to pass the data through the buffered SD data bus 303 and the bidirectional drivers 304a and 304b to the SD data bus 302 of the main processor subsystem 62.

In addition, when the heartbeat detection software detects a beat, the DSP chip 300 causes a beat time log (BTL) to be produced and sent to the expanded RAM 71 of the main processor subsystem 62 (see FIG. 1). The beat time log, which contains the time of the detected beat, among other data, is sent to the main processor subsystem 62 through the DSP FIFOs 358 and 360 (see FIGS. 30B and 30C, respectively).

The patient monitoring apparatus records a third channel on the data tape, if a cassette player is used. This channel is not available on reel-to-reel tapes. This channel contains a 32-Hz clock which can be used to provide appropriate timing signals for use in reading the ECG data on channels 1 and 2. The 32-Hz clock, read from the jack 316, is presented to a phase-lock loop 362 (see FIG. 31B) whose phase reference is provided by a 240-Hz frequency source 364 to a divide- by-fifteen counter 366. The divide-by-fifteen counter 360 is placed in the feedback loop of the phase-lock loop 362.

To detect whether the clock is "out of lock," the window comparator 368 produces a signal whenever an output of the phase-lock loop 362 differs from approximately 2.5 volts, which indicates that the phase-lock loop is locked. In the case that the window comparator detects that the phase-lock loop is no longer locked or that a reel-to-reel tape is the source of the ECG signals, it causes a synchronous clock to be connected to the circuitry reading the ECG channel data.

The ECG tapes are also provided with an event marker signal, which is a 32-Hz signal imposed on channel 2 of the ECG data by the patient to indicate the occurrence of significant events. The channel 2 signal is provided to a low-pass filter 370 over signal line 372. The low-pass filter is followed by a high-pass filter stage 374. Both low-pass filter 370 and high-pass filter 374 have their knees at approximately 32 Hz, so the effect of cascading the two is to provide a bandpass filter centered at 32 Hz. The filter sections are followed by a high-gain amplifier 376 and a phase-lock loop 378, which has been tuned to 8 kHz. The event marker signal 380 is produced when the output of the phase-lock loop 378 passes through conditioning circuitry 382. This signal is connected to the DSP FIFO 320b (see FIG. 32A).

With the completion of the first pass through the data, the AT causes a new program module to be read into the program RAM 308 of the DSP board 64. The purpose of the second pass is to categorize the detected heartbeats into bins and to measure ST values for the detected heartbeats. As discussed above in connection with preparations for the first pass, the main processor subsystem 62 causes the DSP chip 300 to be held and reset while the program is being read into the program RAM 308. After the program has been read into the program RAM 308, the DSP chip 300 is allowed to operate according to the program. Under control of the program, the FIFOs 320a and 320b (in FIG. 32A) read data from the main processor subsystem 62. This is accomplished when the main processor subsystem 62 deselects the unidirectional, tristatable buffers 348 and 350 and selects the unidirectional, tristatable buffers 384 and 386. Then, data on the buffered SD data bus 303 passes to the FIFOs 320a and 320b. The beat time log entries are read through the FIFOs 320a and 320b into the memory associated with the DSP 300.

The beat data is fed directly from the buffered SD data bus 302 into one of two 6 k buffers that are specially designated sections in the data RAM 310. This data is monitored by the main processor subsystem 62, which continually fills the buffer that is not being accessed by the DSP chip 300 at any particular time. Control of this operation is accomplished by the gate array logic chip 314. The gate array logic chip 314 realizes the following equations:

TABLE A

```
DATARAMCS = DATARAM;
PROGRAMCS = !DATARAM;
ENABLE DATARAMCS = HOLDA;
ENABLE PROGRAMCS = HOLDA;
EN374 = !FIFOSEL & DACK 5 & DMASEL0;
DRQ5 = !FIFOSEL & DRQX & !DACK5;
DRQ5 = FIFOSEL & !DACK5 & !FULL_CH1;
ENABLE DRQ5 = DMASEL0;
DRQ6 = !EFAT & !DACK6;
ENABLE DRQ6 = DMASEL1;
DACKX = DACK5 & DAMSEL0;
DACKX = RESET & DRQX;
ATFIFORD = DMASEL1 & DACK6 & IOR;
ATFIFORD = SELIO08 & IOR;
ATFIFORD = ATFIFORD & DACK6 & !SELIO08;
ATFIFORD = ATFIFORD & IOR & !SELIO08.
```

The data RAM and program RAM chip-select signals are respectively equal to the data RAM signal and its complement. These signals, however, are not enabled unless the hold A signal is high.

Simultaneously with the binning operation, the DSP chip 300 maintains a bin record array which contains information concerning the bins created by the program. The data retained by the DSP chip includes bin numbers and the number of beats categorized in each bin. The bin record array is downloaded to the hard disk 73 of the main processor subsystem 62. In addition, the binning software calculates bin image averages as the bins are decided. These images are also downloaded to the disk of the main processor subsystem 62, as described above.

Depending upon signals provided by the address bus of the main processor subsystem 62 to the magnitude comparators 388 and 390 (see FIG. 30C), the three-to-eight decoders 392a and b produce appropriate I/0 selection signals. Similarly, in response to address signals produced by the DSP chip 300, the three-to-eight decoder (see FIG. 30B) produces DSP select signals. Both the SELIO and the DSPSEL signals are used to control the appropriate configurations of buffers and FIFOs to route the data between the main processor subsystem 62 and the DSP chip 300. For example, the logic circuit 396 (see FIG. 32C) produces an interrupt request signal from logical combinations of interrupt request selection signals. Similarly, the logic circuit 398 (see FIG. 32A) produces logical combinations of variables concerned with tape motion and memory access. The equations for logic circuits and 398 are respectively found in the tables below:

TABLE B

```
IOCS16 = IOSEL;
ENABLE IOSC16 = IOSEL & !SELIO04;
IRQ10 = IRQX;
ENABLE IRQ10 = IRQSELX0 & !IRQSELX1;
IRQ11 = IRQX;
ENABLE IRQ11 = !IRQSELX0 & IRQSELX1;
IRQ12 = IRQY;
ENABLE IRQ12 = IRQSELY0 & !IRQSELY1;
IRQ15 = IRQY;
ENABLE IRQ15 = !IRQSELY0 & IRQSELY1;
MEMCS16 = EQUAL;
ENABLE MEMCS16 = EQUAL;
IOCHREADY = CRDSEL & HOLDA;
ENABLE IOCHREADY = CRDSEL & !HOLDA;
ATWR = MEMW & CRDSEL.
```

TABLE C

```
DBDIR = ATMEMRD;
DBDIR = IOSEL & IOR;
DBDIR = DACKX & IOR;
DBDIR - ATFIFORD;
ADCE = FIFOSEL & RSYNC & !CASS_RTOR & NOTINHIBITED &
TAPEMOTION;
ADCE = FIFOSEL & CSYNC_GEN & CASS_RTOR & !CLKSEL &
NOTINHIBITED & TAPEMOTION;
ADCE = FIFOSEL & CSYNC_TAPE & CASS_RTOR & CLKSEL &
NOTINHIBITED & TAPEMOTION;
FIFO1WR = FIFOSEL & RSYNC & !CASS_TOR & NOTINHIBITED &
CH1_CH2 & TAPEMOTION;
FIFO1WR = FIFOSEL & CSYNC_GEN & CASS_RTOR & !CLKSEL &
NOTINHIBITED & CH1_CH2 & TAPEMOTION;
FIFO1WR = FIFOSEL & CSYNC_TAPE & CASS_RTOR & CLKSEL &
NOTINHIBITED & CH1_CH2 & TAPEMOTION;
FIFO1WR = !FIFOSEL & IOW & SELIO 6;
FIFO2WR = FIFOSEL & RSYNC & !CASS_TOR & NOTINHIBITED &
!CH1_CH2 & TAPEMOTION;
FIFO2WR = FIFOSEL & CSYNC_GEN & CASS_RTOR & !CLKSEL &
NOTINHIBITED & !CH1_CH2 & TAPEMOTION;
FIFO2WR = FIFOSEL & CSYNC_TAPE & CASS_RTOR & CLKSEL &
NOTINHIBITED & !CH1_CH2 & TAPEMOTION;
FIFO2WR = !FIFOSEL & IOW & SELIO 6;
CLK_IN_USE = FIFOSEL & RSYNC & !CASS_RTOR;
CLK_IN_USE = FIFOSEL & CSYNC_GEN & CASS_RTOR & !CLKSEL;
CLK_IN_USE = FIFOSEL & CSYNC_TAPE & CASS_RTOR & CLKSEL.
```

Figure 33:
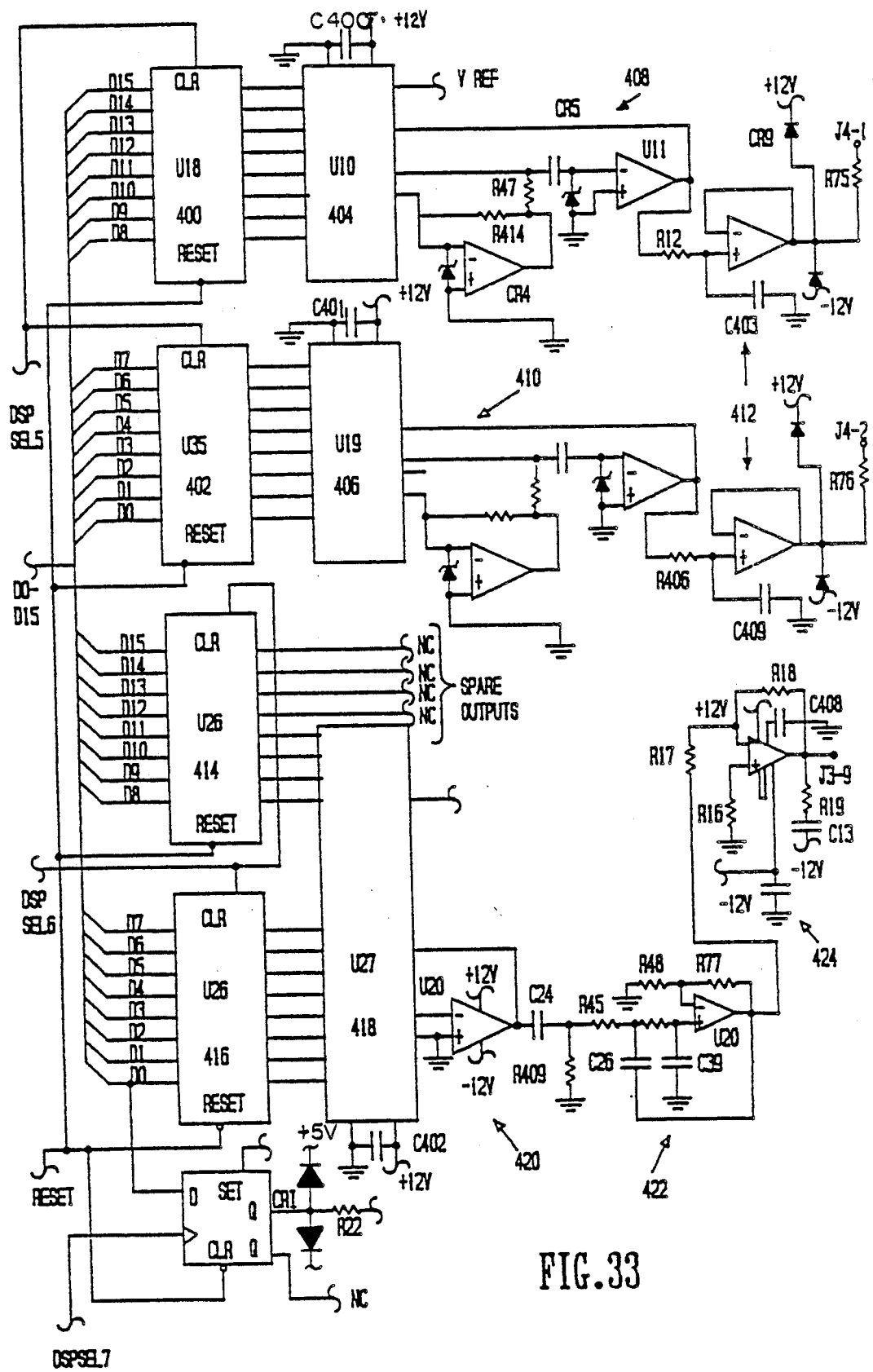
FIG. 33 s a detailed schematic diagram of a fourth portion of the digital signal processing board of the present invention.

The DSP chip 300 can also be used to rasterize data that the main processor subsystem 62 requests in hardcopy form from the laser printer 72. The hardware that translates the digital signals produced by the DSP chip 300 into the signals expected by the laser printer 72 is shown in FIG. 33. Also shown is circuitry that permits an audible signal to be produced in response to the beat data detected by the beat detection program module. This audible signal is particularly useful in the superimposition program module run by the DSP chip 300.

The rasterization hardware consists of octal D flip-flops 400 and 402, which receive digital signals from the data bus of the DSP chip 300. These flip-flops, in turn, provide digital signals to the eight-bit D-to-A converters 404 and 406, which respectively produce a bipolar analog voltage signal after their outputs are passed through current-to-bipolar voltage circuits 408 and 410, respectively. The circuits are protected by buffers 412.

The audible signal circuitry shown in FIG. 33 receives twelve bits from the data output of the DSP chip 300 on the octal flip-flop chips 414 and 416. The twelve digital outputs of the octal D flip-flop chips 414 and 416 are received by the twelve-bit digital-to-analog converter chip 418. The output of chip 418 is converted to a unipolar voltage signal from the output current by circuit 420, the voltage signal being then passed through a 12-kHz, low-pass filter 422, and finally, an audio amplifier 424. The output of the audio amplifier 424 can be connected to a speaker to produce the desirable audible output.

IV. SOFTWARE

A. Main Processor Subsystem Software (AT Software)

This section describes the software that operates on the main processor subsystem 62 to carry out, in part, the methods and systems of the present invention as implemented in the preferred embodiments described herein. This software implements the methods and systems described in the USER INTERFACE section and controls the exchange of programs and data between the main processor subsystem and the DSP board 64.

An executable listing of the main processor subsystem software, which is contained in a file named "holter.exe" in the preferred embodiment described herein, is contained in Appendix I filed herewith. Equivalent programs could be used to accomplish the functions of holter.exe on the same or different computers with equally acceptable results. The development of such programs, given the methods and systems of the present invention, is within the ordinary skill of one in the art. A general description of the operation of this program follows to aid in an understanding of the preferred embodiments.

The operation of the Main Module of the holter.exe program is illustrated in FIG. 34. After the program starts, it reads the configurable system parameters 600. These include, for example, the phrase files which contain the text for the display listings, including those previously described in the USER INTERFACE section and the default diagnosis labels. Other configurable parameters include user preference selections, such as the colors used for color displays.

Next, the program calls the Initialization Module 602, which is illustrated in more detail in FIG. 36 and described below. After initialization is complete, the Main Module calls the appropriate module for the current task 604. For example, if the user has selected Bin Review, the Main Module calls the Bin Review Module as the current task.

Next in flow, the Main Module checks to see if the current task is the system 606. If not, flow returns to the previous step to call the appropriate task. If the system is the current task, it indicates that the user has completed all desired tasks and flow continues to a clean-up step 608 where the mouse is turned off and control of the extended memory (EMS) is returned to the EMS manager. After clean-up, the program terminates 610.

Figure 36:
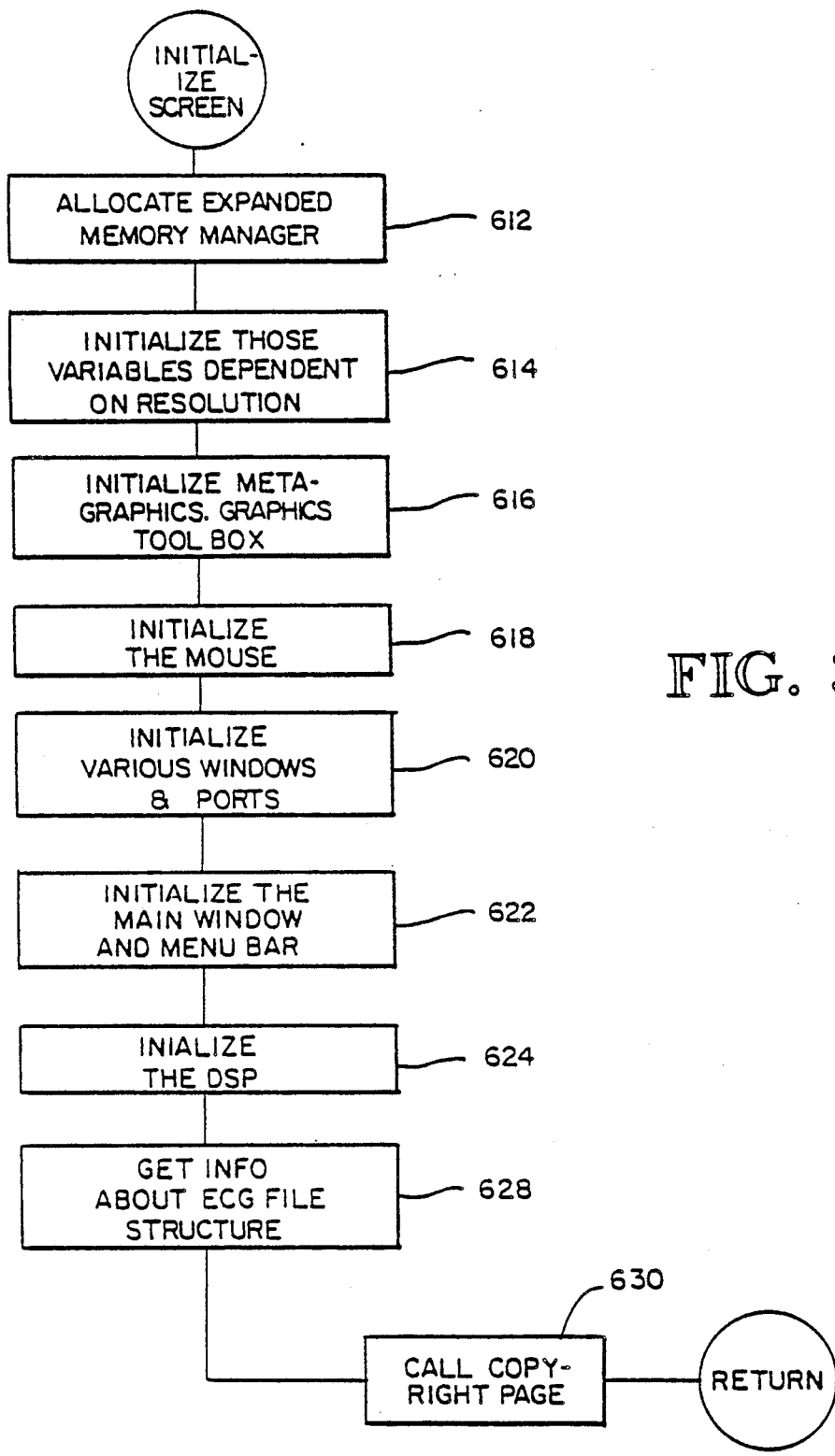
FIG. 36 is a flow chart illustrating the operation of the Initialization Module of a preferred embodiment of the invention.

The Initialization Module is illustrated in the flow chart of FIG. 36. First, the Initialization Module initiates the driver on the expanded memory card 612 in a known manner and in accordance with the manufacturer's instructions. Next, system variables that are dependent on screen resolution are initialized 614. Screen layouts, line widths and the like are preferably specified by variables to allow the system to have optimum displays with display screens of different resolution.

Next, the Initialization Module initializes the graphics tool box 616 used by the system. In the preferred embodiment, a product known as "Metawindows Plus" (1987 Version) by Metagraphics Company of Scotts Valley, Calif., is used as a computer graphics tool box to simplify the generation of system displays. Other comparable tool box products could also be employed or new computer program code written to create the desired displays. A font file from the Metawindows plus product is also read into the system during initialization in the preferred embodiment.

Next, the Initialization Module initializes the mouse 618 and various windows and ports 620 to be used by the system and the Metawindows product.

Flow then moves to initialize the Main Window and Main Menu Bar 622 (see FIG. 2). The DSP board is then initialized 624 and information about the ECG file structure is preferably obtained 626. Because of the size of the ECG file and the fact that it will be stored at various nonsequential locations on the hard disk, it is desirable to provide a means for obtaining access to particular parts of the ECG file more quickly than can be done through the operating system. Relying on the operating system for read/write operations, while effective, will slow operation of the system considerably. The system preferably obtains information from the file allocation table (FAT) regarding the ECG file to enable it to access the ECG file directly rather than through the operating system.

Finally, the Initialization Module calls the copyright page 628 to display various information to the user about the system, including copyright and proprietary notices, logos, etc. Flow is then returned to the Main Module.

Figure 37:
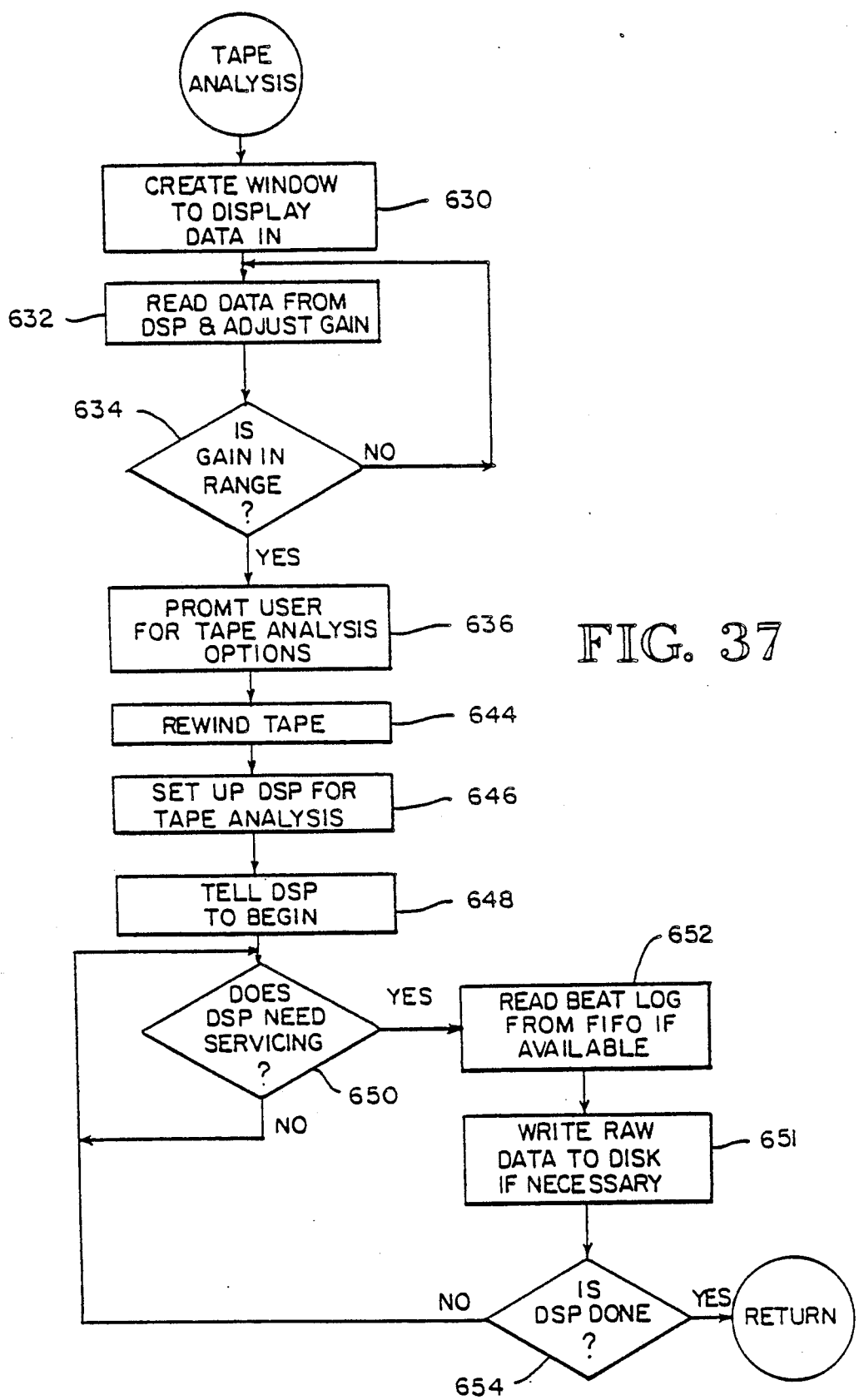
FIG. 37 is a flow chart illustrating the operation of the Tape Analysis Module operating on the main processor of a preferred embodiment of the invention.

The next module typically called by the system is the Tape Analysis Module, illustrated in FIG. 37. This module first creates a window in which to display data and then reads data from the DSP board to adjust the gain 632. If the gain is in the correct range to allow display within the space available 634, the system prompts the user for the tape analysis options 636, as illustrated in FIG. 3. Upon completion of this step, the system runs the Get Tape Loaded Routine, illustrated in FIG. 35, first checking to see if the tape is loaded 638 and then prompting the user to load the tape 640, if necessary.

After confirming that the tape is loaded 642, control returns to the main portion of the Tape Analysis Module to rewind the tape 644 and set up the DSP board 646 for tape analysis Set-up includes loading the DSP tape analysis program and setting flags for the initial conditions. Once set up, the system instructs the DSP board to begin tape analysis 648.

The system services the DSP board to keep its tape analysis under way 650 by continually checking to see if the DSP board has the raw data required to continue the process 651 by checking for downloaded FIFO data. Beat log data is read from the DSP board as it is generated 652. The system continues to service the DSP board until the first pass of tape processing on the DSP board is complete 654, at which time the system control transfers to the AT Pass 2 routine, illustrated in FIG. 38.

The Pass 2 routine initializes the DSP board for the Pass 2 operation on the DSP board, uploading the DSP pass program and setting flags as required 656. The DMA registers of main subsystem (AT) are initialized 658 per standard AT procedures and the FIFOs which will return the beat log data are cleared 660. The system is then forced to the Patient Information Module 662 while disabling the Main Menu.

Figure 39:
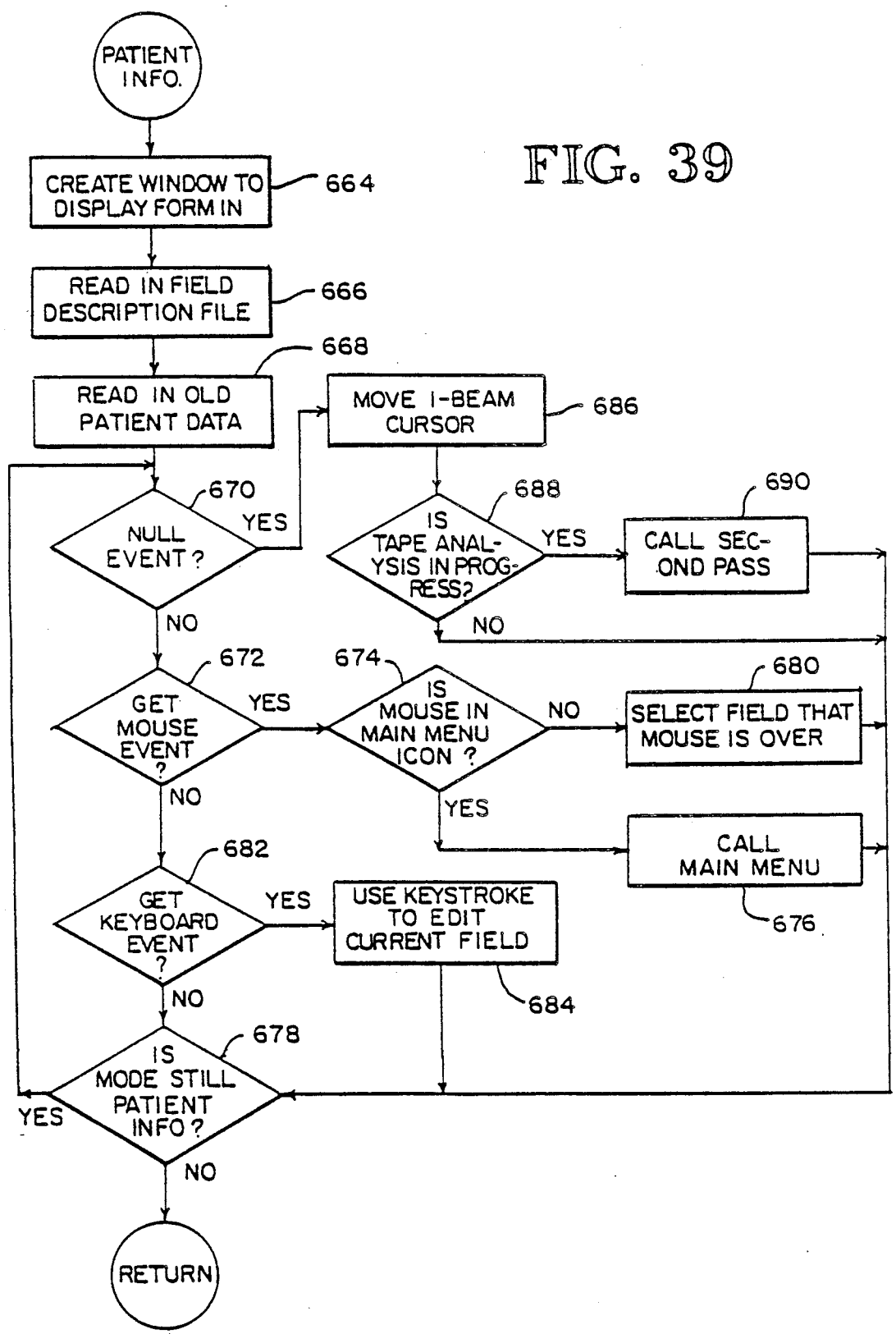
FIG. 39 is flow chart illustrating the operation of the Patient Information Module operating on the main processor of a preferred embodiment of the invention.

The Patient Information Module is illustrated in FIG. 39. In this mode, the system first creates a display window 664, then reads the field description file 66 and any old patient data 668. An initial patient information screen is then created and displayed, as illustrated in FIG. 5.

Figures 38, 40:
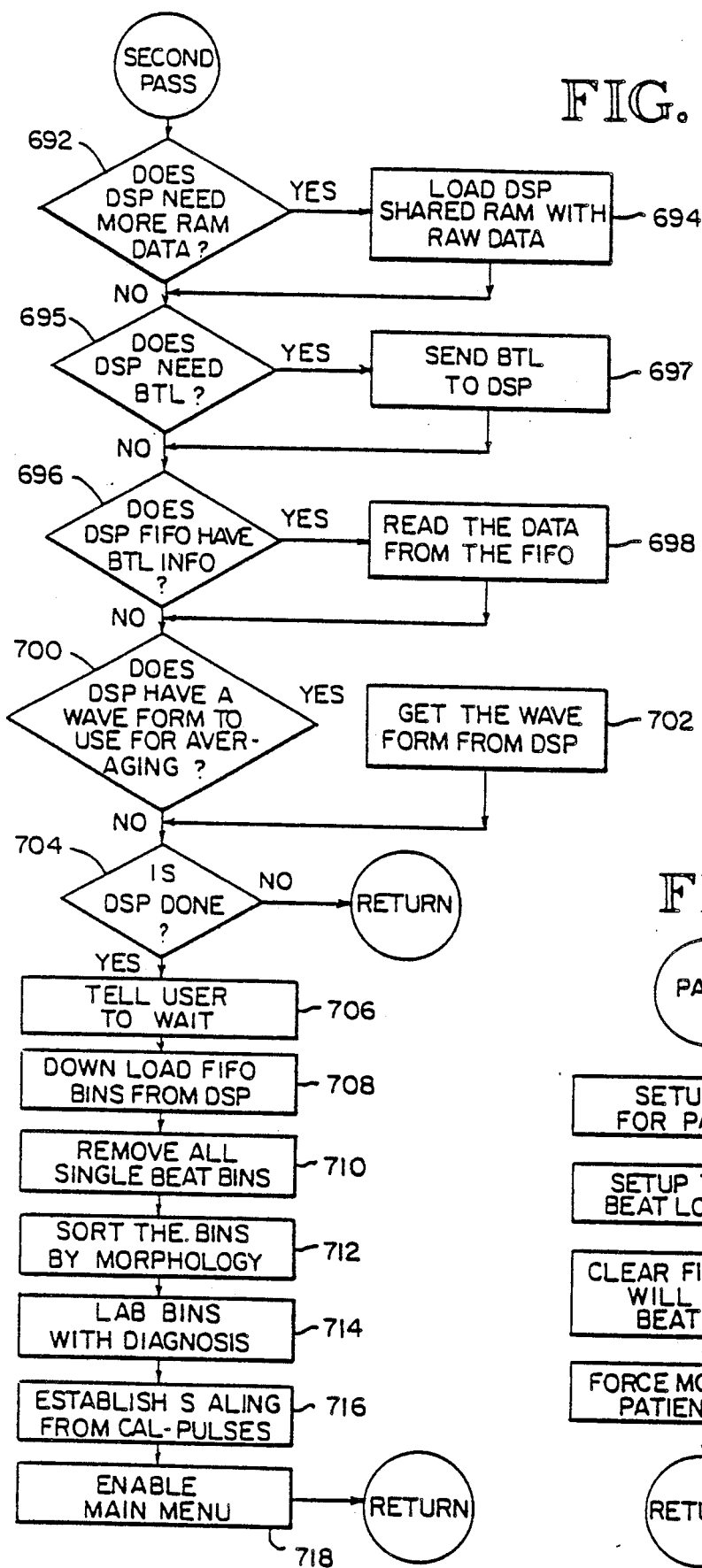
FIG. 38 is a flow chart illustrating the operation of the Pass 2 Routine operating on the main processor of a preferred embodiment of the invention.
FIG. 40 is a flow chart illustrating the operation of the Second Pass Routine on the main processor of a preferred embodiment of the invention.

Once the patient information screen is displayed, the system enters an event loop which enables the user to insert or modify information in the patient information fields while the system continues to service the second pass processing of ECG data on the DSP board and process data therefrom, as illustrated in FIG. 40. The system checks for lack of input activity from the user, or "null events" 670. If mouse input is present 672, the system checks to see if the mouse is in the Main Menu Icon 674. If so, the Main Menu is called 676 and a check is made to see if the system is still in Patient Information Mode 678 (remember that the Main Menu is disabled by the Pass 2 routine), in which case control is returned to the beginning of the event loop 670. If the mouse is not in the Main Menu Icon, then the system selects the patient field over which the mouse is positioned 680 and highlights that field to allow entry of information in that field via the keyboard. As with a Main Menu Icon mouse event, a check is made to see if the system is still in Patient Information Mode, in which case control is returned to the beginning of the event loop. When keyboard events are detected 682, keyboard input is used to edit the current patient information field 684.

When a null event is detected at the beginning of the event loop, the system updates the cursor 686 and then checks to see if the tape analysis is still in process 688. If analysis is still in process, the system transfers control to the Second Pass routine 690.

The Second Pass Routine is illustrated in FIG. 40. Once flow is transferred, the system checks to see if the DSP board needs more digitized ECG data 692. If so, the DSP shared RAM is loaded with additional raw data 694. Next, the system checks to see if the DSP needs BTL information 695 and sends it if necessary 697. The system then checks to see if the DSP FIFO has more BTL information 696. If so, the data is read from the FIFO to the BTL record 698. Next, a check is made to see whether the DSP has a waveform to use for averaging 700. If so, the system retrieves the waveform 702 and stores it for later use.

Next, the system checks to see if the DSP board has completed its analysis of the ECG data. If not, control returns to the Patient Information Module to allow further event processing. If the DSP board has completed the analysis, the system tells the user to wait 706, and downloads the bin information from the DSP board through the FIFO 708. Any single beat bins are then removed 710, the bins are sorted by morphology 712, and bins are labeled with a diagnosis 714. Next, scaling values for each channel are preferably established from the calibration pulses on the ECG data 716. These calibration values are preferably obtained off the tape using a DMA operation. Flow will then return to the Patient Information Module after enablement of the Main Menu 718.

Figure 41:
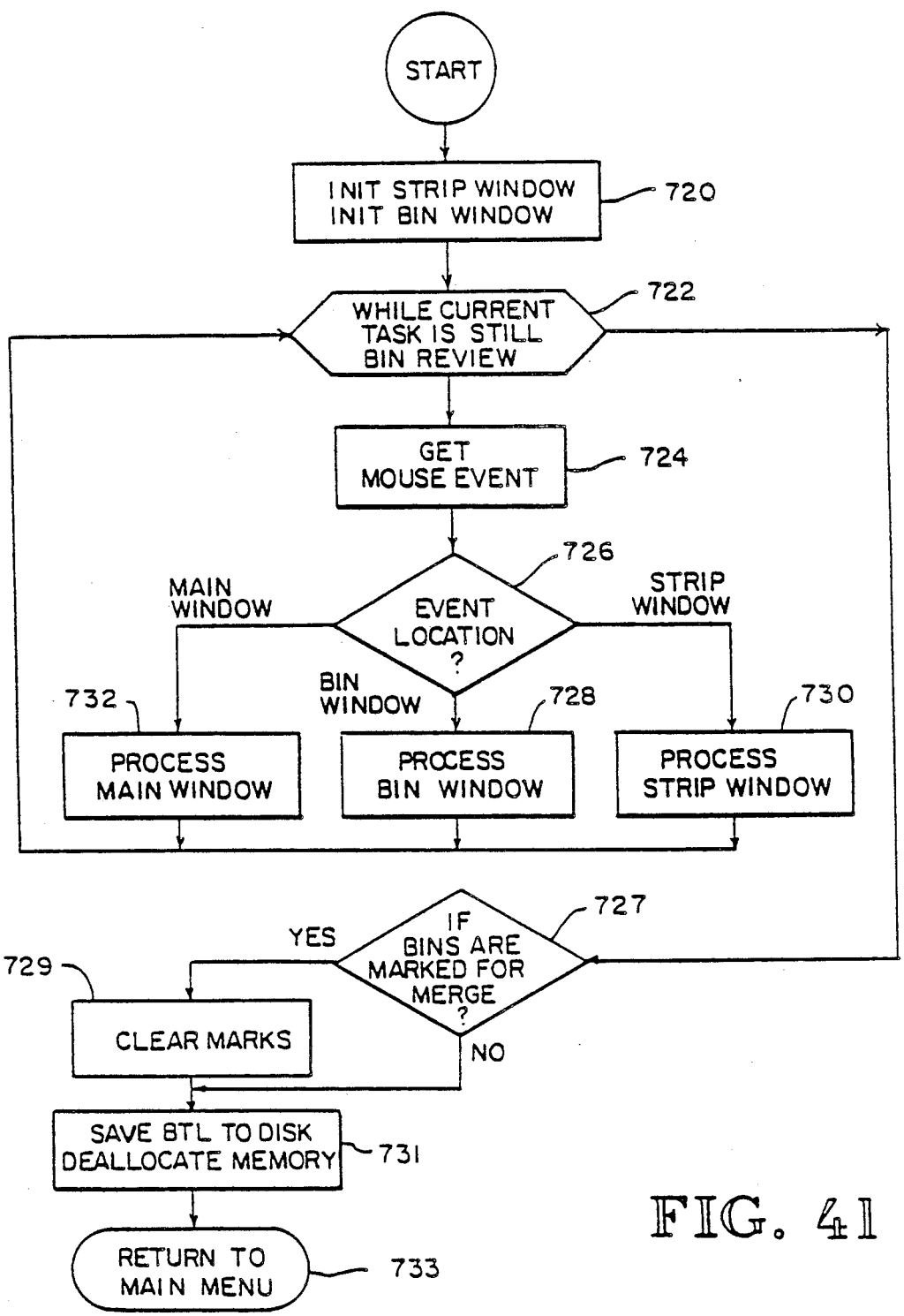
FIG. 41 is a flow chart illustrating the operation of the Bin Review Module operating on the main processor of a preferred embodiment of the invention.

With the Main Menu enabled, the user may exit the Patient Information Module by accessing the Main Menu Icon and selecting a new function. Typically, the user would select Bin Review, causing the system control to transfer to the Bin Review Module, illustrated in FIG. 41. In this mode, the system will first initialize the strip and bin windows 720 and generate a display screen, as illustrated in FIG. 8. While the current task remains in bin review 722, the system will check for mouse events 724 and, when located 726, transfer control to a Process Bin Window Routine 728 if the mouse is in the upper, bin display portion of the screen; transfer control to a Process Strip Window routine 730 if the mouse is located in the lower, real-time strip display portion of the screen; or change the current task, if the user so designates, via the Main Menu 732 and proceed with the Bin Review Module exit steps described below in more detail.

Figure 46:
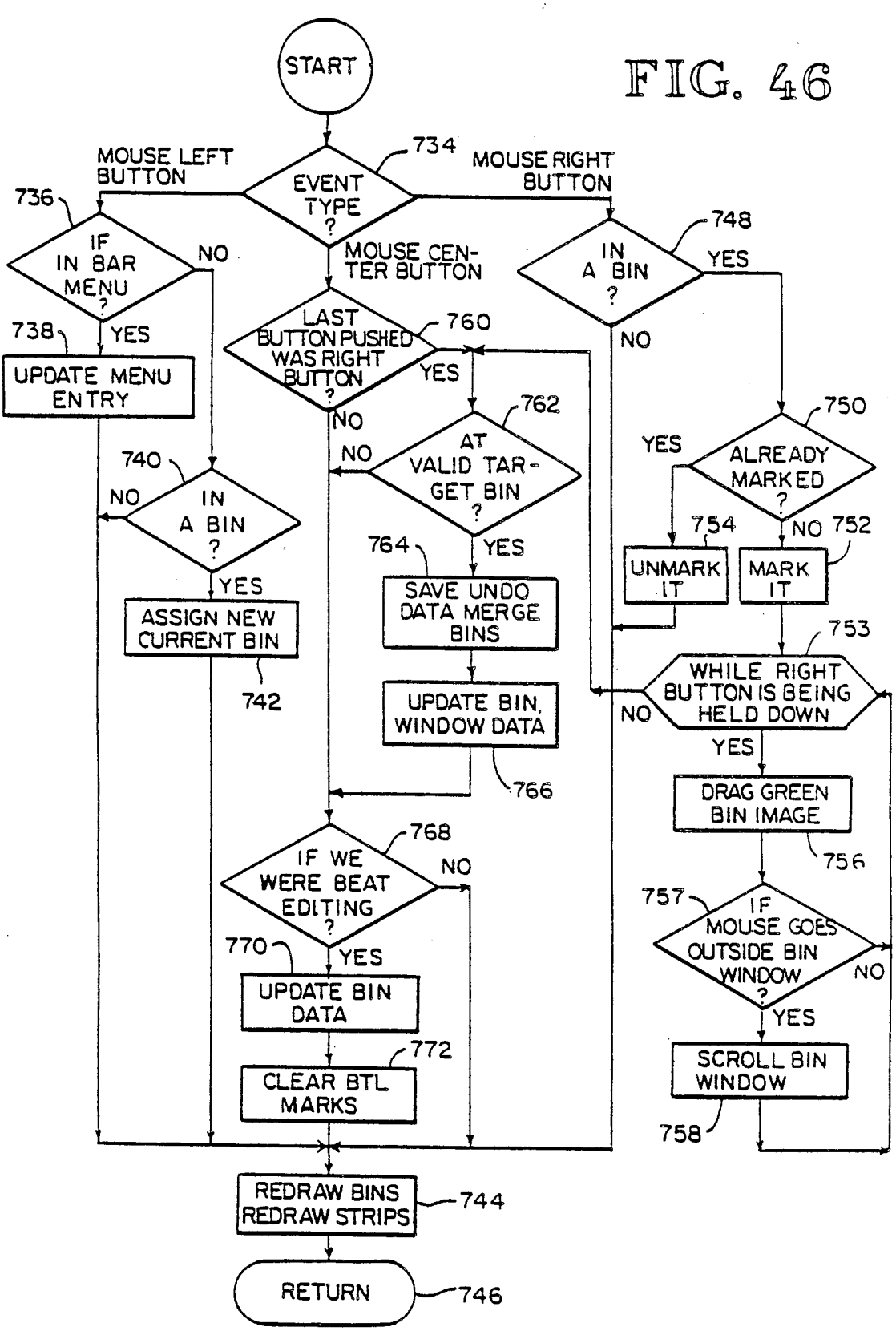
FIG. 46 is a flow chart illustrating the operation of the Process Bin Window Routine operating on the main processor of a preferred embodiment of the invention.

FIG. 46 illustrates the Process Bin Window Routine which handles bin-related user operations in the upper portion of the Bin Review display screen (see FIG. 8). Under this routine, the system first checks for mouse events and categorizes them as either a left, center, or right button event 734. For left button events, the system checks to see if the mouse is in a menu bar 736, in which case the menu entry is updated accordingly 738. If the mouse is not in a menu bar, the system checks to see if it is in a bin display 740, in which case it assigns the bin in which the mouse has clicked to be the new current bin 742. After all checks are made following a left button event, the system redraws the bins and strips 744 to display any changes and returns 746 to the start of the event loop 734.

When a right button event is detected, the system first checks to see if the mouse is in a bin 748. If the mouse is in a bin, the system checks to see if the bin is marked for merging 750 and marks previously unmarked bins 752 or unmarks previously marked bins 754. (Marked bins preferably appear green on the display screen.) If the user continues to hold the right button down, a marked bin can be "dragged" to the current bin 756 (which is highlighted) and the bins merged by releasing the right button. If the mouse goes outside the bin window while dragging a bin 757, the system will scroll the bin window 758. When the right button is released, the system determines whether the mouse is over a valid target bin 762. If so, undo data is stored (to allow the user to undo the merge at a later time) and the dragged bin and target bin are merged 764. Bin and window data are then updated 766 to reflect the merge. Flow then transfers to clear any marks remaining after the merge 772 and to redraw the bins and six-second strips 744, as necessary, and then returns 746 to the Bin Review Module.

An alternate means of bin merging provided in the preferred embodiment is also illustrated in FIG. 46. After a bin is marked 752, if the right mouse button is not held down 753, system control is returned to the Bin Review Module after various checks 760, 768 with negative results. If the user then generates a middle button event, the system will check to see if the right button was the last button pushed 760, and if so, proceed with bin merger if the mouse is over a valid target bin 762 when the middle button is clicked.

When the user selects a new task to exit the Bin Review Mode, the system checks for any bins that are marked for merging 727 and clears the marks 729 if present. The BTL tables, as revised during Bin Review, are saved to the system hard disk with memory reallocation 731 as necessary. Control is then returned to the Main Menu 733.

Figure 42:
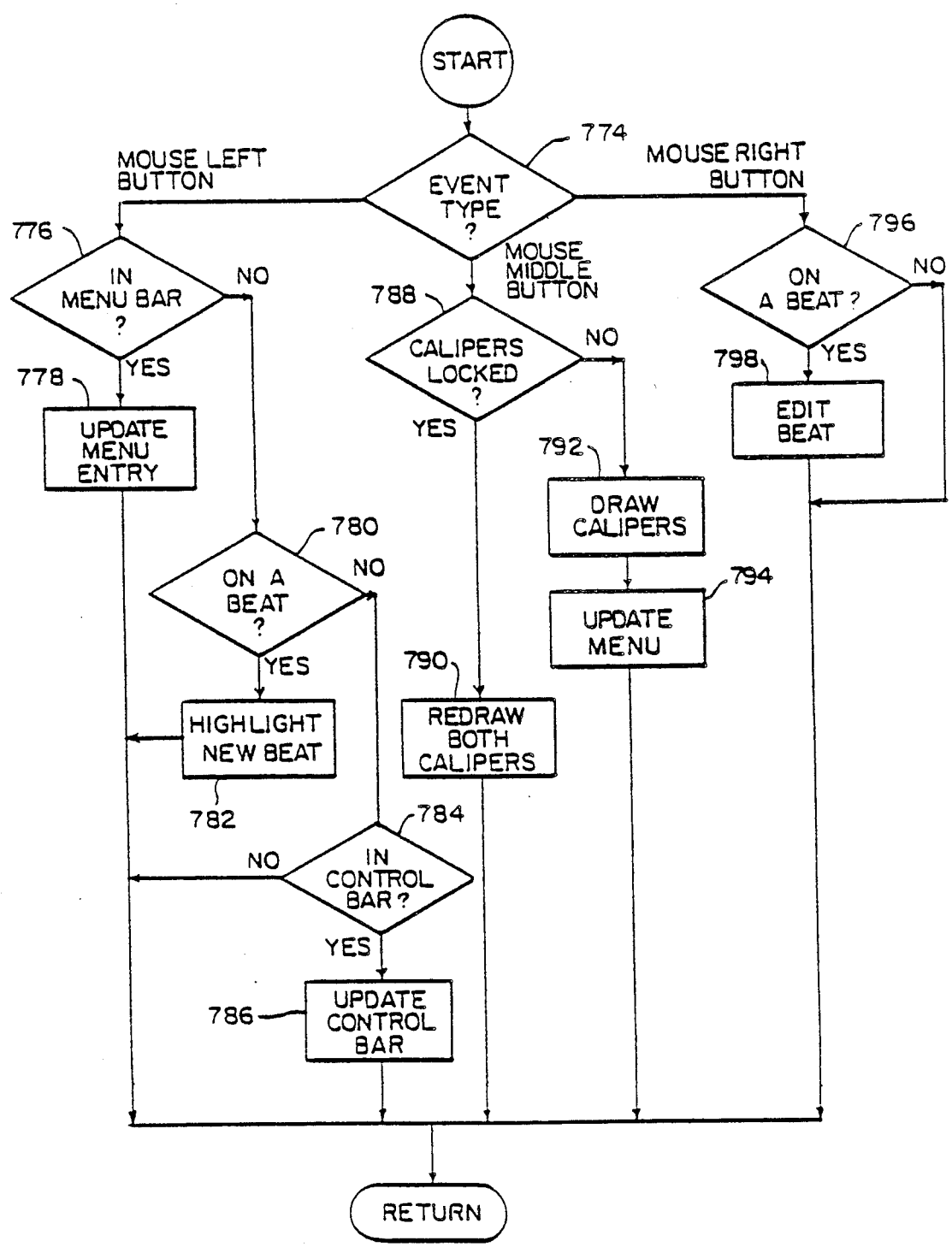
FIG. 42 is a flow chart illustrating the operation of the Process Strip Window Routine operating on the main processor of a preferred embodiment of the invention.

FIG. 42 illustrates the process Strip Window Routine. Under this routine, the system first checks for mouse events 774 to determine if a left, center, or right button event occurs. If a left button event occurs, the system checks to see if the mouse is in a menu bar 776, and if so, updates the menu entry. If the mouse is not in a menu bar, the system checks to determine if the mouse is on a beat 780, and if so, the system increments the centered beat in the real-time display to the next beat in the current, or highlighted, bin 782. If the mouse is not on a beat, the system checks to determine if the mouse is on the control bar 784, and if so, scrolls the real-time data to display the next beat in the current bin in the center of the lower display 786.

If the system detects a center button event, it checks to determine if the calipers are locked 788. If they are locked, the system draws the calipers at the selected locations 790 and calculates and displays the caliper values accordingly. If the calipers are not locked, the system draws the calipers 792 at the locations specified by the user, calculates and displays the caliper values, and updates the caliper menu 794 to lock the calipers at the locations just specified.

If the system detects a right button event, it checks to determine if the mouse is on a beat 796. If the mouse is on a beat, and the user continues to hold down the right button and moves the mouse to a bin on the upper portion of the screen, the beat can be compared to the beats in the bin and recategorized into the bin by releasing the right button while the beat is over the bin. If this dragging and recategorizing occurs, the system will edit the dragged beat 798 as necessary to categorize it in the new bin.

Figure 43:
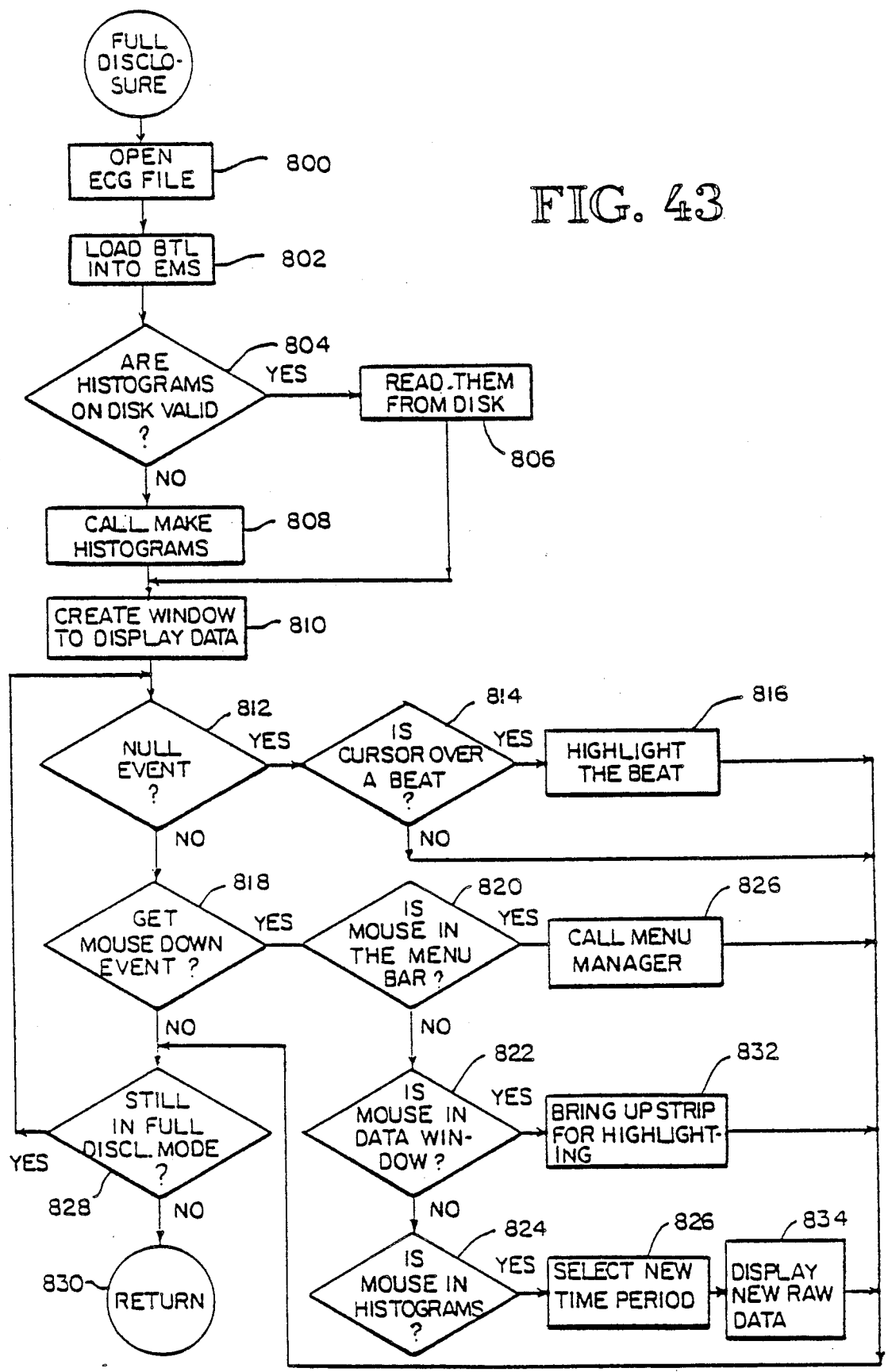
FIG. 43 is a flow chart illustrating the operation of the Full Disclosure Module operating on the main processor of a preferred embodiment of the invention.

In addition to Bin Review, the system will accommodate review of the ECG data in Full Disclosure Module, which is accessed via the Main Menu. The operation of the Full Disclosure Module is illustrated in FIG. 43. In this mode (sometimes referred to as "Histogram Mode" because the ECG data is represented in bar graphs, or "histograms"), the system will first open the ECG file 800 and load BTL information 802 into the extended memory 71 of the main subsystem (AT). Next, the system will check to see if histograms have already been created 804 by checking the histogram files on the hard disk to see if the data there is valid histogram data. If the data is valid, the system will read the existing histograms 806. Otherwise, it will call a routine to generate histograms from the previously generated ECG data 808. When the histograms are available, the system creates a display window 810, which appears substantially as shown in FIG. 23.

From this initial point, the system operates in an event loop to process user commands and display information, as described in the USER INTERFACE section. The system checks for the absence of incoming input from users by checking for null events 812. If there are no events, the system checks to see if the cursor is over a beat 814, and if so, it highlights the beat the cursor is over by placing a box 236 around the beat 816.

If an event is present, the system checks to see if it is a mouse-button-down event 818. If so, further checks are made to see if the mouse is in a menu bar 820, the real-time data window 822, or a histogram 824. When the mouse is in the menu bar, the system calls the Menu Manager 826 and executes the user's instructions accordingly. If the user calls the Main Menu and selects a new mode, control will transfer to that mode 828, 830. If the mouse is in the real-time data window in the lower portion of the display screen, a mouse event will cause the system to bring up a six-second strip 832 centered around the beat that the cursor was on at the time of the mouse event. FIG. 24 illustrates a typical display screen in this mode, with two channels selected for viewing. The system enables the Bin Review functions so that the user can perform Bin Review operations while in Full Disclosure Mode. If the mouse is in a histogram when a mouse event occurs, the system will select a new time period around the selected histogram 826 (a default setting of five minutes is used in the preferred embodiment, with the user able to change the setting via the Scale Menu) and the corresponding raw waveform data will be displayed on the lower portion of the screen 834.

The system remains in the event loop and processes user requests, including Bin Review, if selected, until the user makes a new mode selection via the Main Menu. At such time, the Full Disclosure Module detects the change in mode 828 and transfers control.

Figure 25:
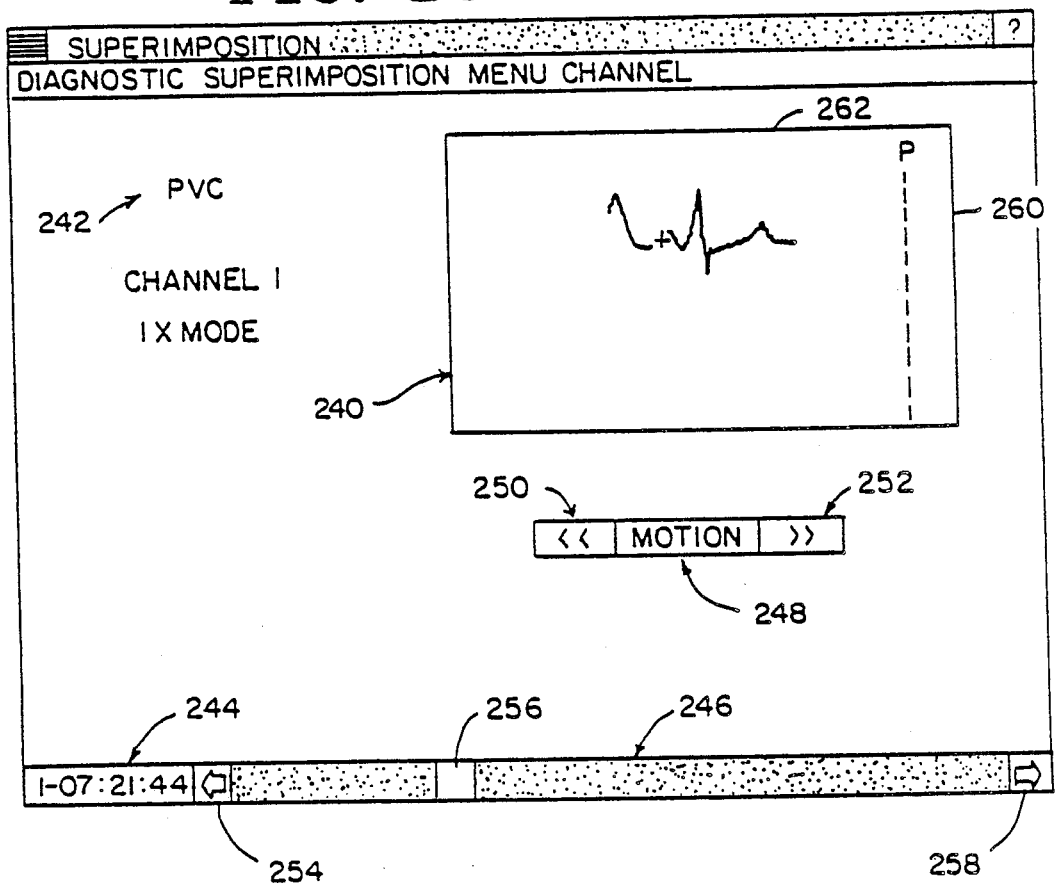
FIG. 25 is an illustration of a screen display from the Superimposition Mode of the preferred embodiment of FIG. 1.
Figure 44:
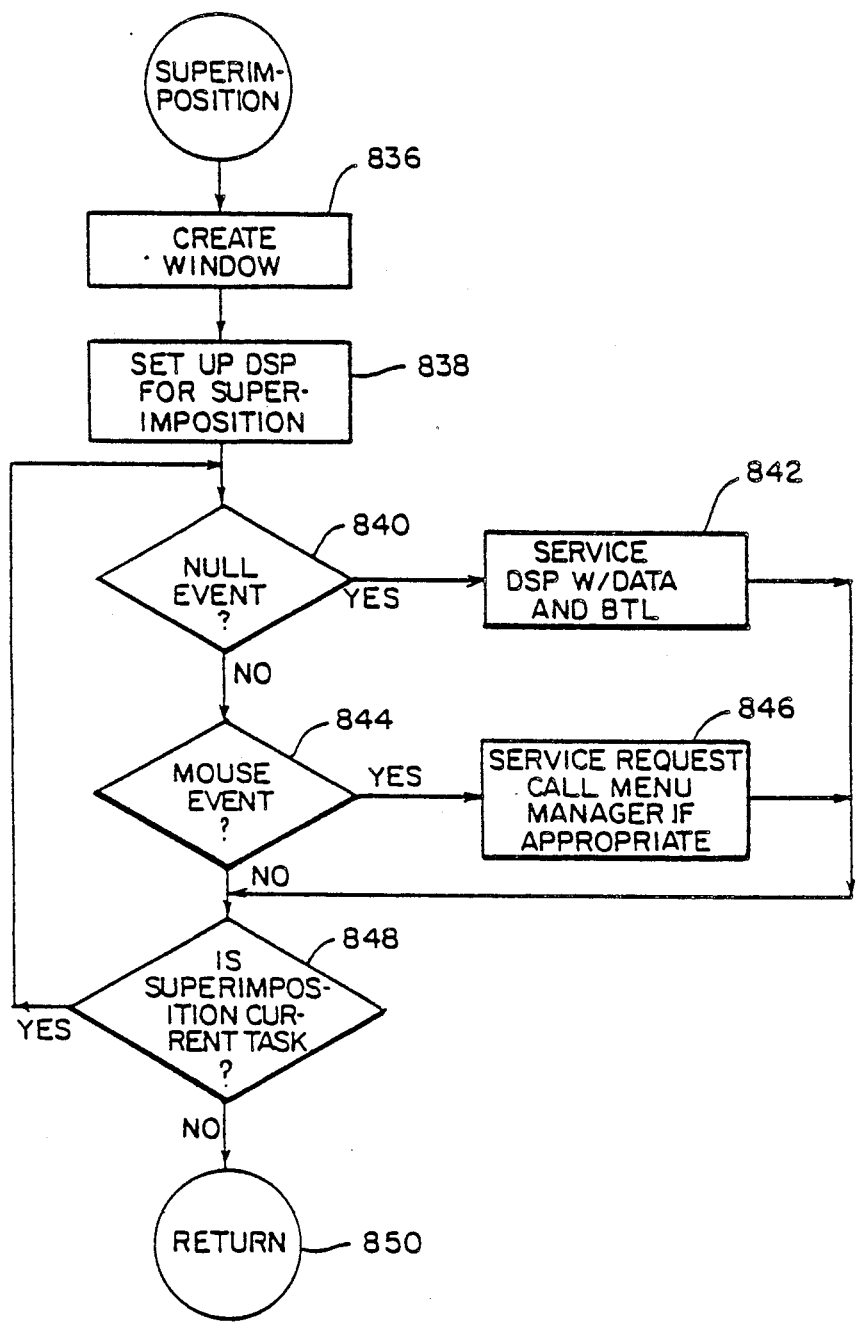
FIG. 44 is a flow chart illustrating the operation of the Superimposition Module operating on the main processor of a preferred embodiment of the invention.

Another major review function available to the user is the Superimposition Mode, which is implemented and controlled by the Superimposition Module, illustrated in FIG. 44. In this mode, the system first creates the Superimposition window 836, including a screen display as shown in FIG. 25. Next, the system sets up the DSP board 838 for the Superimposition operations to be carried out on the board. The generation of waveform displays for sequential display in the beat waveform display area 240 (see FIG. 25) of the screen is preferably performed on the DSP board for increased speed.

After the DSP board is initialized for Superimposition, the Superimposition Module enters an event loop in which it services the DSP superimposition program and services any mouse input from the user. The system checks for events 840, and if none are present, it services the DSP board with raw data and BTL data as necessary 842. Waveform display data is taken from the DSP for display on the screen. If an event occurs, the system determines if it is a mouse event 844, and if so, calls menus and corresponding functions as appropriate 846. At the end of the event loop, the system determines if Superimposition is still the current mode 848 and either reenters the event loop or returns control to the Main Menu as appropriate 850.

Figure 45:
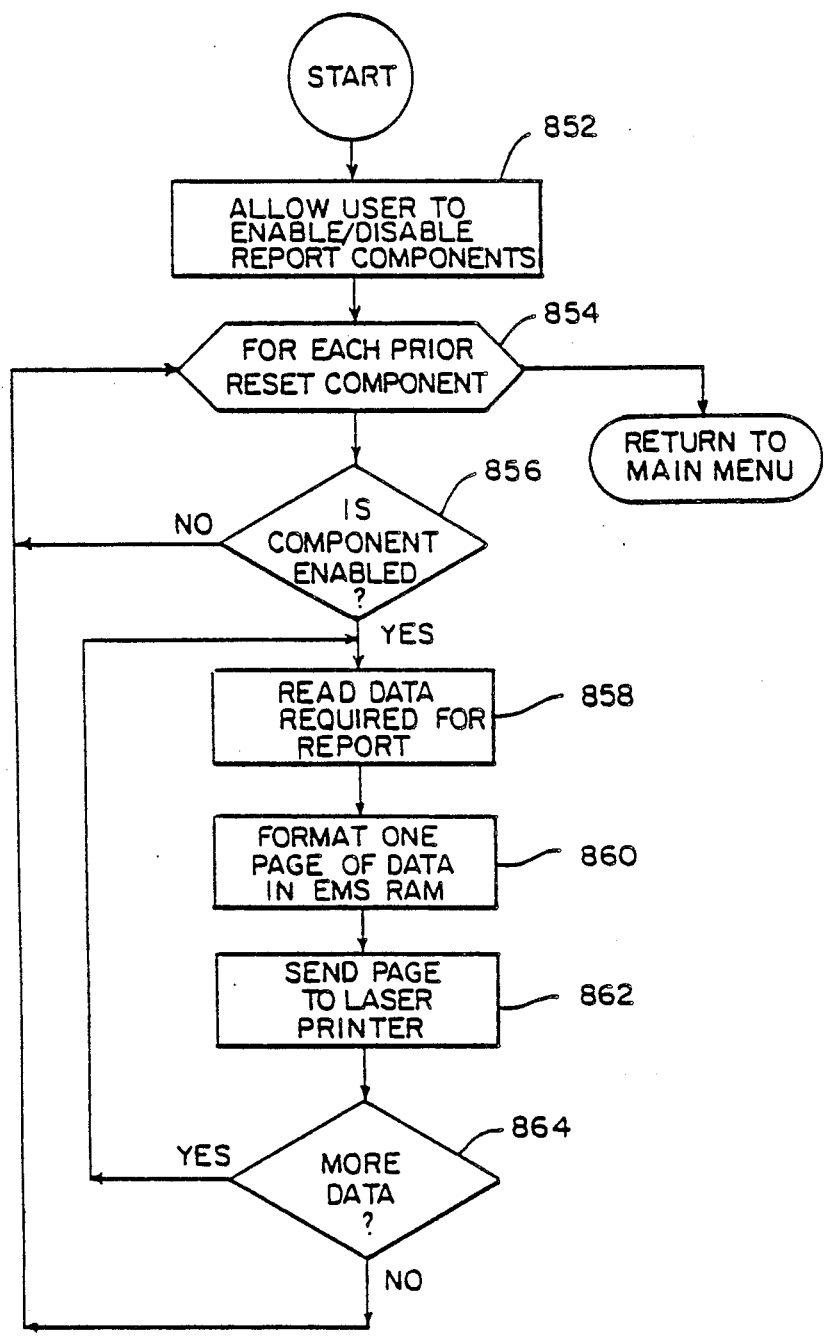
FIG. 45 is a flow chart illustrating the operation of the Reports Module operating on the main processor of a preferred embodiment of the invention.

The preferred embodiment includes a mode for generating reports on the patient and ECG analysis as illustrated in FIG. 45. In this mode, the system first allows the user to enable or disable report components 852. For each reset component 854, the system determines if the component is enabled 856, and if so, reads the data required for the report 858, formats a page of the data in the extended memory 860, and sends the page to the laser printer 862. If there is more data 864, the systems returns to read and format addition pages of data.

B. Digital Signal Processing

FIGS. 47A-E show flow charts for the DETECT module. An executable listing of a program, passl.dsp, is provided in Appendix II. The DETECT module is used by the DSP chip 300 to get data from the tape player and detect heartbeats on the first pass through the data. The module contains a large loop which inputs a pair of data values and checks the sequence of data for noise. The module then checks for a positive deflection, followed by a negative deflection (or vice versa) of the signal in either channel, with the amplitude and interval of the wave formed by the data in either channel being consistent with the occurrence of a heartbeat. If a heartbeat (or "beat") is found, its data is placed in the end of a beat queue. The module then processes the new data in the beat queue and causes the data to be stored in the beat time log, if appropriate.

It will be understood by those skilled in the art that the data of channel 2 is treated in the same way by the module DETECT as is the data in channel 1. The treatment of the channel 2 data has been omitted wherever possible throughout this description to retain brevity.

The DETECT module begins by performing housekeeping operations connected with power-up 900. Next, the program initializes values which it will use subsequently (902). The module then branches to subroutine GETDAT (903).

Figure 48:
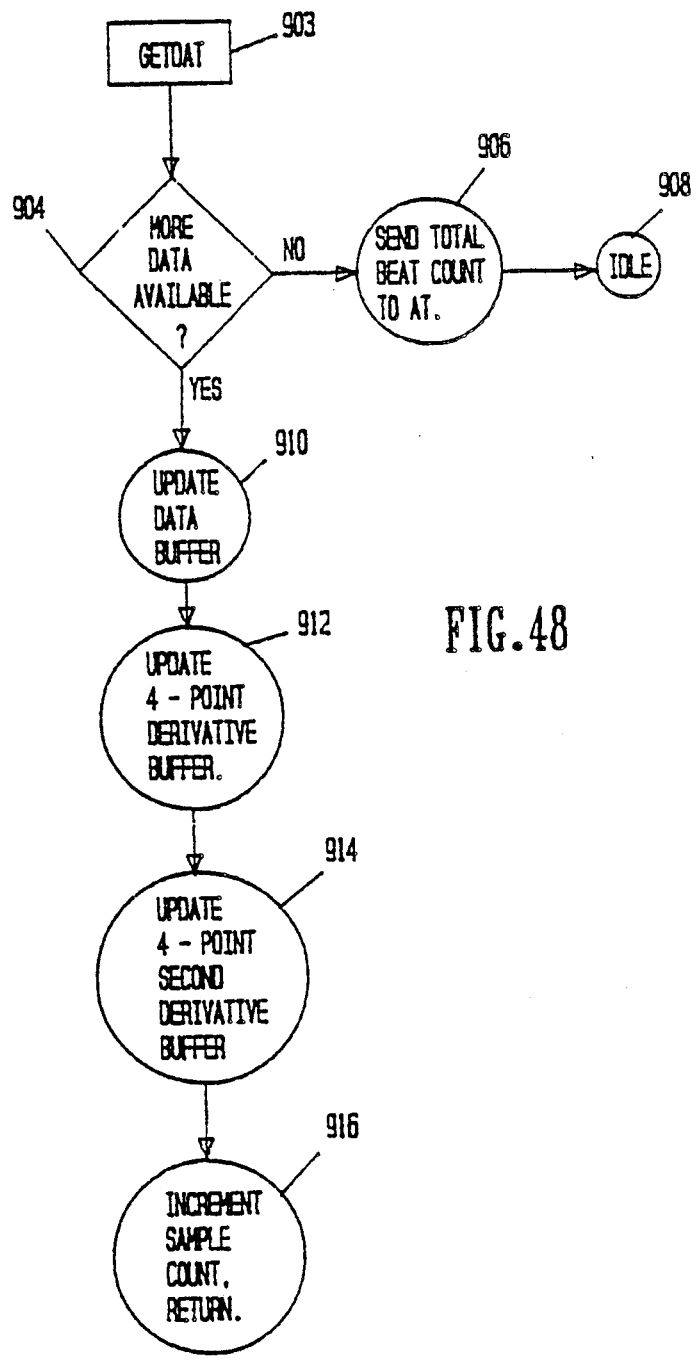
FIG. 48 is a flow diagram of the GETDAT subroutine of the digital signal processing chip software.

The flow chart for the subroutine GETDAT is shown in FIG. 48. GETDAT first checks to see whether further data is available from the tape player (904). If no further data is available, the program sends the total beat count to the main processor subsystem 62 (906) and enters the idle state 908, where the DSP chip 300 waits to begin a second pass through the data. If, on the other hand, more data is available, the data buffer is updated (910).

The data is also processed to calculate a four-point derivative, which is the difference between the value of the waveform at the present sample and its value four samples in the past This data is paced in a four-point derivative buffer 912. Further, a four-point second derivative is calculated and stored in a four-point second derivative buffer 914. The four-point second derivative is the difference between two consecutive four-point derivatives. The subroutine GETDAT then increments the sample count and returns to the subroutine call 903 in the DETECT module 916.

Figure 49:
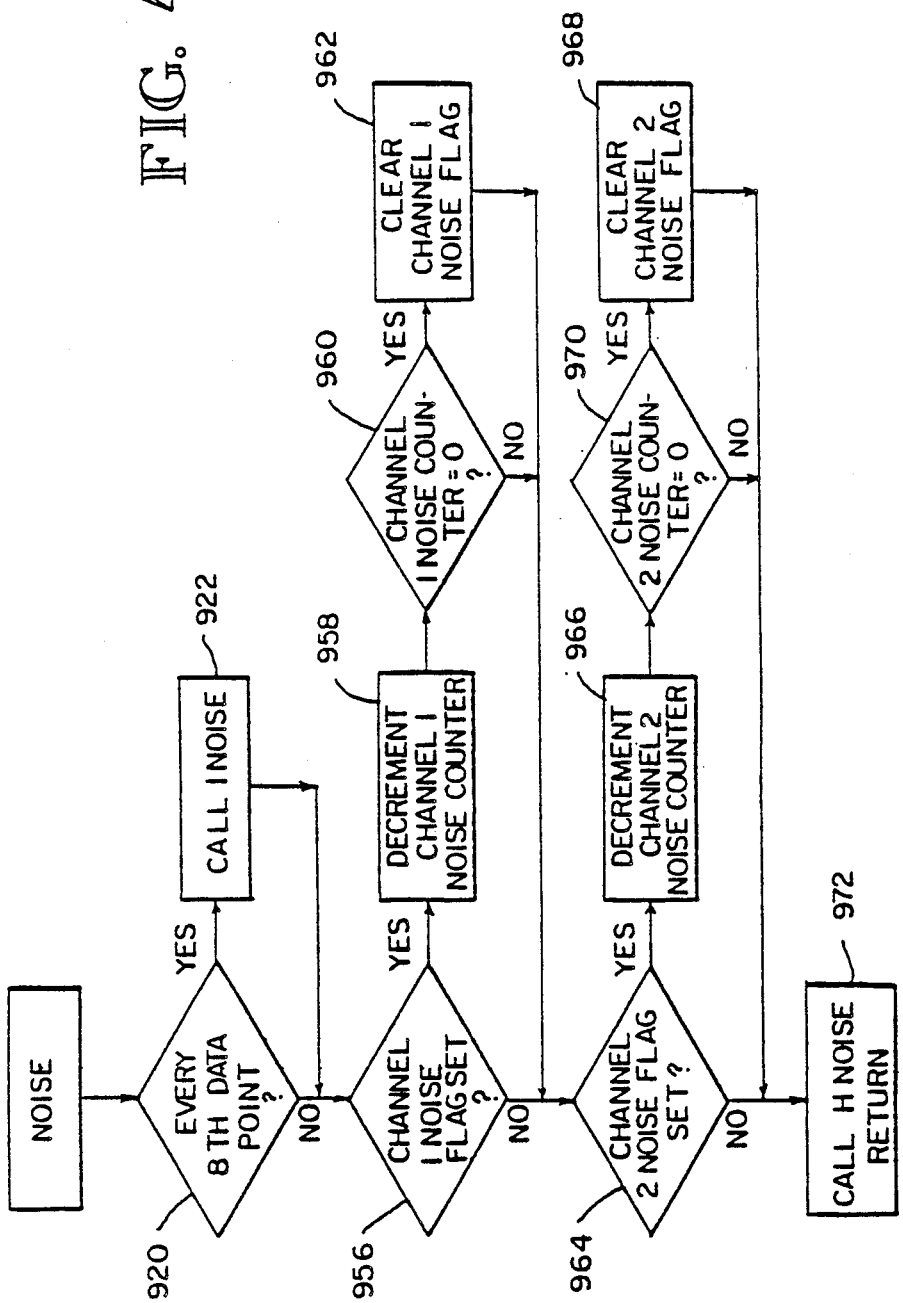
FIG. 49 is a flow diagram of the NOISE subroutine of the digital signal processing chip software.
Figure 50:
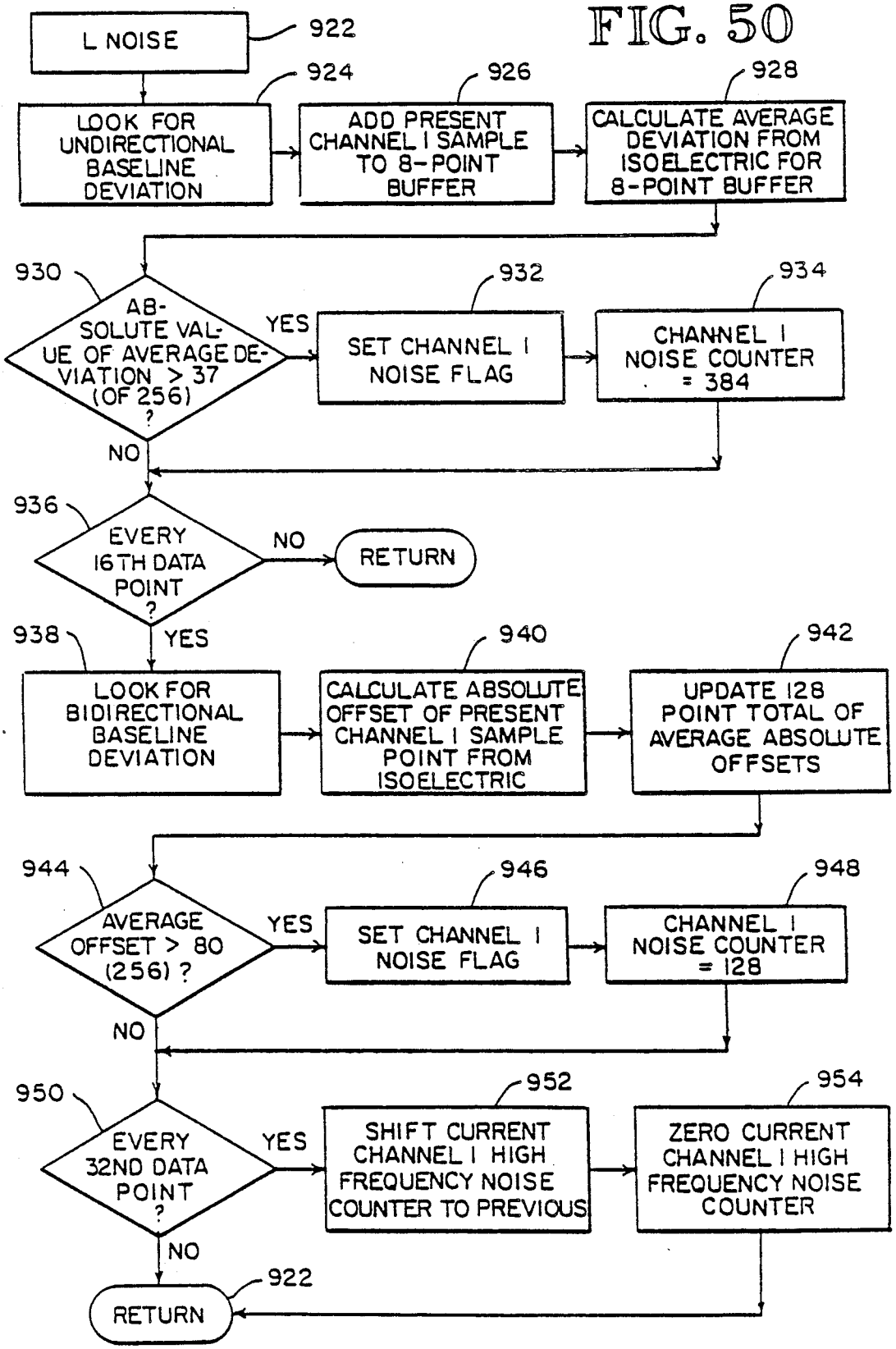
FIG. 50 is a flow diagram of the LNOISE subroutine of the digital signal processing chip software.

Returning to the subroutine call at 903, DETECT next calls subroutine NOISE 918. The purpose of subroutine NOISE, whose flow chart is shown in FIG. 49, is to manage calls to high- and low-frequency noise detection subroutines and to manage corresponding noise counters. Accordingly, the program uses every eighth data point sample, as determined by decision block 920, to make a low-frequency sampling of the data. If a particular sample is the eighth data point since the last low-frequency noise sample was taken, program control passes to the subroutine call 922 and subroutine LNOISE (see FIG. 50). LNOISE scans the low-frequency data 924 to look for unidirectional baseline deviations. If these deviations are found, LNOISE causes the present data sample to be added to an eight-point buffer 926.

The data in the eight-point buffer is then used by subroutine LNOISE to calculate the average deviation from the isoelectric baseline 928. In decision block 930, the absolute value of the average deviation calculated in step 328 is compared to 37 (out of a possible maximum of 256). If the absolute value of the average deviation exceeds 37, control of the program passes to 932, where the channel 1 noise flag is set (indicating that low-frequency noise has been detected). Next, 934, the channel 1 noise counter is set to a value of 384.

At this point, program control passes to decision block 936, regardless of the outcome of decision block 930. If the data sample just taken represents a sample taken every sixteenth data point, program control is retained by subroutine LNOISE. Otherwise, program control returns to subroutine call 922 in the subroutine NOISE (see FIG. 49).

Assuming that the data sample just taken is the sixteenth data point to occur since the last sample of this sort has been taken, program control continues in subroutine LNOISE. Here, the data taken by sampling every sixteenth data point is scanned to look for a bidirectional base line deviation 938. The absolute value of the offset of the present channel 1 sample point from isoelectric is calculated 940. This value is used to update a 128-point total of average absolute offsets 942.

In decision block 944, the value of the average offset is compared to 80. The average offset cannot exceed 256. If the average offset does exceed 80, program control passes to step 946, where a noise flag is set for channel 1, indicating that the bidirectional noise has become significant. Subsequently, the channel 1 noise counter is set equal to 128 (948). Regardless of the outcome of the test in decision block 944, program control then passes to decision block 950, where it is determined whether the current data point is the thirty-second data point since the last sample was taken. If it is, the current channel 1 high-frequency noise counter (to be described subsequently) is set to its previous value (952).

Next, the channel 1 high-frequency noise counter is zeroed 954. Regardless of the outcome of the test 950, program control then returns to subroutine call 922 (see FIG. 49).

Regardless of the outcome of decision block 920, program control in subroutine NOISE next passes to decision block 956 (see FIG. 49), where the channel 1 noise flag is tested. If the noise flag is set, program control passes to step 958, where the channel 1 noise counter is decremented by one count. A test is then performed by decision block 960 to determine whether the channel 1 noise counter has reached zero. If it has, the channel 1 noise flag is cleared 962.

Regardless of the outcome in decision block 960, program control next passes to decision block 964. At this point, a test of the channel 2 noise flag is performed. The channel 2 noise flag test is analogous to that just described in connection with steps 958 and 962 in decision block 960. Steps 966 and 968 in decision block 970 are the counterparts to the steps in decision blocks just described in connection with the channel 1 noise flag test. Program control then passes to subroutine call 972, where the HNOISE subroutine is called.

Figure 51:
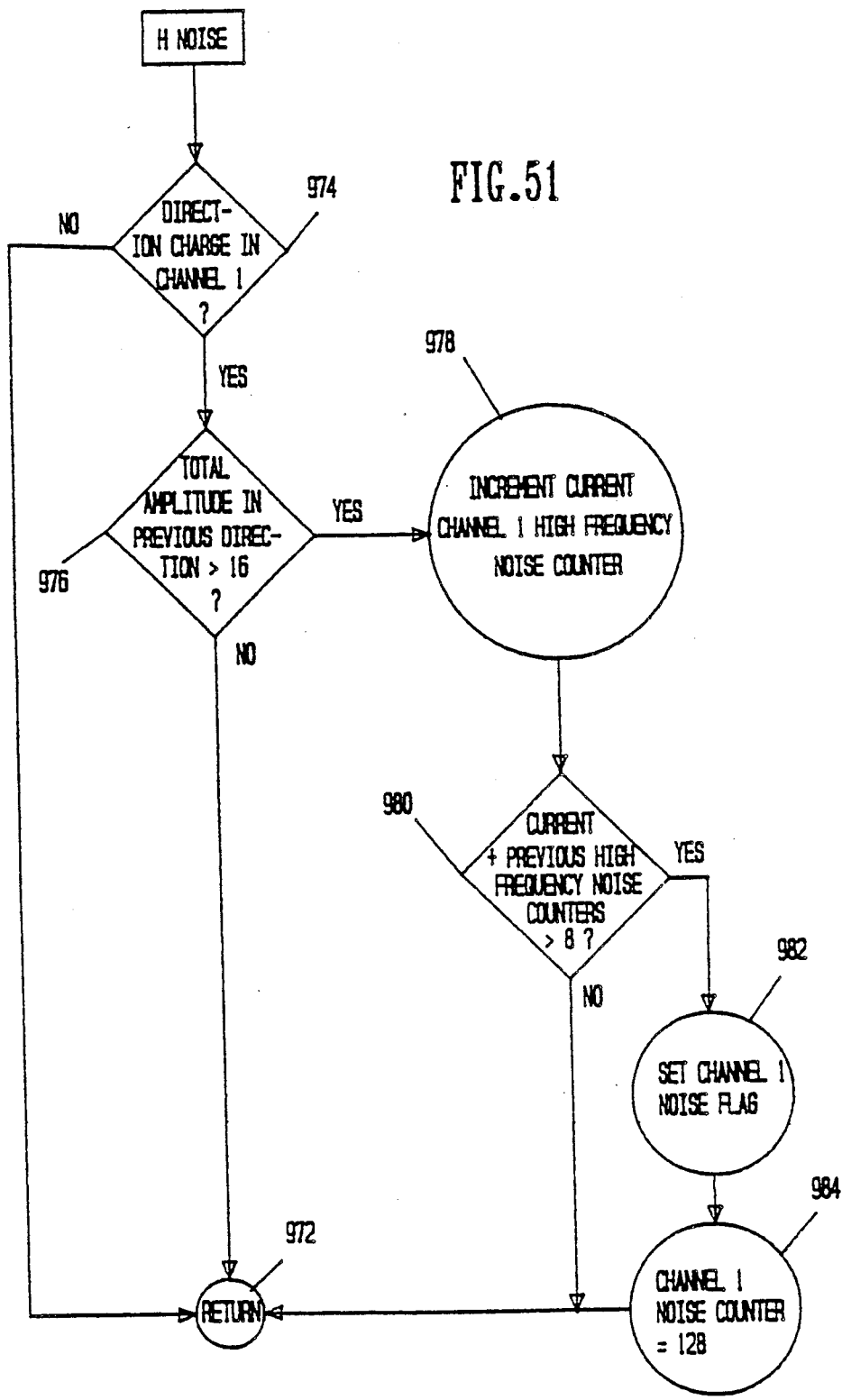
FIG. 51 is a flow diagram of the HNOISE subroutine of the digital signal processing chip software.

As shown in FIG. 51, the flow chart for the subroutine HNOISE first contains a decision block 974. In decision block 974, the channel 1 data is checked to etermine whether the direction of the most recent data samples has changed If it has not changed, there cannot be high-frequency noise and program control then passes to the return in subroutine call 972 (see FIG. 49). Program control therefore returns to subroutine call 918 (see FIG. 47A). If, on the other hand, the recent data has changed direction in channel 1, there may be high-frequency noise present and program control passes to decision block 976, where the total amplitude in the previous direction is compared to 16. If it does not exceed 16, program control passes to step 972, where control returns to the DETECT module, whose flow chart is shown in FIGS. 47A-E. Otherwise, the channel 1 high-frequency noise counter is incremented by one count (978) and a test is performed to see whether the sum of both of the current and previous high-frequency noise counters exceeds eight 980. If it does, the channel 1 noise flag is set (982) and the channel 1 noise counter is set equal to 128 (984). Regardless of the result of decision block 980, program control now passes to step 972, which returns control of the program to the call for the subroutine NOISE (918) in FIG. 47A.

Continuing with the DETECT module, the program next performs a test 986. The variables involved in the decision block 986 are the current and next most-recent values ($S_1$) of the differences between the last two four-point derivative ($D_1$) values of channel 1. The test performed 986 is to determine whether the sign of the current value of $S_1$ differs from the sign of the next most-recent value of $S_1$. If the signs do not differ, the sign of the derivative has not changed and program control passes to the decision block 988.

In decision block 988, it is determined whether the most recent value of the four-point derivative peak ($P_4$) was positive. If the most recent value of $P_4$ was positive, program control passes to decision block 990, where the most recent channel 1 raw data value ($R_1$) is compared to the highest channel 1 raw data value since the most recent positive four-point derivative peak ($P_1$). If $R_1$ exceeds $P_1$, program control passes to step 992 since a new peak value in the channel 1 raw data has been reached, and the $P_1$ value is reset to reflect this fact. In addition, the time of the most recent positive four-point derivative peak is reset 992, to be equal to the time of the present raw data value.

If, as determined by decision block 988, the last value of $S_1$ was negative, program control passes to decision block 994, where $R_1$ and $P_1$ are also compared. In this case, if $R_1$ is more negative than the current $N_1$, the most negative recent raw data value is updated by the most recent raw data value 996. Regardless of the answer in the decision block 988, program control then passes to the call to subroutine GETDAT 903, where the next data point is obtained.

Referring again to the decision block 986, if the sign of $S_1$ changed from the previous value of $S_1$ to the present value of $S_1$, the program passes to decision block 998. If the current value of $S_1$ is positive, the program passes to decision block 1000, while if it is not positive, the program passes to decision block 1002. In decision block 1000, the previous value of a four-point derivative ($D_1$) is compared to 12. If the previous value of $D_1$ did not exceed 12, program control passes to decision block 988, while if the previous value of $D_1$ exceeded 12, program control passes to the decision block 1004 (in FIG. 47B).

In decision block 402, the previous value of $D_1$ is compared to a negative 12. If the previous value of $D_1$ is less than $-12$, program control passes to decision block 1006 (see FIG. 47D). If neither of the tests in decision block 1000 and decision block 1002 is passed, the previous value of the four-point derivative was not sufficiently extreme, and control passes to the decision block 988 (in FIG. 47A).

Figure 47A:
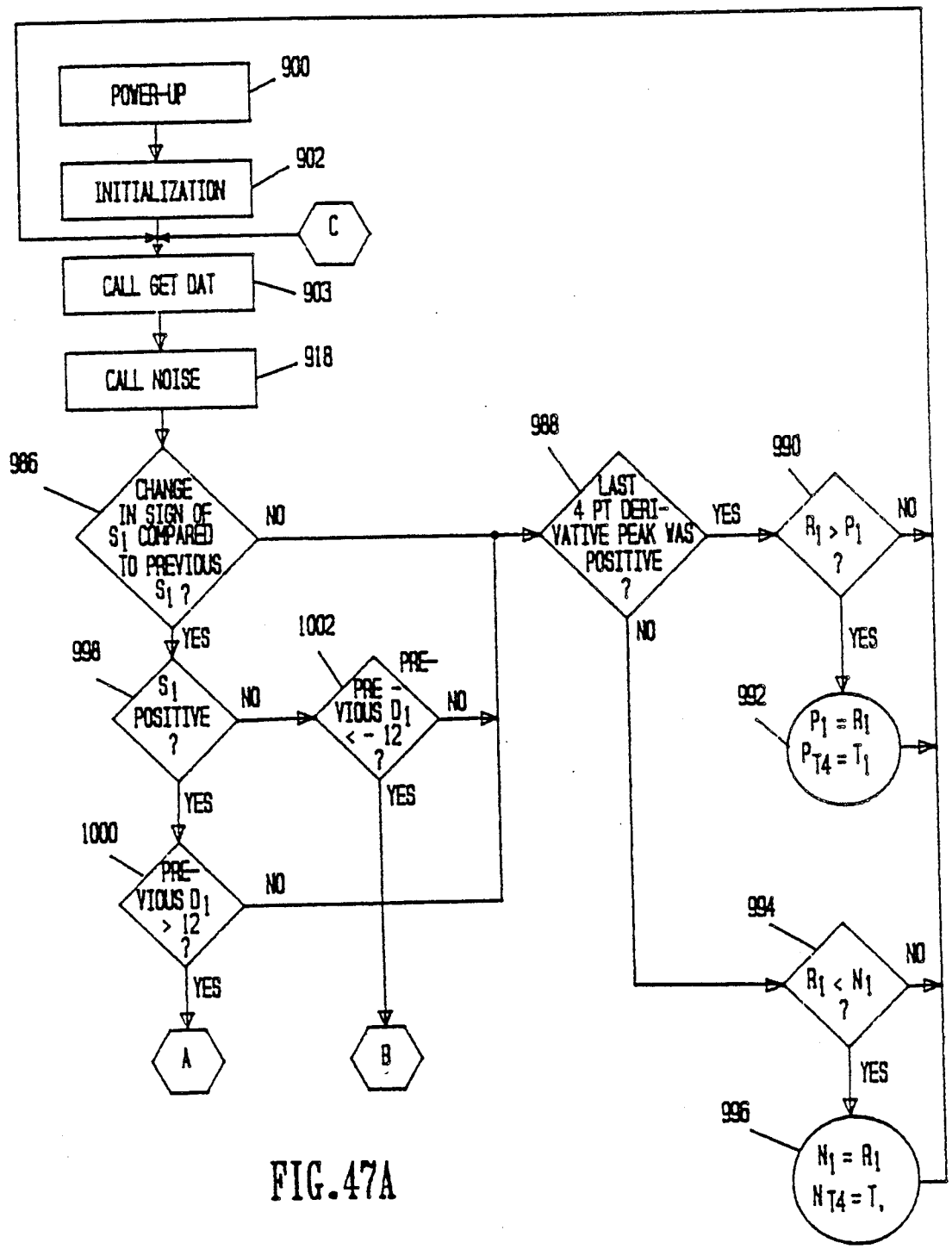
FIG. 47A is a first portion of a flow diagram of the DETECT module of the digital signal processing chip software.
Figure 47B:
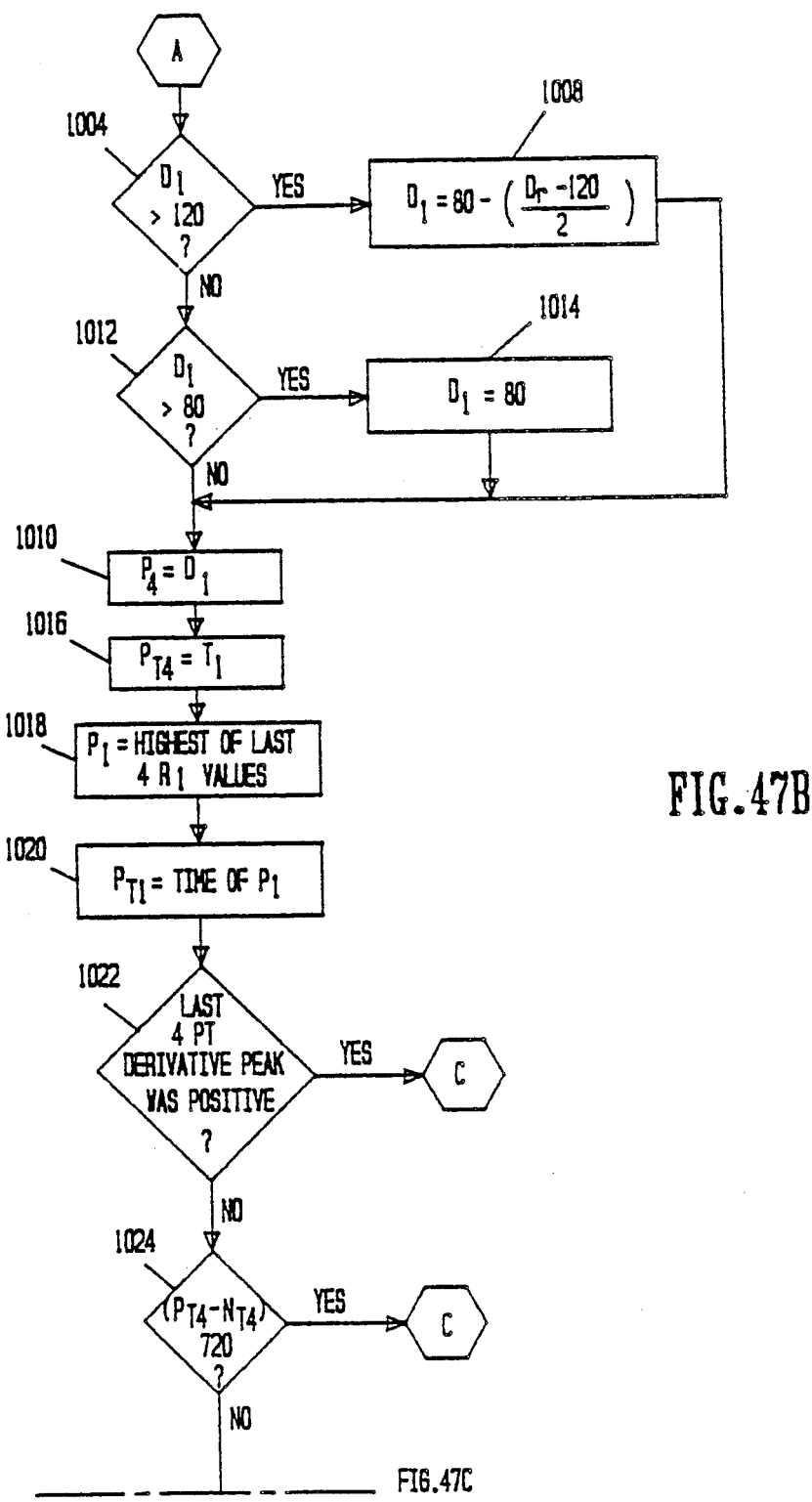
FIG. 47B is a second portion of a flow diagram of the DETECT module of the digital signal processing chip software.
Figure 47D:
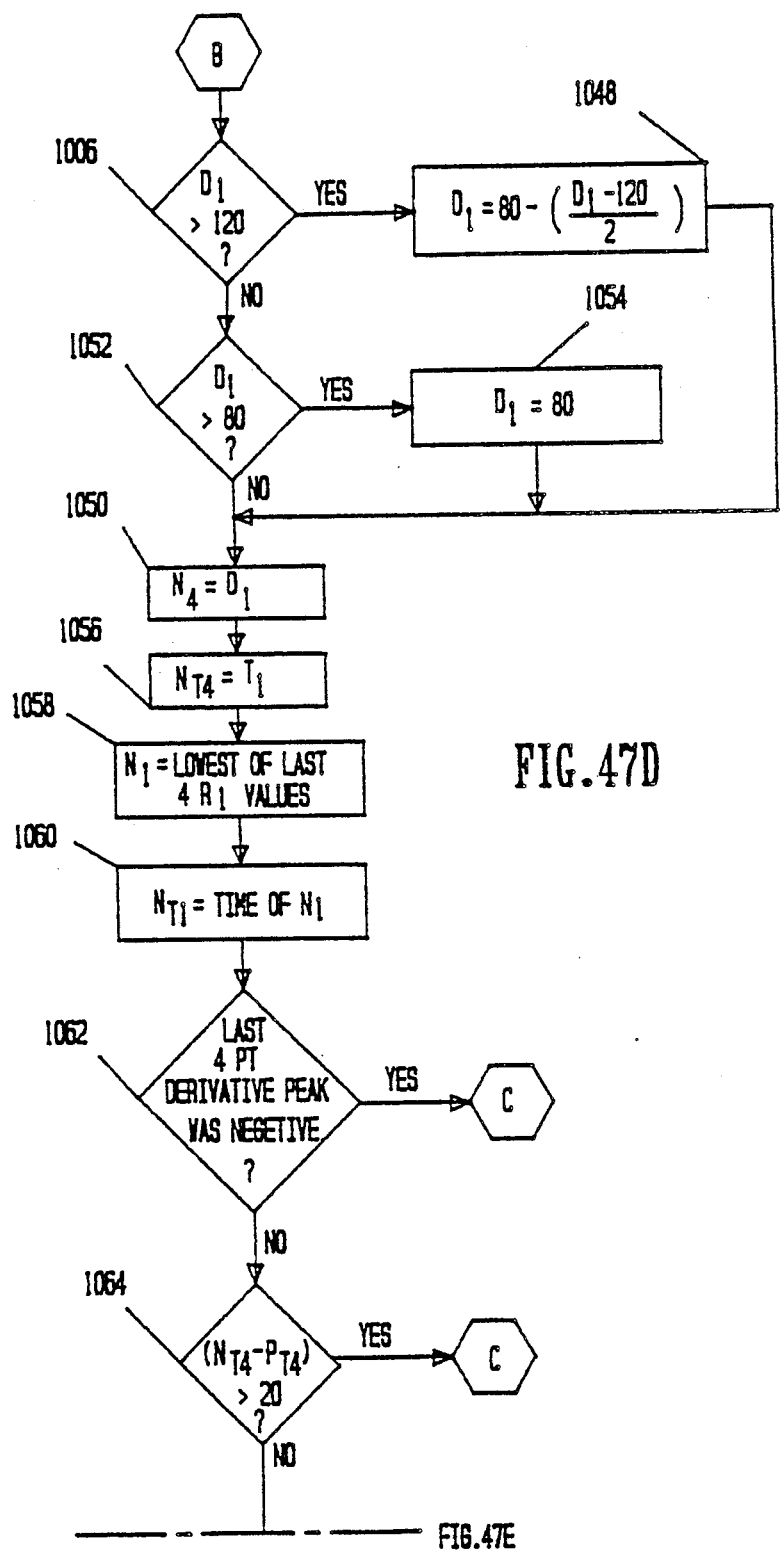
FIG. 47D is a fourth portion of a flow diagram of the DETECT module of the digital signal processing chip software.
Figure 47E:
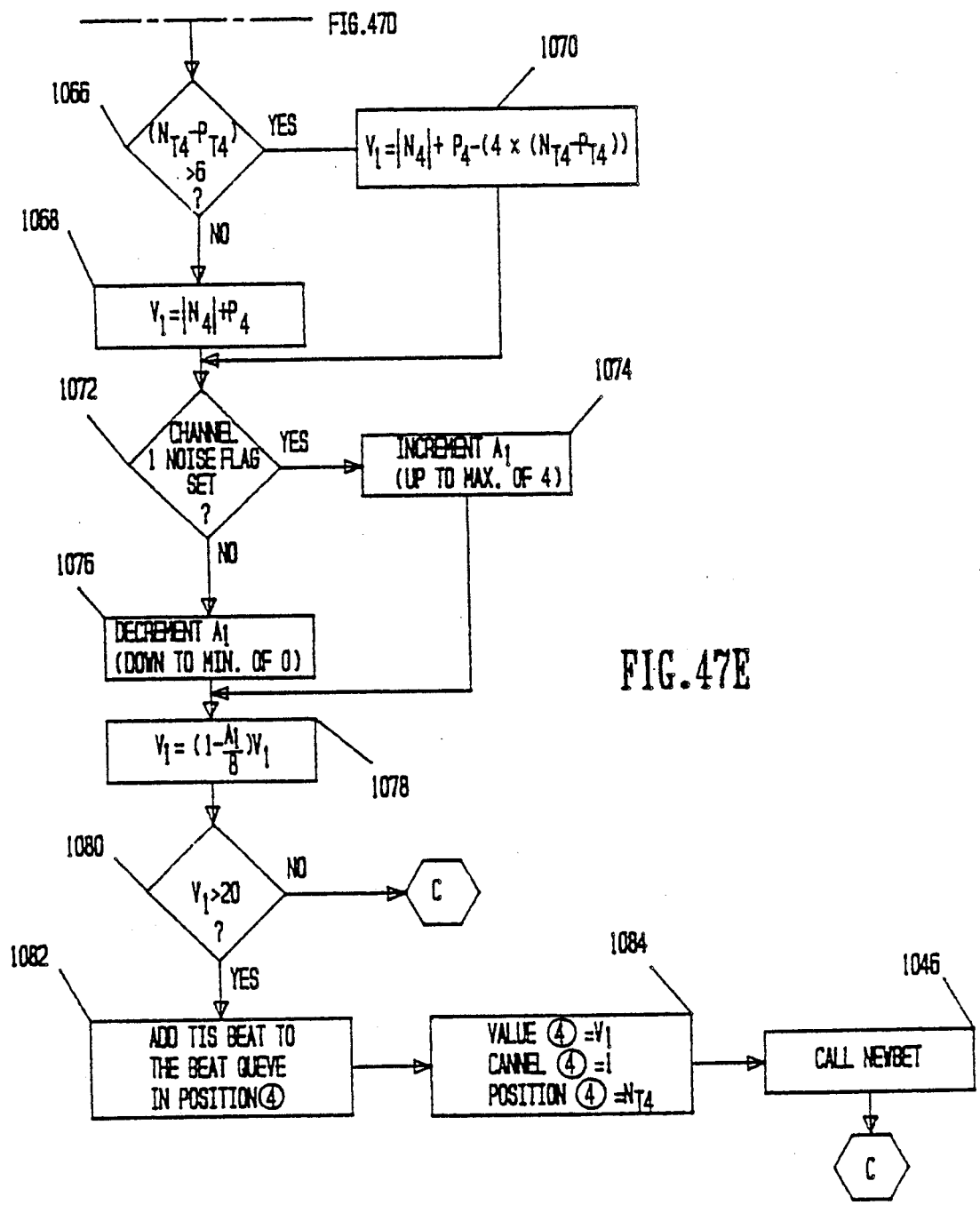
FIG. 47E is a fifth portion of a flow diagram of the DETECT module of the digital signal processing chip software.

The portions of the programs whose flow charts are shown in FIGS. 47B-C and 47D-E are analogous. The portion shown in FIG. 47B is reached if the previous value of $D_1$ was as sufficiently positive (i.e., greater than 12) to warrant further study, while control of the program passes to decision block 406 in FIG. 47D if the previous value of $D_1$ was sufficiently negative to be of interest.

Passing to decision block 1004 of FIG. 47B, a test of the current value of $D_1$ is performed. If the value of $D_1$ exceeds 120, it is recomputed 1008. The effect of the computations is to replace the current value of $D_1$ with a new value of $D_1$ which decreases linearly by the amount which the current value of $D_1$ exceeds 120. When the current value of $D_1$ is equal to 120, it is replaced by a value of $D_1$ of 80. When the current value of $D_1$ is 280, it is replaced by a value of $D_1$ of 0. After the computations 1008, program control passes to step 1010.

If, on the other hand, $D_1$ does not exceed 120, the program passes to decision block 1012, where the current value of $D_1$ is compared to 80. If it exceeds 80, it is replaced by a value of 80 (1014). Regardless of the result of the test in decision block 1012, program control then passes to 410, where the value of the most recent positive four-point derivative peak ($P_4$) is replaced by the current value of $D_1$. Then, the time of occurrence of $P_4$ is updated to the time of the latest sample 1016.

Thereafter, the value of the highest channel 1 raw data values since $P_4$ is set equal to the greatest of the last four channel 1 four-point derivative values 1018. Further, the time of the occurrence of $P_1$ is updated 1020.

Next, the program logic tests to determine whether the last four-point derivative peak was positive (decision block 1022) or whether the difference between the time of occurrence of the most recent positive four-point derivative peak exceeds the time of occurrence of the most recent negative four-point derivative trough by more than 20 samples (1024). If either of these conditions holds, program control returns to the subroutine call to subroutine GETDAT (903, shown in FIG. 47A). Otherwise, the program progresses to the decision block 1026, shown in FIG. 47C.

In decision block 1026, the times of occurrence of the most positive and most negative recent four-point derivative peak and trough are compared. If they do not exceed six sample intervals, the channel 1 beat value is updated to be equal to the sum of the magnitudes of the most recent positive and negative four-point derivative peak and trough 1028. Otherwise, the channel 1 beat value is set equal to the value established in step 1028, less four times the time difference computed in decision block 1026 (1030).

In either case, control passes to the decision block 1032, which tests to see whether the channel 1 noise flag has been set. If it has, the channel 1 artifact step value ($A_1$) is incremented by one count (to a maximum value of 4) 1034, while if the channel 1 noise flag is not set, $A_1$ is decremented by one count (but not below 0) 1036.

The present channel 1 beat value is next replaced by the old value weighted by a factor which is a decreasing function of the value of the channel 1 artifact step value ($A_1$) 1038. If, despite this weighting operation, the channel 1 beat value still exceeds 20 (see decision block 1040), this beat is added to the end of the beat queue 1042. In addition, the value of the beat placed in the beat queue is equal to the channel 1 beat value ($V_1$), the channel number is equal to 1 (when sampling channel 1 data), and the position of the beat added to the beat queue is set equal to the time of the most recent positive four-point derivative peak ($P_{T1}$) 1044. After these values have been established in the beat queue, the program calls the subroutine NEWBET (subroutine call 1046). If, on the other hand, the modified value of $D_1$ does not exceed 20, program control passes to the subroutine call to GETDAT (903, shown in FIG. 47A).

If program control had transferred to decision block 1006 (see FIG. 47D) rather than decision bock 1004 (in FIG. 47b), steps and decision blocks 1048–1084, corresponding to respective steps and decision blocks 1008–1044, are performed. The fundamental distinction between these two sequences of steps is that while steps and decision blocks 1008–1044 are concerned with the values and times of the most recent positive four-point derivative peak, the steps in decision blocks 1048–1084 are concerned with the most recent negative four-point derivative trough. In either case, the sequence of steps in decision blocks ends either with a return to the GETDAT subroutine in subroutine call 903 (on FIG. 47A) or with a subroutine call to subroutine NEWBET.

Subroutine NEWBET (see FIGS. 52A–B) merges the most recent beat placed in the beat queue with the next most recent beat placed in the beat queue, if the two beats are close beats detected in different channels (i.e., corresponding beats). The subroutine NEWBET will, if required, call the subroutine SNDBET to send the third most recent beat to be added to the beat queue to the log or else eliminate either the second or third most recent beat from the beat queue. In this latter case, the more recent beats in the queue are moved one position.

Upon entering the subroutine NEWBET, the decision block 1086 determines whether the most recent beat in the queue (beat 4) and next most recent beat in the queue (beat 3) came from different channels. If they did, control passes to the decision block 1088, where the number of samples separating the two beats is compared to eight. If the samples from the two channels occur with fewer than eight time samples between them, the two most recent beats added to the queue are merged into beat 3 (1090).

Then, the value of the most recent added beat is compared to the value of the next most recent added beat 1092. If the value of the most recent beat added to the queue exceeds that of the next most recent beat added to the queue, the position of the next most recent beat added to the queue (beat 3) is set equal to the position of the most recent beat added to the queue (beat 4) 1094.

Regardless of the outcome of the test in the decision block 1092, the program next recomputes the value of the next most recent beat added to the queue in step 1096. This value is replaced by the sum of the values of the two most recent beats added to the queue plus the value of the lesser of these two values minus the lesser of the values of the two most recently added beats, weighted by one-fourth of their sample separation. In accordance with the formula found in 1096 in FIG. 52A, it can be seen that the greater the value of the point separation between the two most recently added beats, the less the new value given to the next most recent beat added to the beat queue.

Figure 53C:
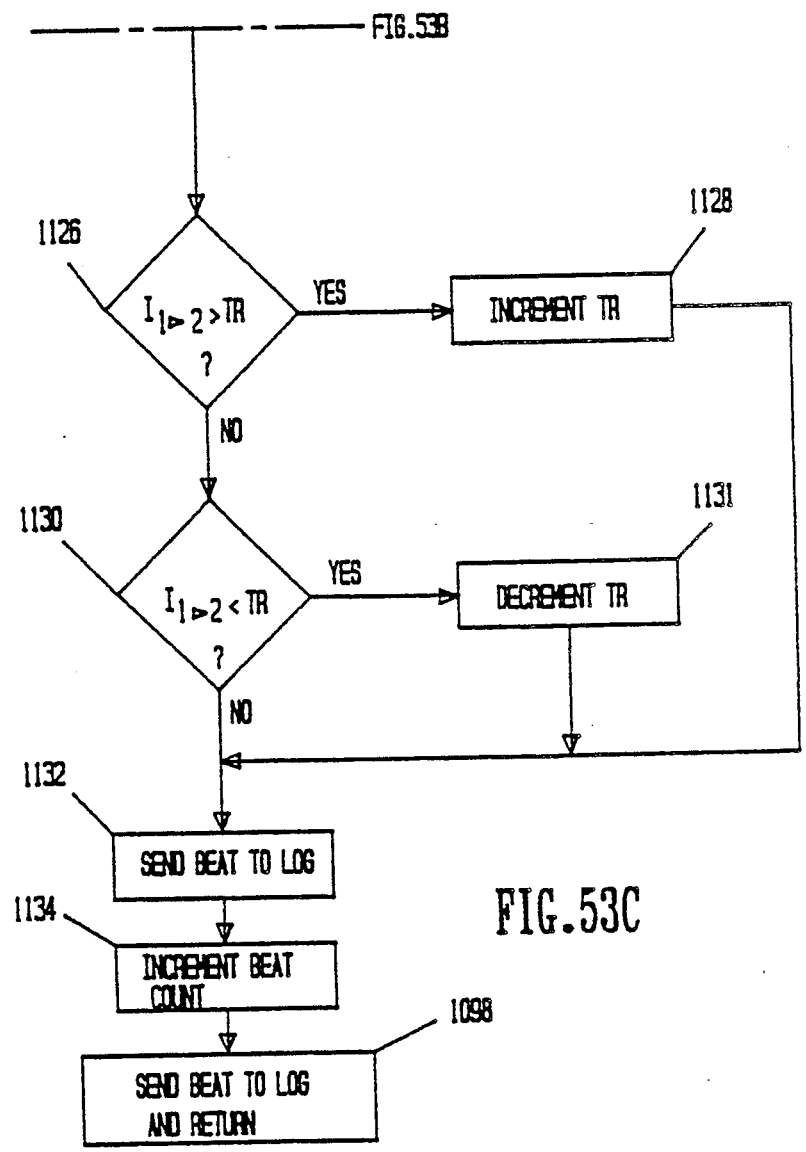
FIG. 53C is a third portion of a flow diagram of the SNDBET subroutine of the digital signal processing chip software.

Program control then passes to the decision block 1097, where the time interval between the beat to be considered to be sent to the log (beat 2) and the next most recent beat added to the beat log (beat 3) is compared to 230 milliseconds. If the time interval exceeds 230 milliseconds, the program passes to the subroutine call 1098 to subroutine SNDBET (in FIGS. 53A–B).

The value of the time interval between the occurrence of beats 1 and 3 is compared to that of the tracked interval (TR). The tracked interval is a slowly changing number that approximates the present average interval between beats. If the time interval between beats 1 and 3 is approximately equal to TR (e.g., within one-eighth of TR's value), the program passes to the decision block 1102. In the decision block 1102, the value of the next most recent beat to be added to the beat queue ($V_3$) is compared to twice the value of the beat to be considered to be sent to the log ($V_2$). If $V_3$ exceeds twice $V_2$, the program control passes to the step 1104, where $V_2$ is reduced by a factor of two. Regardless of the outcome of decision block 1102, program control passes to the decision block 1106.

If, instead, program control passes from the decision block 1100 to the decision bock 1108, the value of the interval between the sample time of the last beat sent to the log and the next most recent beat added to the beat queue is compared to approximately twice the tracked interval. If they are approximately equal, the value of the beat to be considered to be sent to the log ($V_2$) is doubled (1109).

Regardless of the outcome of the decision block 1108, the program control now passes to the decision block 1106, where the value of the beats to be considered to be sent to the log is compared to 35. If the value of the beat to be considered to be added to the beat log is less than 35, the beat is rejected as having a value that is too low and program control is passed to the subroutine call 1098 in FIG. 52A. On the other hand, if the beat is not rejected as having a value that is too low in the decision block 1106, the program continues to the decision block 1110 in FIG. 53B.

In the decision block 1110, the length of the interval between the time of occurrence of the last beat to be sent to the beat log (beat 1) and the beat to be considered to be sent to the beat log (beat 2) is compared to 310 milliseconds. If this interval is less than 310 milliseconds, the program control passes to the decision block 112, where the direction of the last beat to be sent to the log is compared to the direction of the beat to be considered to be sent to the log. If they are the same, the program control passes to the decision block 1114, while if they are not, the program passes to the decision block 1116.

In the decision block 1114, the value of the beat that is being considered to be added to the beat log ($V_2$) is compared to one-fourth of the value of the beat last sent to the beat log ($V_1$). If the value of the beat to be considered does not exceed one-fourth of the value of the beat last sent to the beat log, the program is returned to the subroutine call 1098 (in FIG. 52A), the beat having been rejected as a T-wave Similarly, if, in the decision block 1116, $V_2$ is less than one-half of $V_1$, the program control is returned to subroutine call 1098, the beat having been rejected as a T-wave.

In case the beat to be considered to be added to the beat log has not been rejected as a T-wave, program control passes to the decision block 1118, where the value of the interval between the time of occurrence of beat 1 is compared to the time of occurrence of beat 2. If this value is less than 390 milliseconds, a beat direction test, similar to that performed in the decision block 1112, is performed in the decision block 1120. Depending upon whether beats 1 and 2 are in the same direction, the value of beat 2 is compared to either one-eighth or one-fourth of $V_1$ (decision blocks 1122 and 1124, respectively). If $V_2$ does not pass either of these tests, program control is returned to the subroutine call 1098. Otherwise, the program control passes to the tracked interval comparison test, shown in FIG. 53C.

If the beat is not rejected as a T-wave by the decision made by decision block 1124, the program continues to decision block 1126. The purpose of the next section of the subroutine SNDBET, after it has been determined that beat 2 is to be placed in the beat log, is to change the value of the tracked interval (TR). If, in decision block 1126, it is determined that the tracked interval is shorter than the interval between points 1 and 2, the tracked interval is incremented by one 1128. If the tracked interval is not less than the interval between beats 1 and 2, the program next tests whether the tracked interval is greater than the interval between beats 1 and 2 (1130). If it is, the tracked interval is decremented by 1.

Regardless of the decisions made in decision blocks 1126 and 1130, the program causes the data for the current beat to be sent to the beat time log 1132. After this, the beat count is incremented 1134 and program control returns to the subroutine call 1098 (in FIG. 52A).

Decision 1136 determines whether beat 2 was sent to the log and updates the beat queue accordingly. If beat 2 was sent to the log, the beats in positions 2, 3 and 4 are moved to positions 1, 2 and 3 in the beat queue 1138 and the program returns to the subroutine call 1046 (see FIGS. 47C and 47E) and, from there, to the GETDAT subroutine call (step 903 in FIG. 47A). If, on the other hand, beat 2 was not sent to the beat log, it is eliminated from the beat queue and beats 3 and 4 are moved to positions 2 and 3, respectively 1140. Thereafter, program control returns to the call to subroutine NEWBET 1046, and from there to the GETDAT subroutine call 903 (in FIG. 57A).

The call to the subroutine SNDBET (1098, in FIG. 52A) resulted from the decision that the time interval between beats 2 and 3 is greater than 230 milliseconds. If the interval between beats 2 and 3 in the beat queue is less than or equal to 230 milliseconds, these beats may result from fast ventricular tachycardia. Decision block 1142 therefore captures, for further consideration, all beats 2 whose interval to the next beat in the beat queue is between 170 milliseconds and 230 milliseconds.

Figure 52A:
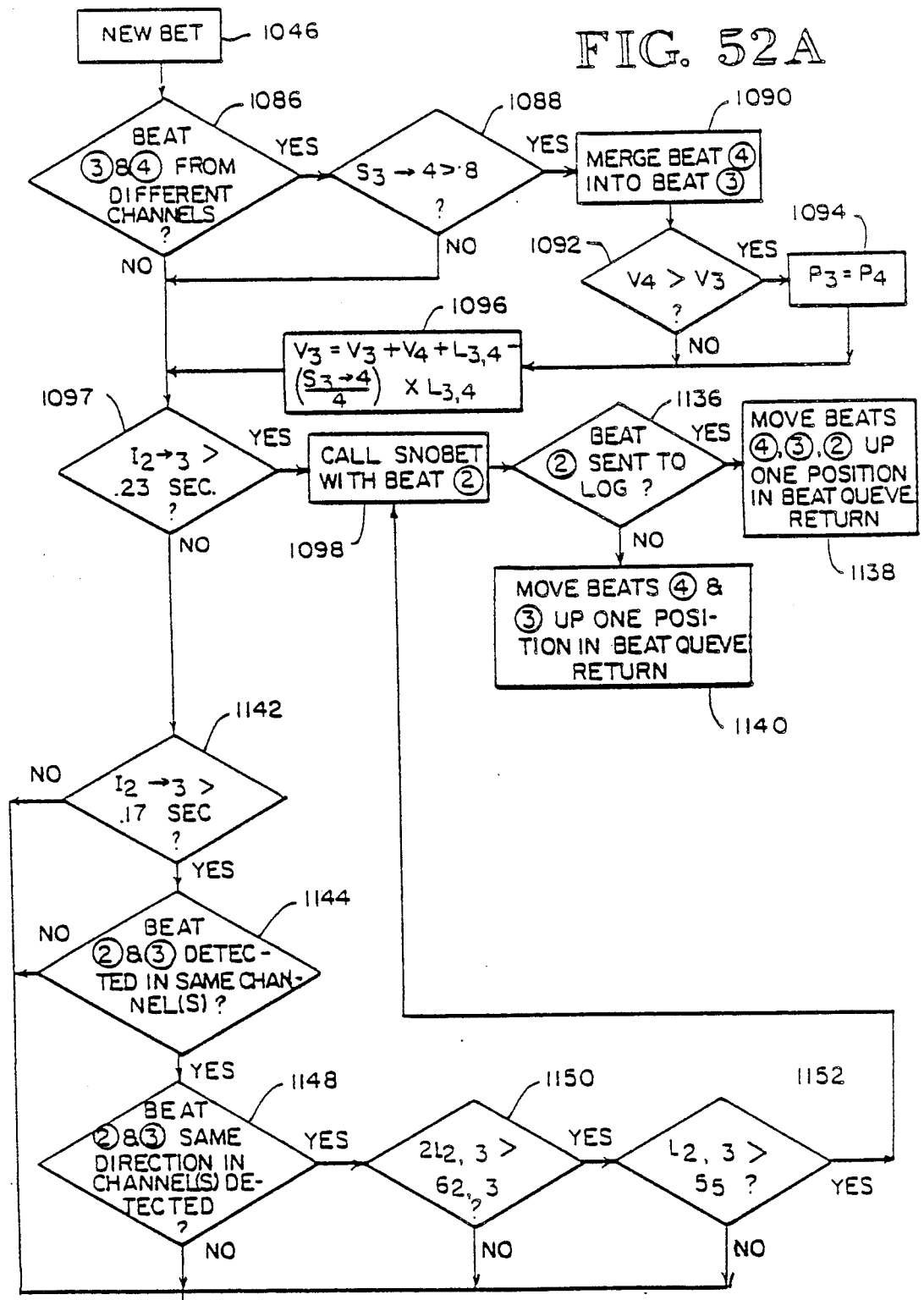
FIG. 52A is a first portion of a flow diagram of the NEWBET subroutine of the digital signal processing chip software.
Figure 52B:
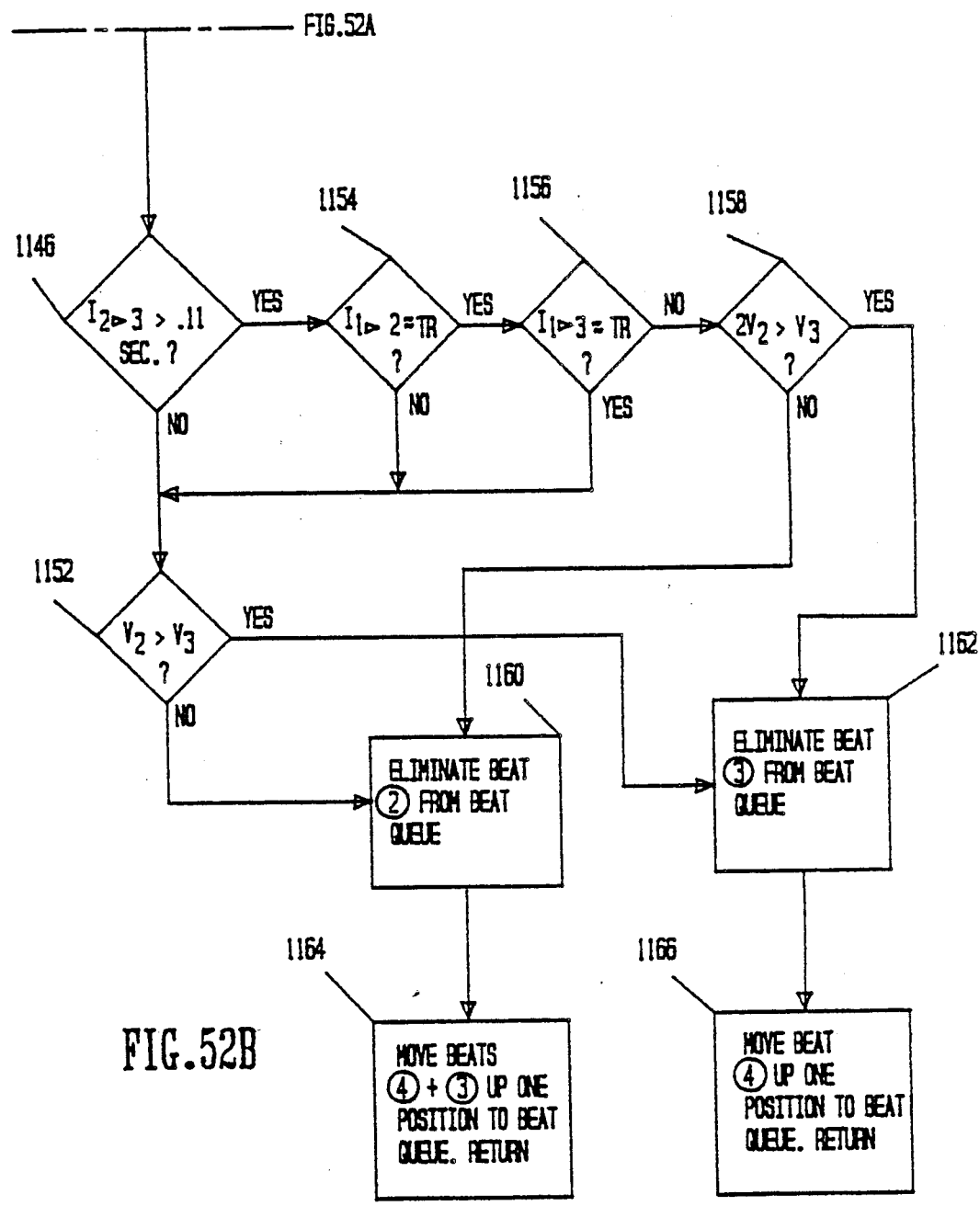
FIG. 52B is a second portion of a flow diagram of the NEWBET subroutine of the digital signal processing chip software.

If this is the case, the program determines whether beats 2 and 3 were detected in the same channels (1144). If they were not, control passes to decision block 1146 (FIG. 52A). If they were, the program checks to determine whether beat 2 has the same direction as beat 3, in the channels detected 1148. If it does, twice the lesser of the values of beat 2 and beat 3 is compared to the greater of the values of beat 2 and beat 3 (1150).

If twice the lesser of $V_2$ and $V_3$ is greater than the greater of $V_2$ and $V_3$, the program proceeds to the decision block 1152. Otherwise, the program proceeds to the decision block 1146. In the decision block 152, the lesser of $V_2$ and $V_3$ is compared to 55. If the lesser of $V_2$ and $V_3$ is greater than 55, the program passes to the subroutine call to the subroutine SNDBET (call 1098). If the lesser of $V_2$ and $V_3$ is less than or equal to 55, program control passes to the decision block 1146 (in FIG. 52B).

In decision block 1146, the time interval between beat 2 and beat 3 is compared to 110 milliseconds. This section of the program is to eliminate either beat 2 or beat 3 from the beat queue. Accordingly, if the time interval between beat two and beat 3 is less than or equal to 110 milliseconds, the beat with the larger value is retained. This is accomplished in the decision block 1152

If the time interval between beat 2 and beat 3 exceeds 110 milliseconds, the program proceeds to the decision block 1154, where the time interval between beat 3 and beat 2 is approximately equal to the tracked interval (TR). For example, the decision block 1154 can decide whether the interval between the beat 1 and beat 2 is between $\frac{3}{4}$ and $1\frac{1}{4}$ times TR. If it is, then the program proceeds to the decision 1156. Otherwise, the program returns to the decision block 1152.

In the decision block 1156, the time interval between beat 1 and beat 3 is compared to the tracked interval. If these intervals are approximately equal (e.g., if the time interval between the occurrence of the first beat and the occurrence of the third beat falls between $\frac{3}{4}$ and $1\frac{1}{4}$ times the tracked interval), the program passes to the decision block 1152. If, on the other hand, the time interval between the occurrences of the beat 1 and the beat 3 is not approximately equal to the tracked interval, the program, in the decision block 1158, compares twice the value of beat 2 to the value of beat 3 ($V_3$). If twice $V_2$ does not exceed $V_3$, beat 2 is eliminated from the beat queue 1160. Otherwise, the beat 3 is eliminated from the beat queue 1162.

Similarly, if, in decision block 552, $V_2$ exceeds $V_3$, beat 3 is eliminated from the beat queue 1162. Otherwise, the program proceeds from the decision block 1152 to the step 1160, where beat 2 is eliminated from the beat queue.

After eliminating beat 2 from the beat queue 1160, the program moves beats 3 and 4 to positions 2 and 3 in the beat queue 1164, to replace beat 2, which was eliminated. Then the program returns to the subroutine call to the subroutine NEWBET (call 1046), and to the subroutine call to the subroutine GETDAT (903, in FIG. 47A). If beat 3 is eliminated from the beat queue 1162, the program moves beat 4 into the position occupied by beat 3 in the beat queue and returns to the new beat subroutine call 1046 (1166).

2. Binning Module

Figure 54B:
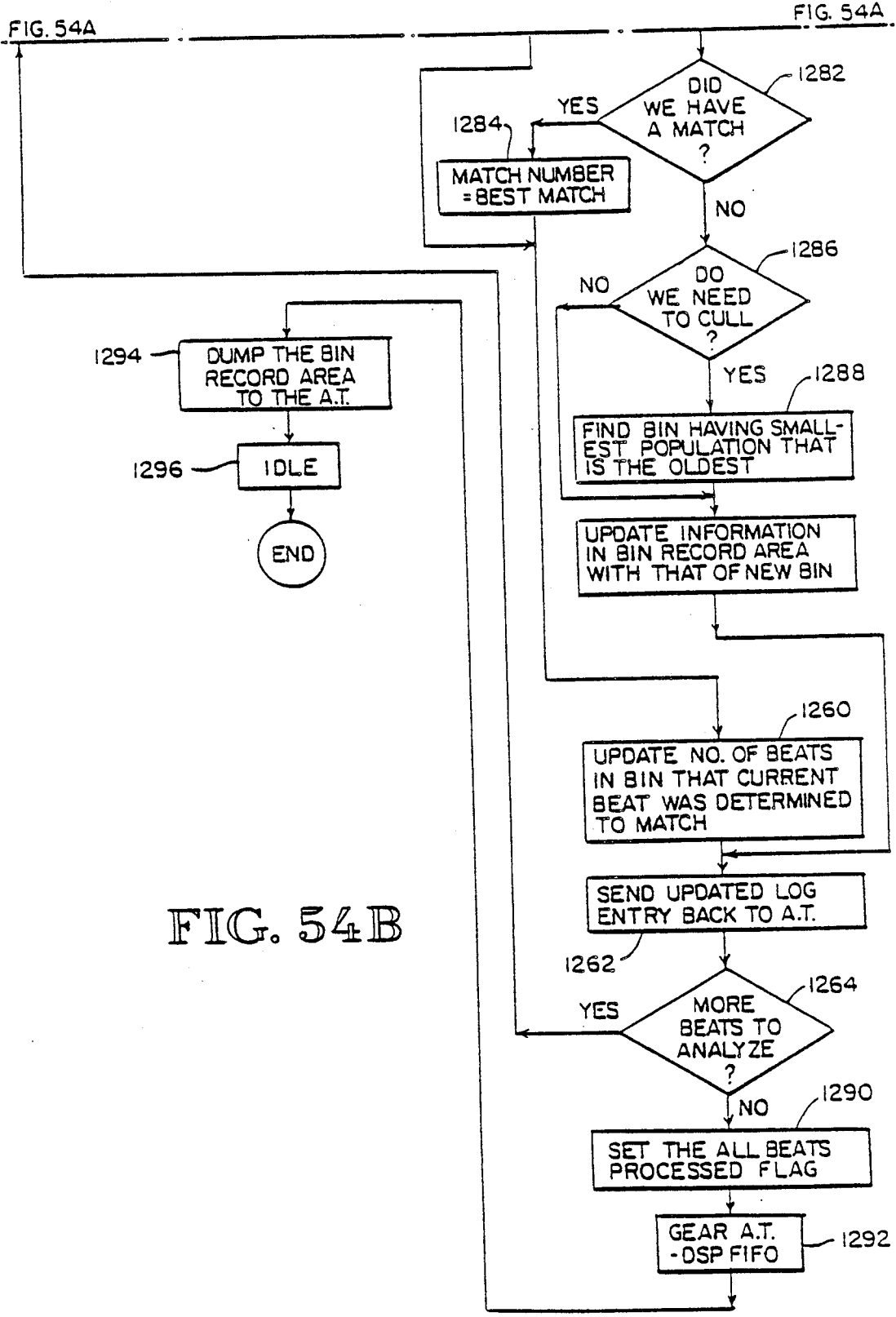
FIG. 54B is a second portion of a flow diagram of the binning module of the digital signal processing chip software.

Turning to the flow chart describing the binning operation performed by the digital signal processing board (FIGS. 54A-B), it will be appreciated that the binning operations described therein are performed upon the data that has been stored on the hard disk 73 of the main processor subsystem 62. The binning operation is performed, on the second pass through the ECG data, as a function of a sensitivity factor that can be designated by the user to have any one of five values. Executable listings of the programs that can be run by the DSP chip are respectively provided in Appendices III-VII for each of the sensivity factor values.

The main processor subsystem 62 passes data from the hard disk 73 to the DSP board 64, as required. On the DSP board, the beat data is analyzed and binned according to similarities in morphology, in a manner to be described subsequently. The result of the binning operation is that every beat in the beat time log is assigned a bin number, thereby categorizing it with other similar beats. During the time that the DSP board 64 is performing the binning operation, the main processor subsystem 62 is both transferring data to and from the DSP board 64 and obtaining patient information from the user through the keyboard 68 and the display screen 66.

In the first step of the program 1200 (see FIG. 54A), interrupt vectors are set up within the DSP board 64 in order to allow the main processor subsystem 62 to communicate with the DSP board 64. Next, the DSP board 64 clears its internal RAM 1202, clears any pending interrupt 2 (1204), and clears the AT-to-DSP first-in, first-out (FIFO) buffers 320a–b (1206). Subsequently, the bin record area of the main processor subsystem 62 is cleared 1208 and then seeded with bin numbers 1210. The Fast Fourier Transform (FFT) program is transferred to the on-chip RAM 1212. The program then passes from the program RAM 308 to the on-chip RAM built into the DSP chip 300.

After the FFT program has been successfully loaded into the DSP chip 300, it signals the main processor subsystem 62 to put data into the low six kilobyte and high six kilobyte buffer sections of the data RAM 310 (1214). The number of parts is zeroed 1216.

The program enters a large iterative loop after saving the first pass total beat information in the internal RAM of the DSP chip 1218.

One pass is made through the loop for each set of data referred to in the beat time log.

Figure 55:
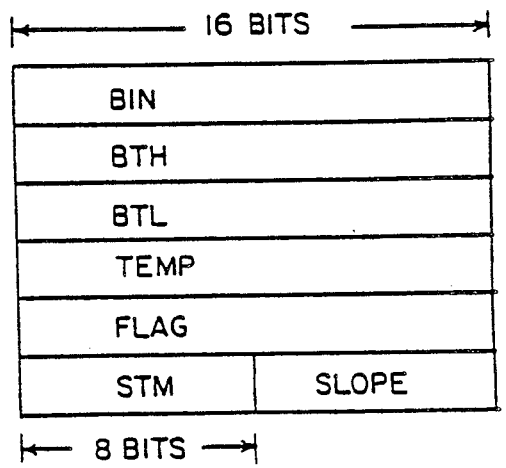
FIG. 55 is a schematic representation of the structure of an entry in the beat time log.

The first step in this portion of the program reads the six items contained in the beat time log (BTL) for a particular beat 1220 (see FIG. 55). The data in the BTL is 16 bits wide. It includes the bin number (to be assigned by the binning operation (BIN#)), a 32-bit number indicating the time of occurrence of the beat in terms of 1/120 second samples of time (BTH and BTL), a TEMP location for temporary storage of data, a FLAG word, an 8-bit ST measurement, and an 8-bit ST-slope measurement. The FLAG word contains 1-bit flags indicating (1) presence of an event marker, (2) occurrence of a beat an unexpectedly long time after the preceding beat, (3) occurrence of a premature beat, (4) presence of a calibration pulse, (5) detection of channel 1, (6) detection of channel 2, (7) presence of noise on channel 1, (8) presence of noise on channel 2, (9) a previously noisy channel 1, and (10) a previously noisy channel 2. The beat time, FLAG, and ST-related variables are set during the operation of the DETECT module.

Next, the data corresponding to the current beat is located in the appropriate 6 k buffer portion of data RAM 310 (1222, in FIG. 54A). Once found, the data of the present beat is transferred to a linear buffer 1224. The data representing the current beat consists of both channel 1 data and channel 2 data, regardless of whether either of the two channels has been determined to contain noise. The data representing one channel of the present beat consists of thirty-two samples The tenth sample corresponds to the location of the R-wave, as determined by the beat detection software. Nine samples preceding the location of the R-wave and twenty-two samples immediately following the location of the R-wave constitute the remainder of the samples.

The thirty-two samples of channel 1 data are loaded into a location on the DSP chip 300, as shown in FIG. 54A (1226). Then, the DSP chip 300 performs the Fast Fourier Transform (FFT) on the thirty-two samples of the channel 1 data, producing sixteen pairs of real and imaginary data. Each pair of data corresponds to a different frequency. The sixteen samples are uniformly spaced at frequencies between 0 and 60 Hz (i.e., one-half of the per/channel sampling rate). Therefore, the first pair of real and imaginary data (or, equivalently, magnitude and phase data) represent components at 3.75 Hz, the next pair represent data at 7.5 Hz, and so forth. The result of performing the FFT in step 1228 is moved to a result holding buffer on the DSP chip 300 (step 1230).

Next, the thirty-two samples of the channel 2 data for the current beat are loaded into the appropriate location in the DSP 300 (1232). The FFT is performed on the channel 2 samples 1234 and also moved to the result holding buffer 1235.

The next sequence of steps in the binning operation associates transformed samples of the current beat with a bin. In one embodiment, these steps involve the six pairs of real and imaginary components of data from channels 1 and 2 that represent the lowest six frequencies. These frequencies are 3.75, 7.5, 11.25, 15.0, 18.75 and 22.5 Hz. Accordingly, then, these steps concern twelve pairs of numbers, six pairs for each channel of data. These number pairs are processed one at a time.

Figure 56:
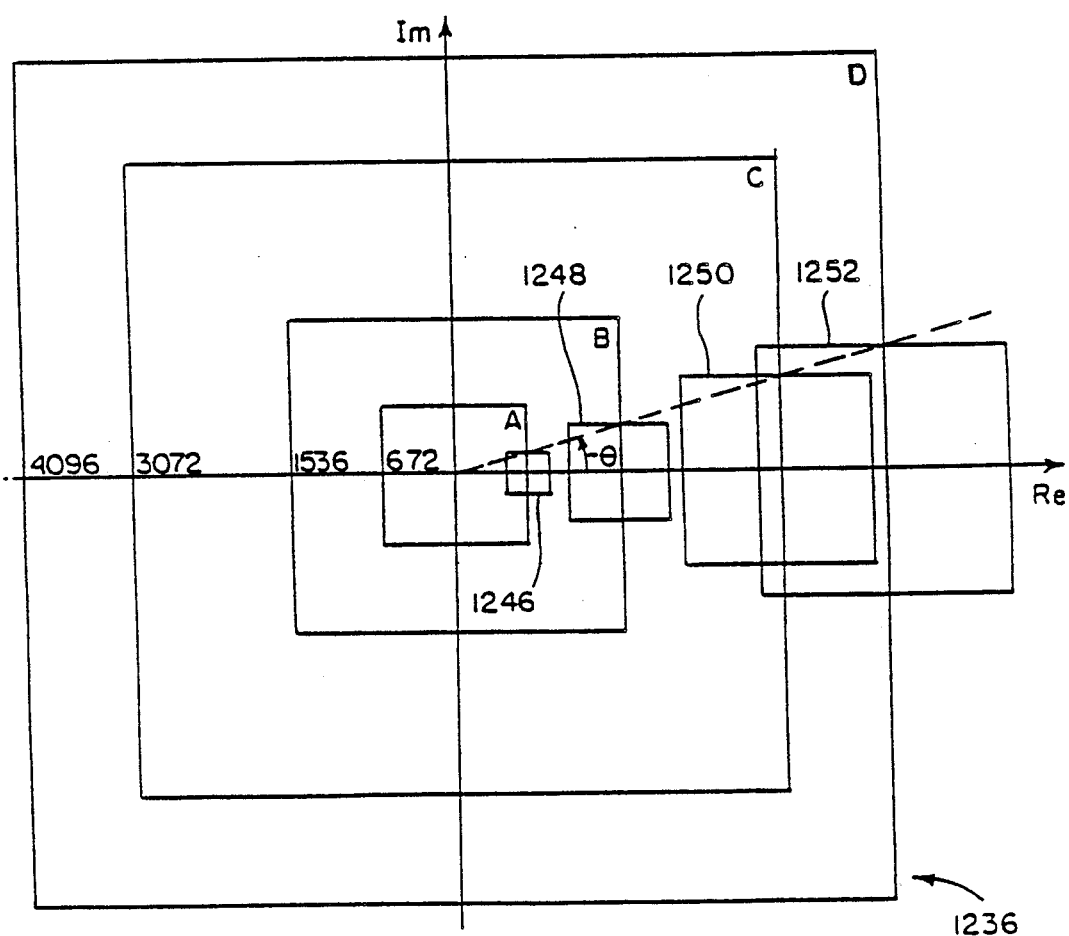
FIG. 56 is a schematic drawing illustrating principles of the binning operation.

Each number in a frequency coordinate pair has a value between plus and minus ($\pm$) 4,096. Therefore, as shown in FIG. 56, each data pair can be mapped into a point in the complex plane 1236. The twelve pairs of numbers corresponding to the first beat define a first bin. The pattern describing the members of this first bin are the twelve points in the complex plane 1236, with each point being associated with either channel 1 or channel 2 and with one of the six frequencies.

The six pairs of numbers that describe the pattern for the second and following beats are compared, according to their channel and frequency, with the groups of points that defines the bins already in existence. If the twelve points characterizing the morphology of a beat whose bin is being determined are sufficiently close, on a point-by-point basis, to the twelve points of an already existing bin, that beat may be associated with that bin. If the twelve points describing the morphology of a present beat do not come sufficiently close to all twelve points describing all already-existing bin, a new bin is defined. The twelve points defining the new bin are the twelve points characterizing the morphology of the most recent beat.

The twelve points describing a beat need not match precisely with the twelve beats defining a bin for the beat to possibly be placed in the bin. The twelve points describing the morphology of the beat are sufficiently close to the twelve points defining the bin if each of the twelve points falls within windows centered on the points defining the bin. The size of a window placed around a point depends upon the location of the point in the complex plane 1236. It also depends upon the value of a sensitivity factor.

A clearer understanding of the relationship between the size of a window, the location of a point, and the sensitivity factor can be gained with reference to FIG. 56. As shown, the complex plane 1236 is divided into zones 1238 through 1244. Zone A, indicated by reference numeral 1238, is a square centered about the origin of the complex plane 1236 and extending between complex coordinates having values between −672 and +672. Zone B, indicated by reference numeral 1240, has a square boundary and is symmetrically placed about zone A, 1238. The outer boundary of zone B, 1240, has complex components between −1536 and +1536. The inner boundary of zone B coincides with the outer boundary of zone A.

Zone C designated by reference numeral 1242, surrounds zone B. Its outer perimeter is defined by complex values between −3072 and +3072. Its inner boundary coincides with the outer boundary of zone B. Zone D, reference numeral 1244, is the remainder of the complex plane whose coordinates lie between −4096 and +4096.

The size of a window placed around a point defining one component of a bin depends upon the zone into which that point falls, as well as the value of the sensitivity factor. Sensitivity factor is related to the wedge angle, $\theta$, shown in FIG. 56, as indicated in the table below:

TABLE D

| Sensitivity Factor | (degrees) |
|---|---|
| Sensitivity 1 | 25 degrees |
| Sensitivity 2 | 22 degrees |
| Sensitivity 3 | 18.5 degrees |
| Sensitivity 4 | 15 degrees |
| Sensitivity 5 | 12.5 degrees |

For a given sensitivity factor, the size of the window to be applied for points falling within a zone is defined to be a square whose edges are equal to the length of the edge of the particular zone that is captured by a double wedge having the angle given in the table above. For example, if the sensitivity factor is 4, the windows placed around all bin-characterizing points falling within zone B are 822 ($=2\times 1536\times\tan(15°)$) units on a side. For a sensitivity factor of 4, zones A through D (reference numerals 1238–1244) are associated respectively with windows 1246–1252, whose edges are respectively 360, 822, 1646 and 2194 units long.

If a particular beat is eligible for membership in more than one bin, the sum of the magnitudes of the difference vectors between the points describing the beat and the points defining the bin is used to determine the bin with which the beat will be associated. The beat will be associated with the bin having the smallest sum of magnitudes of difference vectors from the points describing the beat.

Only a predetermined number (for example, 1650) of bins are allowed If, in defining the bins, that number is exceeded, the bin having the smallest number of associated beats is redefined to be associated with the current beat. Those beats associated with the bin before the bin was redefined are associated with a special "garbage pail" bin. If more than one bin has the fewest number of members, that bin having the earliest-occurring beat as a member is redefined.

Each bin (except the garbage pail bin) is represented by a model waveform which is determined by averaging the beats belonging to that bin (up to the first sixteen beats). This model waveform is used for display purposes on the display screen 66.

Returning to FIG. 54A, the loop defined by the step 1254 and the decision block 1256 configures the variable window binning threshold array that defines the window sizes for each of the zones 1238 through 1244. When this task is complete, the program proceeds to decision block 1258, wherein it is determined whether there are any presently existing bin records. If there are not, the program proceeds to step 1260 (see FIG. 54B).

For the first beat in the record, step 1260 defines a bin having the same components as the first beat. As shown in 1262, the now-updated bin log entry is returned to the data RAM 310 of the main processor subsystem 62. At decision block 1264, the program determines whether there are further beats to analyze. If there are, the program calculates the components describing the next beat (1220). When the components describing any beat except the last beat have been calculated, the program initializes variables used in determining the best bin match 1266.

The program next associates the appropriate windows with the components resulting from transforming the current beat and with the components defining a potentially matching bin in the bin record array 1268. At decision block 1270, the program determines whether a particular frequency component of the current beat falls within the window placed about the point defining the corresponding frequency component of the bin. If it does, the best match variables are updated 1272, and decision block 1274 determines whether there are more frequency components to be considered. If there are, the program returns to decision block 1270. If not, the results of the best match variables are compared to the previous best match variables and updated if necessary 1276. If, at decision block 1270, any particular frequency component of the beat being considered falls outside the window centered about the point defining the corresponding frequency window for the bin under consideration, the current beat cannot be associated with that bin and, therefore, the pointers to the bin record array are indexed 1278.

In decision block 1280, the program determines whether there are further bins to be tested. If there are, the program returns to block 1268; otherwise, the program proceeds to decision block 1282 (see FIG. 54B). If, in decision block 1282, it is determined that a match between the current beat and a bin has been established, the match number is set equal to the best match in 1284, and the number of beats associated with the bin is updated 1260. If no match was determined by decision block 1282, the program proceeds to decision block 1286, where it is determined whether the number of bins defined equals the maximum possible number of bins. If it does, the program determines the bin having the smallest population that is the oldest 1288. The beats that were associated with that bin are associated with the garbage pail bin, and the program proceeds to step 1262.

If, in decision block 1264, there are no further beats to analyze, a "all beats processed" flag is set 1290 and a pathway is established between the DSP board 64 and the main processor subsystem 62 through the FIFOs 358 and 360 (1292). In one embodiment, the beats associated with the largest bin are labeled as "NORMAL" beats. The labels of this bin can be changed and other unlabeled bins can be given labels by the clinician/user or a computer program. In step 1294, the bin record area is passed to the main processor subsystem 62 for storage and then the program enters the idle state 1296.

3. Rasterization Module

Figure 57:
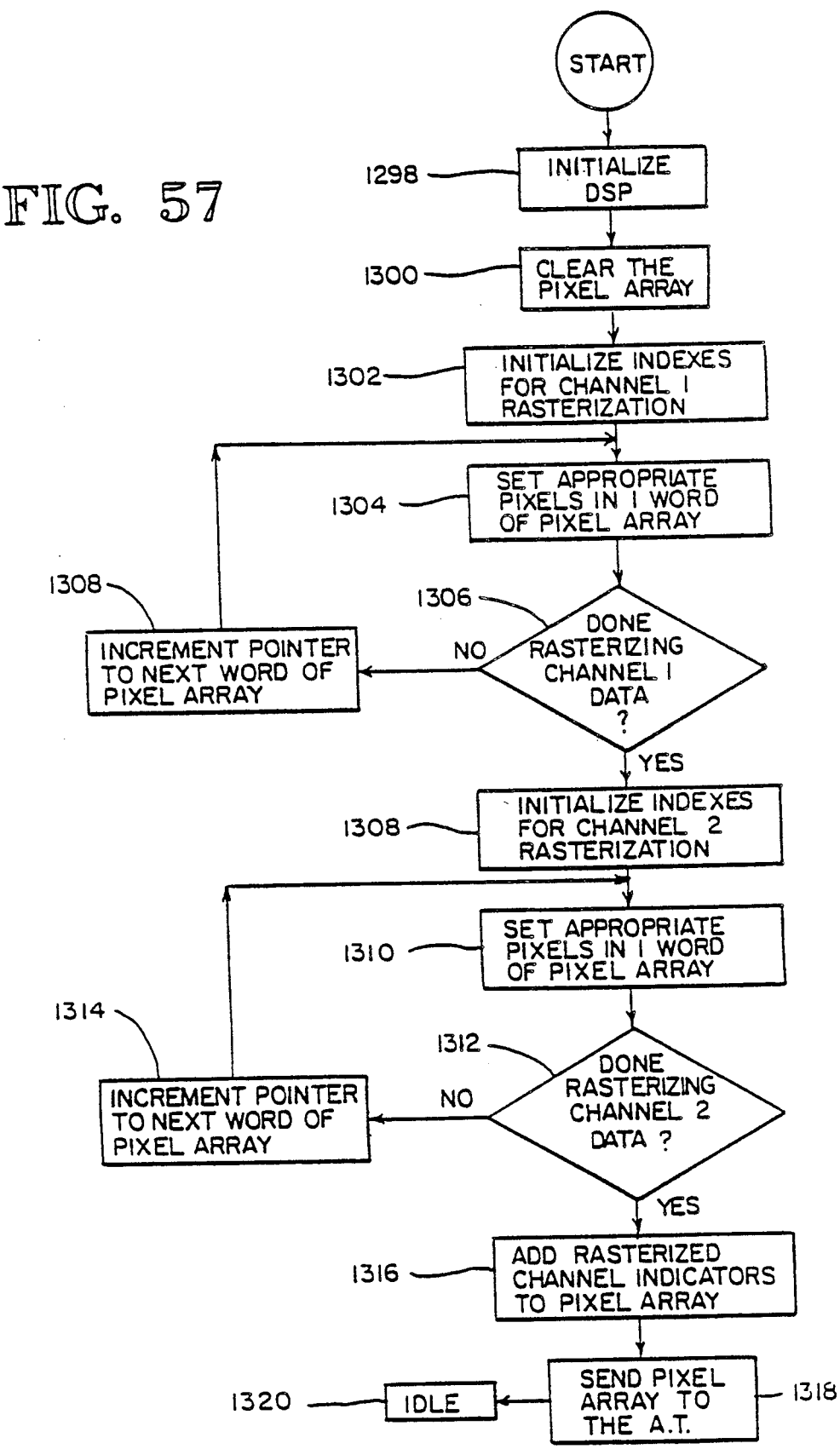
FIG. 57 is a flow diagram of the rasterization module of the digital signal processing chip software.

The DSP board 64 also performs a rasterization operation on the data that is to be printed by the laser printer 72. The flow chart for the program used by the DSP board in performing this operation is shown in FIG. 57. The clinician/user can decide to request a printout from the laser printer that contains either channels of ECG data or only one particular channel of ECG data. Appendix VIII provides an executable listing of a program used by the DSP board 64 if the clinician/user wishers to obtain a printout showing both channels of ECG data. Appendix IX is an executable listing of a program used by the DSP board when the clinician/user wishes a printout of only a single channel of ECG data.

Referring to FIG. 57, the DSP board is initialized 1298. Next, the pixel array that will contain the information to be printed by the laser printer is cleared 1300.

The next sequence of steps are concerned with rasterizing channel 1 information. In step 1302, indices needed for the channel 1 rasterization are initialized. In the loop defined by step 1304, decision block 1306, and step 1308, the pixels in the pixel array are set, one word at a time. After it has been determined by the decision block 1306 that al of the channel 1 data has been rasterized, the program proceeds to a series of steps for rasterizing the channel 2 data. Steps 1308, 1310 and 1314 and decision block 1312 are directly analogous to steps 1302, 1304 and 1308 and decision bock 1306. After both channels of data have been rasterized, indicators of the rasterized channels are added to the pixel array 1316. The program then sends the pixel array to the main processor subsystem 62 (1318) and then enters an idle state 1320.

4. Superimposition Module

Figure 58:
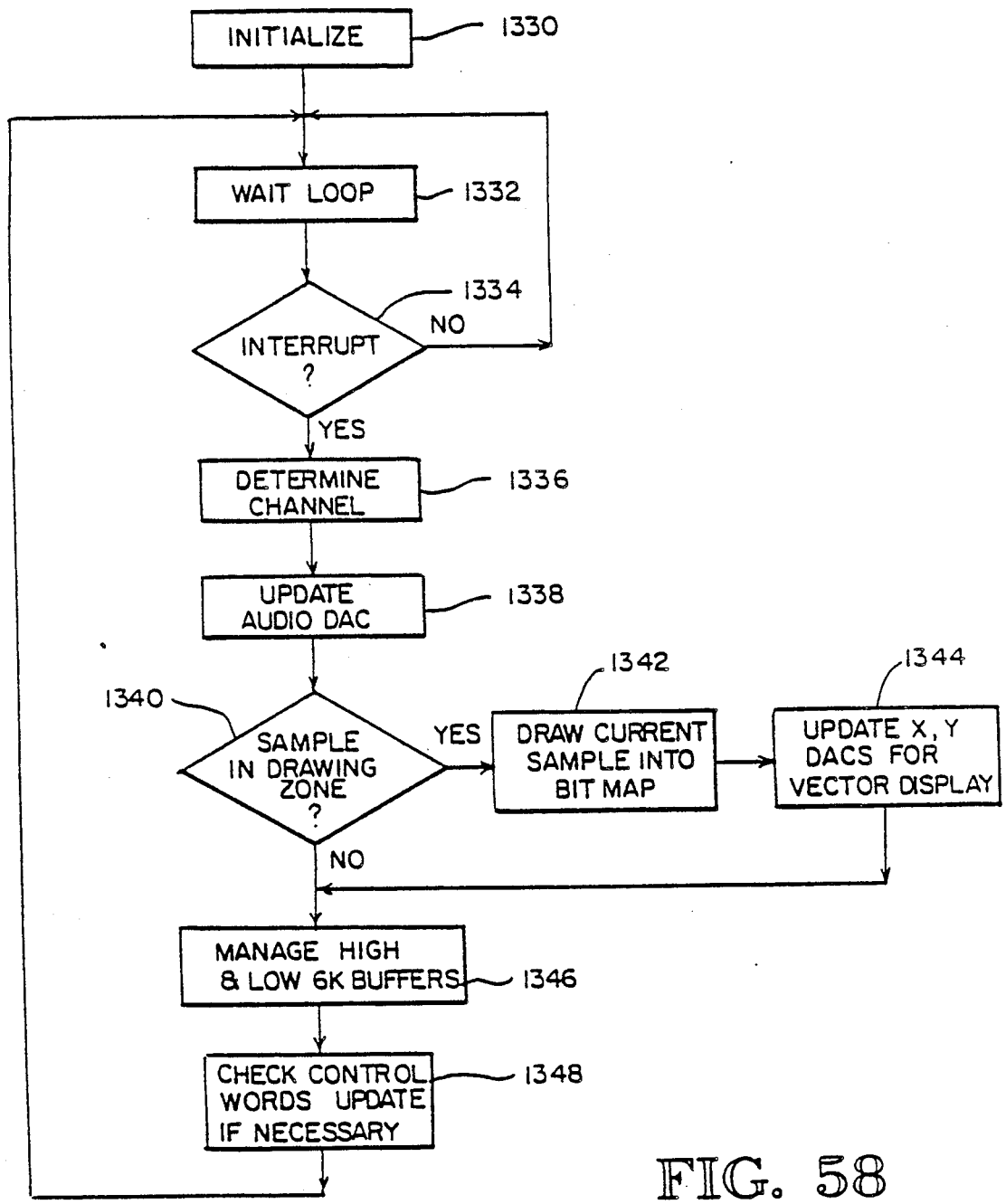
FIG. 58 is a flow diagram of the superimposition module of the digital signal processing chip software.

The DSP board 64 can also be used to provide the main processor subsystem 62 with properly located representations of the sequence of detected beats. These representations are produced at high speed (for example, ten times real time) for display on the display device 66, by the Superimposition module. Reproductions of the sounds of the detected beats is presented simultaneously with the display. An executable listing of a program which accomplishes this task is provided in Appendix X, and a flow chart is shown in FIG. 58.

After initializing appropriate counters 1330, the program enters a wait loop 1332, in which it remains until an interrupt is received 1334. The interrupt is produced by the main processor subsystem 62 when it has retrieved the next sequential sample of the ECG data. The sample comes from the high and low Gk buffers of the data ROM 310, which are supplied from the hard disk 73. The program next determines the channel which has been requested by the clinician/user for display on the display screen 66 (1336) and updates the audio D/A converter 418 with the sample for the proper channel 1338.

Although the audio D/A converter 418 uses all of the sequential data for the channel closed by the clinician/user, only portions of the data are displayed on the display screen 66. The displayed samples occur within predetermined sample zones placed around the location of the R wave selected for each of the beats detected by the DETECT module. Therefore, the program determines whether the current sample lies within a drawing zone 1340. If it does, the current sample is drawn into the bit map being generated 1342 and the X and Y D/A converters 404 and 406 are updated for vector display 1344. The samples are drawn and displayed with their R waves coincident. If a beat to be drawn is placed in a bin that is not classified as "normal" it can be drawn in a differing color and its display slightly prolonged to emphasize its occurrence to the user. If desired, the waveforms can be displayed in the reverse order from their occurrence.

The program next manages the data contained within the high and low Gk buffers 1346 and checks and updates the words that control display factors and audio factors 1348. If desired, audio signals can be produced for both channels and their volumes can be controlled separately.

One skilled in the art could make many modifications and alterations to the embodiments described above without departing from the spirit and scope of the invention. The spirit and scope of the invention are to be limited only by the following claims.

I claim:

1. A method of analyzing data representing a patient's heart beats over a period of time as a plurality of waveforms, the method comprising the steps of:
   (a) performing a Fourier analysis on the beat data to obtain pluralities of points in the complex plane representing the natural complex frequencies of each beat and preliminarily categorizing the beats into a plurality of bins of similar waveforms based on the proximity of corresponding pluralities of points in the complex plane;
   (b) displaying a plurality of representative beats on a display screen, the beats being representative of a plurality of bins;
   (c) selecting a bin for possible recategorization;
   (d) after performing steps b and c, displaying the waveform of a representative beat from the selected bin superimposed over a waveform from a displayed bin to allow direct comparison of the waveform of the selected bin and the displayed bin;
   (e) comparing the superimposed waveforms to determine if they are similar enough to be merged; and
   (f) after comparing the superimposed waveforms, merging the selected bin and the displayed bin compared therewith if sufficient similarity is found.

2. The method of claim 1 including the additional step of analyzing the beats categorized within each bin to create a representative beat that is a composite of a plurality of beats within the bin.

3. A system for analyzing data representing a patient's heart beats over a period of time as a plurality of waveforms, the system comprising:
   means for performing a Fourier analysis on the beat data to obtain pluralities of points in the complex plane representing the natural complex frequencies of each beat and preliminarily categorizing the beats into a plurality of bins of similar waveforms based on the proximity of corresponding pluralities of points in the complex plane;
   means for displaying the waveform of a representative beat which is representative of a plurality of bins;
   means for selecting a bin for possible recategorization and displaying the waveform of a representative beat from the selected bin superimposed over a waveform from a displayed bin to allow direct comparison of the waveforms of the selected bin and the displayed bin;
   pointing means for designating whether the selected bin and the displayed bin should be merged; and
   means responsive to the pointing means for merging the selected bin and the displayed bin compared therewith.

4. The system of claim 3 wherein the waveforms for the representative beats of each bin comprise a composite waveform generated from the individual beats in the bin.

5. A method of analyzing data representing a patient's heart beat over a period of time as a plurality of waveforms, the method comprising the steps of:
(a) performing a discrete Fourier analysis on the beat data to obtain pluralities of points representing the natural complex frequencies of each beat and preliminarily categorizing the beats into a plurality of bins of similar waveforms based on the proximity of corresponding pluralities of points in the complex plane;
(b) displaying the waveform of a beat which is representative of a plurality of bins on a display screen;
(c) selecting as a current bin one of the bins for which a representative beat is being displayed;
(d) selecting a beat waveform within the current bin as a current beat; and
(e) simultaneously displaying a representative waveform for the displayed bins and the current waveform and a plurality of waveforms surrounding the current waveform in a strip format to enable review of the heat activity at the time of the current waveform.

6. A method of analyzing data representing a patient's heart beat over a period of time as a plurality of waveforms, the method comprising the steps of:
converting the waveforms to a plurality of points in the complex plane using a discrete Fourier transform;
comparing the corresponding Fourier transform-generated points in the complex plane to one another by determining whether one point in the complex plane falls within a window area of predetermined size which is centered about the other corresponding point in the complex plane; and
based on the results of the comparison, categorizing the beats corresponding to the coordinates into a plurality of bins of waveforms having similar characteristics.

7. A method for categorizing ECG data which contains a plurality of heartbeat waveforms, each waveform having a predetermined feature, the method comprising the steps of:
(a) sampling the data;
(b) detecting the occurrence of the predetermined feature in the sampled data and identifying each of the waveforms containing the predetermined feature;
(c) selecting each portion of the ECG data having a predetermined relationship to the predetermined feature of each of the waveforms;
(d) performing a discrete Fourier transform on each of the data portions to produce a plurality of points in the complex plane characterizing the natural complex frequencies of each data portion;
(e) categorizing each plurality of points in the complex plane into one of a plurality of bins by determining whether each point in the complex plane falls within a corresponding window area of predetermined size that is centered about a corresponding point that characterizes the natural complex frequencies of a waveform that represents the bin; and
(f) identifying each of the samples portions of ECG data with the bin into which the corresponding plurality of points in the complex plane is categorized.

8. The method of claim 7 wherein step (e) further comprises identifying all bins for which each of the plurality of points characterizing the natural complex frequencies of each data portion lies within each of the window areas located around the corresponding points that characterize the natural complex frequencies of a waveform that represents the bin and defining a new bin if no existing bin can be identified with the transformed data portion.

9. The method of claim 8 wherein a waveform portion is categorized in the bin identified with the transformed data portion which minimizes the sum of the magnitude of the errors between points defining the transformed data portion and the corresponding points that characterize the natural complex frequencies of a waveform that represents the bin.

10. The method of claim 7 the predetermined size of the window area is determined by a sensitivity criterion of acceptable similarity between two waveforms.

11. The method of claim 7 wherein, if any of the sampled data portions can be identified with more than one of the bins, step (e) further comprises categorizing the sampled data portion into the bin that minimizes the sum of the magnitudes of the differences between the points defining the corresponding transformed portion and the points that characterize the natural complex frequencies of a waveform that represents the bin.

12. The method of claim 11 wherein, if any of the sampled data portions is not identified with any of the existing bins, it is identified with a bin defined by the points that characterize the natural complex frequencies of the sampled data portion.

13. A method for categorizing ECG data which contains a plurality of heartbeat waveforms, each waveform having a predetermined feature, the method comprising the steps of:
(a) sampling the data with a uniform sampling frequency;
(b) detecting the occurrence of the predetermined feature in the sampled data and identifying each of the waveforms containing the predetermined feature;
(c) selecting each portion of each of the ECG data having a predetermined relationship with the predetermined feature of each of the waveforms;
(d) performing a discrete Fourier transformation of each of the data portions and producing a plurality of points in the complex plane corresponding to the natural complex frequencies of each of the transformed portions;
(e1) categorizing each plurality of points in the complex plane into one of a plurality of bins by comparing the location of each of the plurality of points in the complex plane with an area defined by a window located around the corresponding one of each of the plurality of points in the complex plane that characterizes the natural complex frequencies of a waveform that represents the bin;
(e2) identifying all bins for which each of the plurality of points defining the transformed portion lies within each of the areas defined by the windows located around the corresponding points that characterize the natural complex frequencies of a waveform that represents the bin, the sampled portion being categorized in the bin identified with the transformed portion which minimizes the sum of the magnitude of the errors between points defining the transformed waveform portion and the corresponding points that characterize the natural complex frequencies of a waveform that represents the bin;

(e3) categorizing the sampled waveform with a new bin if no existing bin can be identified with the transformed portion, the new bin being characterized by the natural complex frequencies of a waveform that represents the bin; and (f) identifying each of the sampled waveforms with the bin with which the corresponding transformed portion is categorized.

* * * * *